US009759810B1

(12) United States Patent
Sankar

(10) Patent No.: US 9,759,810 B1
(45) Date of Patent: Sep. 12, 2017

(54) HYBRID PULSE COMPRESSION WAVEFORM FOR HIGH RESOLUTION IMAGING

(71) Applicant: Scidea Research, Inc., Tustin, CA (US)

(72) Inventor: Pat Sankar, Tustin, CA (US)

(73) Assignee: Scidea Research, Inc., Tustin, CA (US)

( * ) Notice: Subject to any disclaimer, the term of this patent is extended or adjusted under 35 U.S.C. 154(b) by 0 days.

(21) Appl. No.: 15/443,959

(22) Filed: Feb. 27, 2017

Related U.S. Application Data

(60) Provisional application No. 62/454,596, filed on Feb. 3, 2017.

(51) Int. Cl.
*G01S 13/02* (2006.01)
*G01S 7/282* (2006.01)
(Continued)

(52) U.S. Cl.
CPC ............... *G01S 13/02* (2013.01); *G01S 7/22* (2013.01); *G01S 7/282* (2013.01); *G01S 13/885* (2013.01);
(Continued)

(58) Field of Classification Search
CPC .. G01S 13/02; G01S 2013/0236; G01S 7/282; G01S 13/885; G01S 13/89;
(Continued)

(56) References Cited

U.S. PATENT DOCUMENTS 4,566,010 A * 1/1986 Collins ................. G01S 13/288
342/189
8,747,321 B2 * 6/2014 Sankar ..................... A61B 8/14
600/437
(Continued)

OTHER PUBLICATIONS

D. B. Koch and W. H. Tranter, "Processing considerations for hybrid waveforms utilizing complementary phase coding and linear frequency stepping," IEEE International Conference on Radar, Arlington, VA, 1990, pp. 606-611. doi: 10.1109/RADAR.1990.201113.*
(Continued)

*Primary Examiner* — Matthew M Barker
(74) *Attorney, Agent, or Firm* — Knobbe Martens Olson & Bear LLP

(57) ABSTRACT

A hybrid pulse compression RF system is provided herein in which an enhanced noise waveform and a hybrid waveform are generated to detect a target. For example, the system includes a signal generator that generates an LFM waveform and an enhanced waveform in sequence such that a transmitter of the system transmits the waveforms in the generated sequence in a direction of a possible target. The enhanced waveform may be a partially randomized version of the LFM waveform. If a target is present, the waveforms reflect off the target and are captured by the system in the sequence in which the originally generated waveforms are transmitted. Once captured, the reflected waveforms are processed by the system to generate a hybrid waveform for display such that the range and Doppler resolution and detection capabilities are significantly superior to the state of the art LFM or noise waveform RF systems.

20 Claims, 39 Drawing Sheets

(51) Int. Cl.
- *G01S 13/88* (2006.01)
- *G01S 13/89* (2006.01)
- *G01S 7/22* (2006.01)
- G01S 15/89 (2006.01)
- G01S 17/89 (2006.01)
- G01S 7/51 (2006.01)
- G01S 7/62 (2006.01)
- A61B 6/00 (2006.01)
- G01S 13/91 (2006.01)
- G01S 17/10 (2006.01)

(52) U.S. Cl.
CPC ............ *G01S 13/89* (2013.01); *A61B 6/461* (2013.01); *G01S 7/51* (2013.01); *G01S 7/6272* (2013.01); *G01S 13/91* (2013.01); *G01S 15/89* (2013.01); *G01S 15/8961* (2013.01); *G01S 17/102* (2013.01); *G01S 17/89* (2013.01); *G01S 2013/0236* (2013.01)

(58) Field of Classification Search
CPC ...... G01S 7/22; G01S 17/102; G01S 15/8961; G01S 13/91; G01S 15/89; G01S 7/6272; G01S 17/89; G01S 7/51; A61B 6/461
See application file for complete search history.

(56) References Cited

U.S. PATENT DOCUMENTS

| | | | | |
|---|---|---|---|---|
| 2005/0225481 | A1* | 10/2005 | Bonthron | G01S 7/032 342/175 |
| 2015/0285897 | A1* | 10/2015 | Kilty | G01S 7/02 342/195 |
| 2016/0306039 | A1* | 10/2016 | Selzler | G01S 13/95 |

OTHER PUBLICATIONS

Li Yingjun, Shang She and Zhang Xiushe, "The hybrid signal applied for low-flyer detection and tracking," 2001 CIE International Conference on Radar Proceedings (Cat No. 01TH8559), Beijing, 2001, pp. 401-404. doi: 10.1109/ICR.2001.984716.*

* cited by examiner

HYBRID PULSE COMPRESSION WAVEFORM FOR HIGH RESOLUTION IMAGING

CROSS-REFERENCE TO RELATED APPLICATIONS

Any and all applications for which a foreign or domestic priority claim is identified in the Application Data Sheet as filed with the present application, are hereby incorporated by reference under 37 CFR 1.57. This application claims the benefit of U.S. Provisional Application No. 62/454,596, filed Feb. 3, 2017 and titled "HYBRID PULSE COMPRESSION WAVEFORM FOR HIGH RESOLUTION IMAGING," which is hereby incorporated herein by reference in its entirety.

BACKGROUND

Pulse compression techniques can be used by imaging systems and devices that transmit and/or receive analog signals, such as radio detection and ranging (RADAR) signals, light detection and ranging (LIDAR) signals, sound navigation and ranging (SONAR) signals, ultrasound signals, magnetic resonance imaging (MRI) signals, and/or the like, to identify targets. Various techniques for pulse compression are known in the art.

However, conventional techniques have various limitations and disadvantages. For example, some conventional techniques offer high resolution detection of slow-moving or stationary targets, but suffer from Doppler effects or other similar issues when targets are moving at a high speed. Conversely, other conventional techniques offer high resolution detection of targets moving at a high speed, but do not exhibit the range resolution necessary to provide high resolution detection of stationary or slow-moving targets. Still other conventional techniques are useful for detecting targets behind walls or other structures, but exhibit stronger background clutter than other conventional techniques.

SUMMARY

One aspect of the disclosure provides a target detection system. The system comprises a signal generator configured to generate a linear frequency modulation (LFM) waveform and a partially randomized LFM waveform. The system further comprises a transmitter configured to transmit the LFM waveform and the partially randomized LFM waveform in a sequential order. The system further comprises a receiver configured to receive a reflected LFM waveform and a reflected partially randomized LFM waveform, wherein the reflected LFM waveform comprises a version of the LFM waveform that reflected off a target, and wherein the reflected partially randomized LFM waveform comprises a version of the partially LFM waveform that reflected off the target. The system further comprises a processor in communication with the receiver and the signal generator and configured with specific computer-executable instructions to: process the reflected LFM waveform using the generated LFM waveform to form a processed LFM waveform; process the reflected partially randomized LFM waveform using the generated partially randomized LFM waveform to form a processed partially randomized LFM waveform; and combine the processed LFM waveform and the processed partially randomized LFM waveform to form a hybrid waveform. The system further comprises a display device configured to display a graphical representation of the hybrid waveform in a user interface.

The system of the preceding paragraph can include any sub-combination of the following features: where the transmitter is configured to transmit the LFM waveform before the partially randomized LFM waveform; where the receiver is configured to receive the reflected LFM waveform before the reflected partially randomized LFM waveform; where the transmitter is configured to transmit the LFM waveform after the partially randomized LFM waveform; where the receiver is configured to receive the reflected LFM waveform after the reflected partially randomized LFM waveform; where the transmitter is further configured to concatenate the LFM waveform and the partially randomized LFM waveform; where the transmitter is further configured to insert a time delay corresponding to no signal between the LFM waveform and the partially randomized LFM waveform; the processor is further configured with specific computer-executable instructions to: cross-correlate the reflected LFM waveform with the generated LFM waveform to form the processed LFM waveform, and cross-correlate the reflected partially randomized LFM waveform with the generated partially randomized LFM waveform to form the processed partially randomized LFM waveform; where the processor is further configured with specific computer-executable instructions to compute a product of the processed LFM waveform and the processed partially randomized LFM waveform; where the signal generator is further configured to: group one or more samples of the LFM waveform into one or more subgroups, randomly permute samples in each subgroup using a random permutation to form a randomized signal, compute a truncated fast Fourier transform (FFT) of the randomized signal, and compute an inverse FFT of the truncated FFT to form the partially randomized LFM waveform; where the graphical representation comprises an indication of a location of the target; where the LFM waveform is generated at a first bandwidth frequency, and wherein the partially randomized LFM waveform is generated at the first bandwidth frequency; and where the target detection system is one of a radio detection and ranging (RADAR) system, a light detection and ranging (LIDAR) system, a sound navigation and ranging (SONAR) system, an ultrasound system, a magnetic resonance imaging (MRI) system, or a computing tomography (CT) system.

Another aspect of the disclosure provides a method for detecting a target. The method comprises: as implemented by a target detection system comprising physical hardware, generating a poly-phase code waveform; generating a partially randomized poly-phase code waveform; transmitting the poly-phase code waveform and the partially randomized poly-phase code waveform in a sequential order; receiving a reflected poly-phase code waveform and a reflected partially randomized poly-phase code waveform, wherein the reflected poly-phase code waveform comprises a version of the poly-phase code waveform that reflected off a target, and wherein the reflected partially randomized poly-phase code waveform comprises a version of the partially poly-phase code waveform that reflected off the target; processing the reflected poly-phase code waveform using the generated poly-phase code waveform to form a processed poly-phase code waveform; processing the reflected partially randomized poly-phase code waveform using the generated partially randomized poly-phase code waveform to form a processed partially randomized poly-phase code waveform; and combining the processed poly-phase code waveform and the processed partially randomized poly-phase code waveform to form a hybrid waveform that, when graphically displayed, indicates whether the target is detected.

The method of the preceding paragraph can include any sub-combination of the following features: where transmitting the poly-phase code waveform and the partially randomized poly-phase code waveform further comprises transmitting the poly-phase code waveform before the partially randomized poly-phase code waveform; where receiving a reflected poly-phase code waveform and a reflected partially randomized poly-phase code waveform further comprises receiving the reflected poly-phase code waveform before the reflected partially randomized poly-phase code waveform; where the method comprises concatenating the poly-phase code waveform and the partially randomized poly-phase code waveform; where processing the reflected poly-phase code waveform, processing the reflected partially randomized poly-phase code waveform, and combining the processed poly-phase code waveform and the processed partially randomized poly-phase code waveform further comprises: cross-correlating the reflected poly-phase code waveform with the generated poly-phase code waveform to form the processed poly-phase code waveform, cross-correlating the reflected partially randomized poly-phase code waveform with the generated partially randomized poly-phase code waveform to form the processed partially randomized poly-phase code waveform, and computing a product of the processed poly-phase code waveform and the processed partially randomized poly-phase code waveform; where the poly-phase code waveform is one of a linear frequency modulation (LFM) waveform, a Gold code waveform, or a Barker code waveform; and where the target detection system is one of a radio detection and ranging (RADAR) system, a light detection and ranging (LIDAR) system, a sound navigation and ranging (SONAR) system, an ultrasound system, a magnetic resonance imaging (MRI) system, or a computing tomography (CT) system.

BRIEF DESCRIPTION OF DRAWINGS

Throughout the drawings, reference numbers may be re-used to indicate correspondence between referenced elements. The drawings are provided to illustrate example embodiments described herein and are not intended to limit the scope of the disclosure.

DETAILED DESCRIPTION

Introduction

Figure 1A:
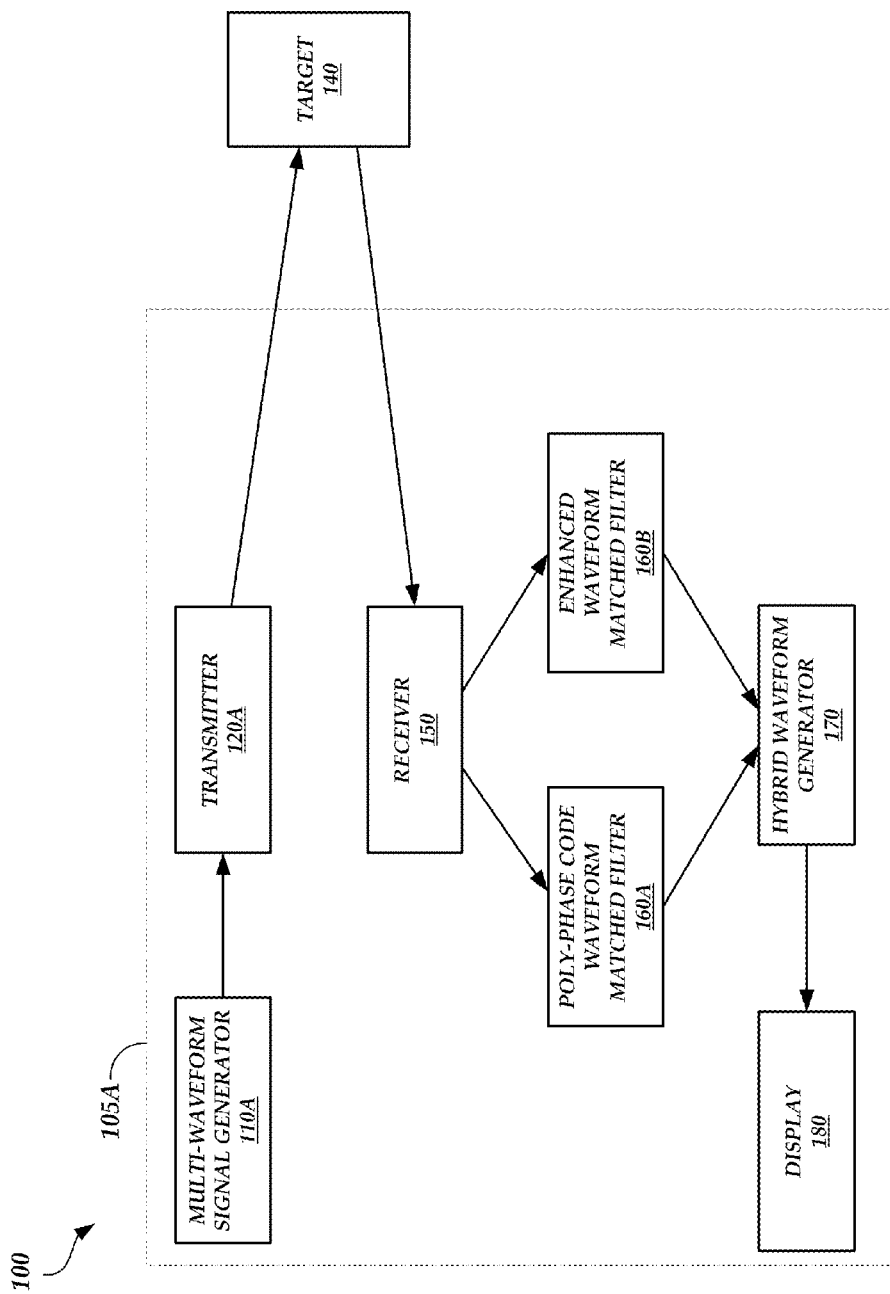
FIGS. 1A-1F are block diagrams of illustrative hybrid pulse compression radio frequency (RF) systems in a target detection environment.

As described above, conventional pulse compression techniques suffer from various limitations and disadvantages. For example, conventional pulse compression techniques include linear frequency modulation (LFM or chirp signal), spread spectrum waveforms (e.g., orthogonal code waveforms), noise waveforms (e.g., pseudorandom number sequences), and/or the like. Examples of orthogonal code waveforms include Walsh-Harr code waveforms and Gold code waveforms. LFM is primarily used in radar detection and in the imaging industry. While LFM provides high resolution detection of stationary or slow-moving targets, LFM suffers from the coupling of range, Doppler effects, and/or other similar issues when targets are moving at a high speed. The Gold code is primarily used for the detection of high speed targets; however, the Gold code does not exhibit the range resolution necessary to provide high resolution detection of stationary or slow-moving targets (e.g., the Gold code has less range resolution than LFM). In addition, noise waveforms can be useful for detecting targets behind walls or other structures, but noise waveforms exhibit stronger background clutter than LFM and other conventional pulse compression techniques.

Thus, it may be beneficial to develop a waveform that exhibits the positive characteristics of conventional pulse compression techniques without suffering from the limitations discussed above. Accordingly, the present application discloses a hybrid pulse compression RF system used to detect a target (e.g., a vehicle, such as a plane, helicopter, ship, submarine, automobile, etc., a human body part, such as a limb, a bone, an organ, a blood vessel, a tumor, etc., an animal, an extraterrestrial object, etc.) in which the hybrid pulse compression RF system generates an enhanced noise waveform and a hybrid waveform derived from the enhanced noise waveform that combine the benefits of LFM and the noise waveform. For example, the hybrid pulse compression RF system can include a multi-waveform signal generator that generates an LFM waveform and an enhanced waveform, which is a partially randomized poly-phase code waveform and is also referred to herein as a "partially randomized LFM waveform" or a "partially randomized poly-phase code waveform" and is described in greater detail below with respect to FIG. 2. As described herein, examples of a poly-phase code waveform include an LFM waveform, a Gold code waveform, a Barker code waveform, a pseudorandom number code waveform, and/or the like. The multi-waveform signal generator may generate the LFM waveform and the enhanced waveform in sequence such that a transmitter of the hybrid pulse compression RF system transmits the waveforms in the generated sequence via an antenna in a direction in which a target may be located. The multi-waveform signal generator can generate the LFM waveform and the enhanced waveform in any sequence. If a target is present, the waveforms may reflect off the target and be captured by an antenna of a receiver of the hybrid pulse compression RF system. The reflected waveforms may be captured in the sequence in which the originally generated waveforms are transmitted.

Once captured, the reflected waveforms may be processed by the hybrid pulse compression RF system to generate a hybrid waveform. The hybrid waveform may represent data that indicates the detection of a target. For example, the reflected LFM waveform may be processed by a matched filter that cross-correlates the reflected LFM waveform with the originally generated LFM waveform. Likewise, the reflected enhanced waveform may be processed by a matched filter that cross-correlates the reflected enhanced waveform with the originally generated enhanced waveform. The output of both matched filters may be combined (e.g., a product may be taken of both outputs) to form the hybrid waveform. The hybrid waveform may be constructed such that the range and Doppler resolution and detection capabilities are significantly superior (e.g., about an order of magnitude improvement in many applications) to the state of the art LFM or noise waveform RF systems. The hybrid pulse compression RF system may display the hybrid waveform in a user interface (e.g., as part of a range-Doppler map and/or movie).

Optionally, the hybrid pulse compression RF system can include individual signal generators instead of a multi-waveform signal generator, where one signal generator is configured to generate the LFM waveform and another signal generator is configured to generate the enhanced waveform. Furthermore, the hybrid pulse compression RF system may include a transceiver, multiple transmitters and/or receivers (e.g., one for each generated waveform), multiple transceivers, and/or the like instead of a separate transmitter and receiver.

While the present disclosure is described with respect to the generation and processing of an LFM waveform, this is not meant to be limiting. For example, the multi-waveform signal generator may generate a Gold code waveform, a noise waveform, a pseudorandom number code waveform, a Barker code waveform, and/or any other poly-phase code waveform in place of the LFM waveform. The hybrid pulse compression RF system may then process and use the poly-phase code waveform as described above with respect to the LFM waveform to generate the hybrid waveform. Furthermore, while the present disclosure is described such that the enhanced waveform is a partially randomized version of the LFM waveform, this is not meant to be limiting as the enhanced waveform may be a partially randomized version of any poly-phase code waveform. For example, the enhanced waveform may be a partially randomized version of the Gold code waveform, a partially randomized version of a noise waveform, a partially randomized version of a pseudorandom number code waveform, a partially randomized version of the Barker code waveform, and/or a partially randomized version of any other poly-phase code waveform.

In addition, while the present disclosure is described with respect to the generation of two waveforms for detecting a target, this is not meant to be limiting. For example, the hybrid pulse compression RF system can generate three or more waveforms (e.g., an LFM waveform, a Gold code waveform, and the enhanced waveform) and combine the cross-correlated versions of the reflected waveforms to form the hybrid waveform.

Furthermore, while the hybrid pulse compression RF system may be capable of generating a plurality of waveforms for detecting a target, it is not necessary that the hybrid pulse compression RF system generate all waveforms that the hybrid pulse compression RF system is capable of generating. For example, the hybrid pulse compression RF system can operate in a target detection mode in which only the LFM waveform is generated and used to detect a target. As another example, the hybrid pulse compression RF system can operate in a target detection mode in which only the enhanced waveform is generated and used to detect a target.

The hybrid pulse compression RF system described herein can be implemented in a variety of use cases. For example, the waveforms generated by the individual or multi-waveform signal generators can be used in a manner as described herein to detect targets in RADAR, LIDAR, SONAR, ultrasound, MRI, computed tomography (CT) applications, and/or any other application in which a signal is emitted, the signal reflects off a target, and the reflected signal is captured and processed to detect the target. Thus, the hybrid pulse compression RF system described herein does not necessarily transmit the generated waveforms as radio signals and can also be referred to herein generally as a "hybrid pulse compression system." The hybrid pulse compression RF system may instead include different types of transducers (e.g., antennas, lasers, electro-acoustic transducers, transducer probes, X-RAY tubes, etc.) that can output the generated waveforms in any medium (e.g., air, water, etc.) and receive reflected waveforms that travel through any medium.

The foregoing aspects and many of the attendant advantages of this disclosure will become more readily appreciated as the same become better understood by reference to the following detailed description, when taken in conjunction with the accompanying drawings.

Example Hybrid Pulse Compression RF Systems Using a Hybrid Waveform

FIGS. 1A-1F are block diagrams of illustrative hybrid pulse compression RF systems 105A-105F in a target detection environment 100. As illustrated in FIG. 1A, the hybrid pulse compression RF system 105A includes a multi-waveform signal generator 110A, a transmitter 120A, a receiver 150, a poly-phase code waveform matched filter 160A, an enhanced waveform matched filter 160B, a hybrid waveform generator 170, and an optional display 180. The target detection environment 100 further includes a target 140.

The multi-waveform signal generator 110A may be configured to generate one or more different types of waveforms. For example, the multi-waveform signal generator 110A can generate an LFM waveform, a Gold code waveform, a Barker code waveform, a noise waveform, an enhanced waveform, and/or the like. For simplicity, the multi-waveform signal generator 110A is described herein as generating the LFM waveform and the enhanced waveform. The multi-waveform signal generator 110A can generate the LFM waveform and the enhanced waveform sequentially. For example, the multi-waveform signal generator 110A can generate the LFM waveform first for a set period of time (e.g., a pulse length, such as 1 µs, 10 µs, 100 µs, etc.) and then generate the enhanced waveform second for a set period of time (e.g., a pulse length, such as 1 µs, 10 µs, 100 µs, etc.) that may or may not be the same as the LFM waveform time period. The multi-waveform signal generator 110A may implement a programmable delay before generating the enhanced waveform such that no signal is generated between the generated LFM and enhanced waveforms for a set period of time (e.g., one pulse length, such as 1 µs, 10 µs, 100 µs, etc.) (see FIGS. 16A and 16B). In alternative embodiments, the multi-waveform signal generator 110A generates the LFM waveform after the enhanced waveform. In still other embodiments, the multi-waveform signal generator 110A generates the LFM waveform and the enhanced waveform simultaneously or overlapping in time, but outputs the waveforms sequentially. The multi-waveform signal generator 110A may generate both waveforms at the same frequency or within the same range of frequencies. In addition, the waveforms may be generated at any frequency (e.g., radio frequencies, ultrasound frequencies, microwave frequencies, X-RAY frequencies, etc.). Additional details on how the multi-waveform signal generator 110A generates the enhanced signal are provided below with respect to FIG. 2. The multi-waveform signal generator 110A can repeat this process any number of times (e.g., until target detection is paused or stopped) to generate multiple pairs of LFM and enhanced waveforms.

The multi-waveform signal generator 110A can output the generated waveforms to the transmitter 120A for transmission via an antenna. The antenna of the transmitter 120A can be any type of antenna, such as a television antenna, a radio antenna, phased array antennas, a parabolic dish antenna, a radio frequency (RF) coil used in MRI applications (e.g., a coil used in a medical scanning device like an MRI machine), and/or the like. Alternatively, the transmitter 120A can directly output the generated waveforms without an antenna. For example, the transmitter 120A may include a transducer, such as a laser used in LIDAR applications, an electro-acoustic transducer used in SONAR applications, a transducer probe that transmits acoustic signals (e.g., sound waves) for use in ultrasound applications, an X-RAY tube used in CT applications, and/or the like.

In some embodiments, the waveforms generated by the multi-waveform signal generator 110A are digital signals. Thus, the multi-waveform signal generator 110A and/or transmitter 120A may include a digital-to-analog converter (DAC) through which the waveforms pass such that analog versions of the waveforms can be transmitted via the antenna 130A. In other embodiments, the waveforms generated by the multi-waveform signal generator 110A are analog signals and therefore may not pass through a DAC before being transmitted.

The waveforms may be transmitted in sequence (e.g., the sequence in which the waveforms are generated). Thus, if the target 140 is present at a location that falls within a path of the LFM and enhanced waveform transmission, then the first waveform in the sequence (e.g., the LFM waveform) may reflect off the target 140 first and then the second waveform in the sequence (e.g., the enhanced waveform) may reflect off the target 140. As described above, there may be a programmable delay between the first waveform output by the multi-waveform signal generator 110A and the second waveform output by the multi-waveform signal generator 110A. The multi-waveform signal generator 110A may be configured to set the programmable delay to a low enough value such that the speed of travel of the target 140 does not cause a situation in which the first waveform reflects off the target 140 and the second waveform does not reflect off the target 140 because the target 140 is no longer in the transmission path. Because of the extremely small delay between the two waveforms, it may be assumed that the target dynamic and scattering properties are identical or nearly identical for both waveforms. This may ensure that the range-Doppler maps formed with the two different waveforms are generated from the same or nearly the same target moving scenario.

The reflected LFM and enhanced waveforms can be received by the receiver 150. As an example, the receiver 150 can be any signal reception device, such as any type of antenna (e.g., an RF antenna included in RADAR machines or medical scanning devices), a photodetector used in LIDAR applications, a hydrophone used in SONAR applications, a transducer probe that receives sound waves for use in ultrasound applications, and/or X-RAY detectors used in CT applications. The order in which the reflected waveforms are received may be the same order in which the originally generated waveforms are transmitted. The receiver 150 may include an analog-to-digital converter (ADC) to convert the received waveforms from an analog signal format to a digital signal format. The receiver 150 may then pass the digital version of the reflected LFM waveform to the poly-phase code waveform matched filter 160A and the digital version of the reflected enhanced waveform to the enhanced waveform matched filter 160B. The receiver 150 may identify the appropriate matched filter 160A or 160B to forward a received reflected waveform based on information provided by the multi-waveform signal generator 110A. For example, the multi-waveform signal generator 110A can inform the receiver 150 of which waveform is generated first and which waveform is generated second. Thus, when a pair of reflected waveforms, the receiver 150 can identify the portion of a received signal corresponding to the first reflected waveform (e.g., using edge detection or similar techniques) and forward the first reflected waveform to the matched filter 160A or 160B that corresponds with the first waveform in sequence generated by the multi-waveform signal generator 110A. Likewise, the receiver 150 can then identify the portion of the received signal corresponding to the second reflected waveform and forward the second reflected waveform to the matched filter 160A or 160B that corresponds with the second waveform in sequence generated by the multi-waveform signal generator 110A.

The poly-phase code waveform matched filter 160A can process the digital version of a reflected poly-phase code waveform. For example, the poly-phase code waveform matched filter 160A can cross-correlate a reflected poly-phase code waveform with an originally generated poly-phase code waveform (e.g., the poly-phase code waveform generated by a signal generator before transmission occurs). In this case, because an LFM waveform is transmitted, the poly-phase code waveform matched filter 160A processes the digital version of the reflected LFM waveform. Because the poly-phase code waveform matched filter 160A processes the digital version of the reflected LFM waveform, the poly-phase code waveform matched filter 160A may also be referred to herein as an LFM waveform matched filter. For example, the poly-phase code waveform matched filter 160A can cross-correlate the reflected LFM waveform with the originally generated LFM waveform as provided to the poly-phase code waveform matched filter 160A by the multi-waveform signal generator 110A. The poly-phase code waveform matched filter 160A can then transmit the result of the cross-correlation to the hybrid waveform generator 170.

The enhanced waveform matched filter 160B can process the digital version of the reflected enhanced waveform in a similar manner. For example, the enhanced waveform matched filter 160B can cross-correlate the reflected enhanced waveform with the originally generated enhanced waveform as provided to the enhanced waveform matched filter 160B by the multi-waveform signal generator 110A. The enhanced waveform matched filter 160B can then transmit the result of the cross-correlation to the hybrid waveform generator 170.

The hybrid waveform generator 170 can generate a hybrid waveform by combining the result of the cross-correlation performed by the poly-phase code waveform matched filter 160A and the result of the cross-correlation performed by the enhanced waveform matched filter 160B. For example, the hybrid waveform generator 170 may take a product of the cross-correlation results to form the hybrid waveform. The hybrid waveform may be a signal that indicates the detection of the target 140 (or the detection of no target if no target 140 is present in the waveform transmission path). The hybrid waveform generator 170 can forward the hybrid waveform to the optional display 180 such that the hybrid waveform can be plotted on a graph in a user interface to provide a user with a visual representation of a detected target 140 (if a target is detected). For example, the hybrid waveform data can be used by the hybrid waveform generator 170 to generate a range-Doppler movie that can be displayed in the user interface, where the range-Doppler movie provides a real-time or nearly real-time (e.g., within a few seconds of real-time) graphical representation of a past and/or current location of a detected target 140. Alternatively, the hybrid waveform generator 170 can transmit the hybrid waveform to a display external to the hybrid pulse compression RF system 105 for display in a user interface.

Figure 1B:
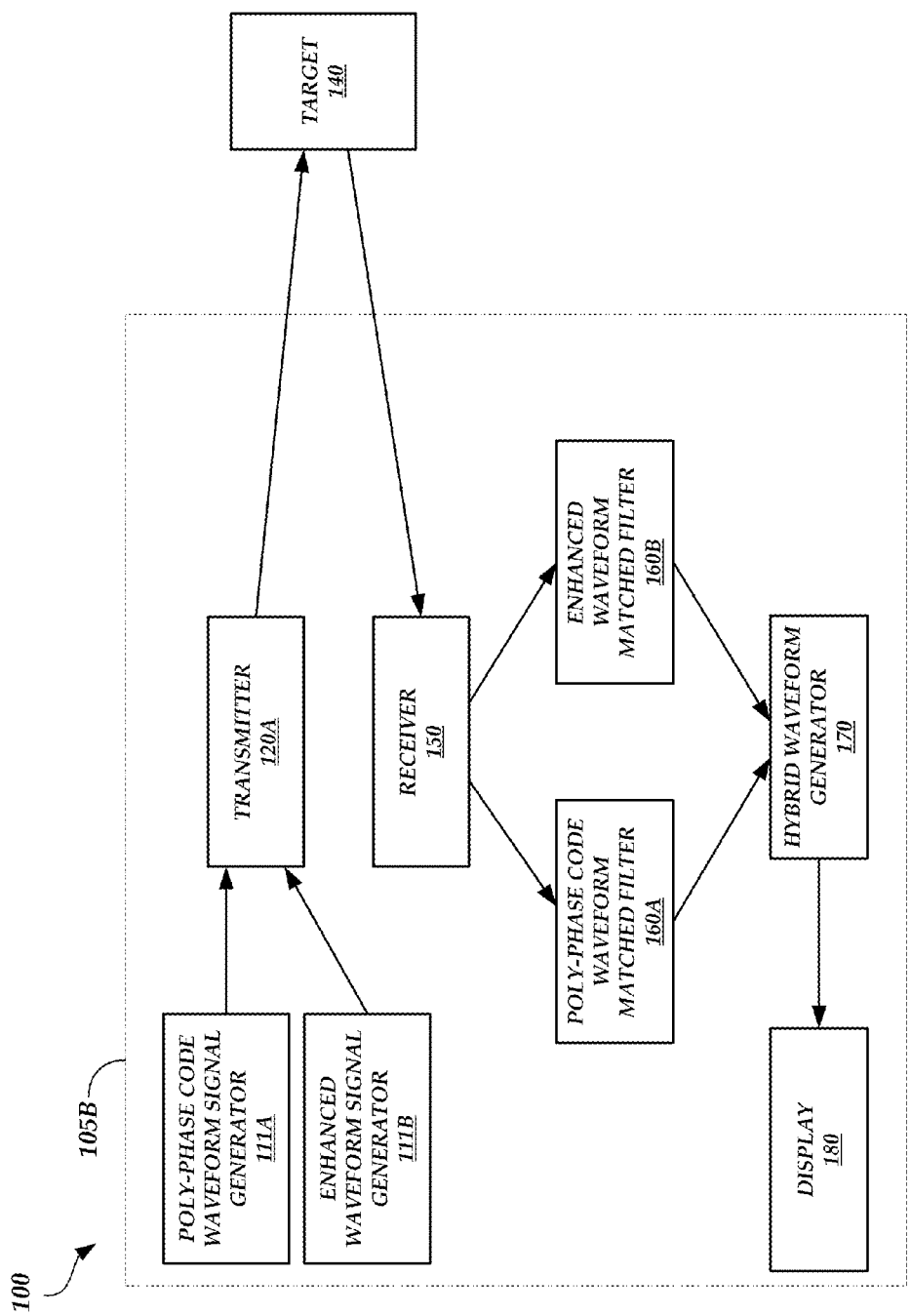

As illustrated in FIG. 1B, the hybrid pulse compression RF system 105B includes the transmitter 120A, the receiver 150, the poly-phase code waveform matched filter 160A, the enhanced waveform matched filter 160B, the hybrid waveform generator 170, and the optional display 180. However, unlike the hybrid pulse compression RF system 105A, the hybrid pulse compression RF system 105B does not include the multi-waveform signal generator 110A. Rather, the hybrid pulse compression RF system 105B includes a poly-phase code waveform signal generator 111A and an enhanced waveform signal generator 111B. The poly-phase code waveform signal generator 111A is configured to generate a poly-phase code waveform (e.g., the LFM waveform). The enhanced waveform signal generator 111B is configured to generate the enhanced waveform in a manner as described below with respect to FIG. 2.

The poly-phase code waveform signal generator 111A and the enhanced waveform signal generator 111B can generate the respective waveforms sequentially, in parallel, and/or overlapping in time. The signal generators 111A-111B can output the respective generated waveforms to the transmitter 120A for transmission in a manner as described above with respect to the hybrid pulse compression RF system 105A. For example, the transmitter 120A can transmit the generated LFM waveform followed by the generated enhanced waveform, or vice-versa. In some embodiments, the transmitter 120A includes a buffer to store the generated waveforms such that the waveforms can be transmitted in sequence even if the waveforms are received from the poly-phase code waveform signal generator 111A and the enhanced waveform signal generator 111B at the same time or at nearly the same time. The transmitter 120A may further delay transmission of the second waveform (e.g., the enhanced waveform) such that there is a period of time between transmission of the first waveform (e.g., the LFM waveform) and the second waveform in which no transmissions are made.

Figure 1C:
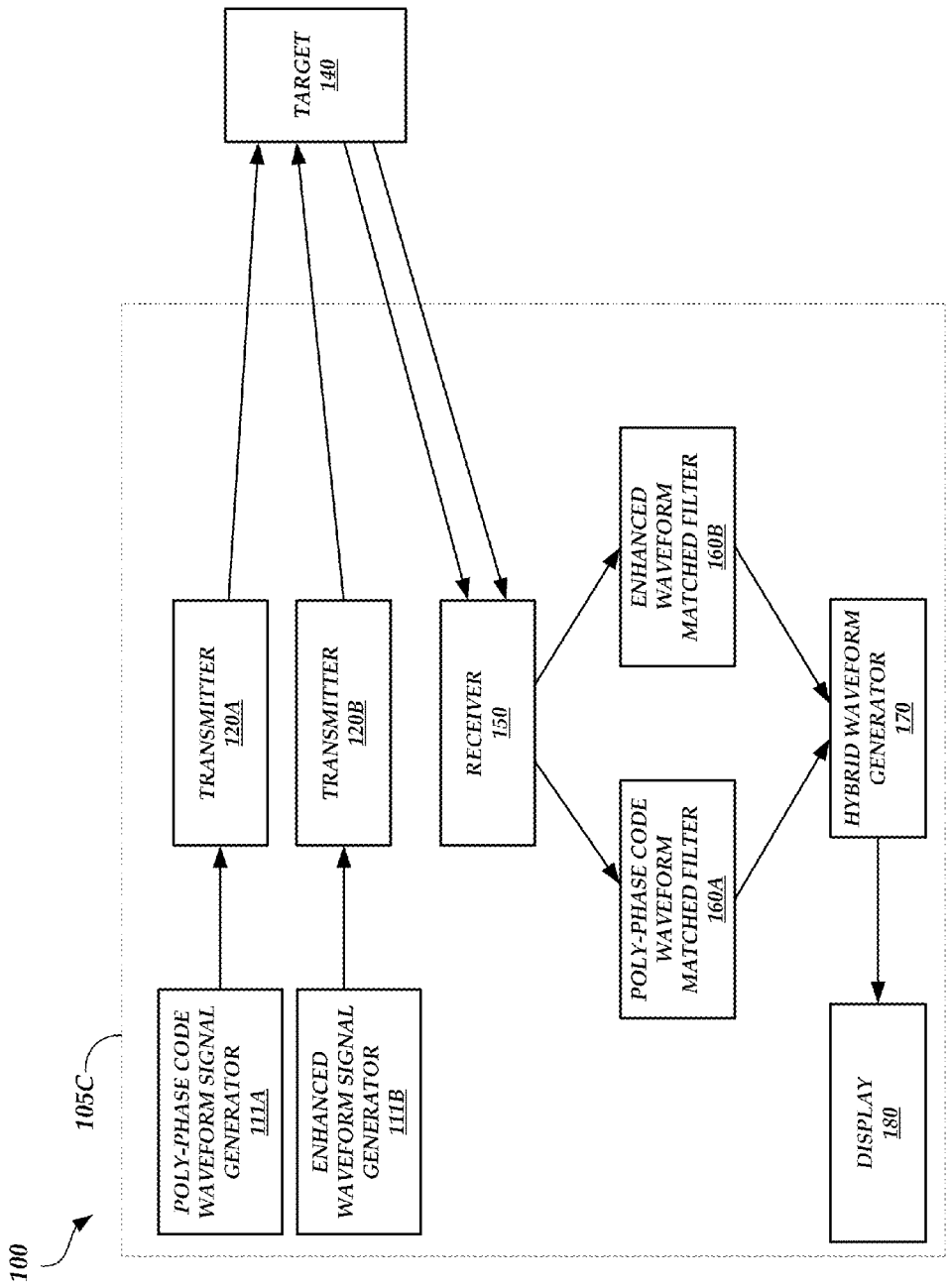

As illustrated in FIG. 1C, the hybrid pulse compression RF system 105C includes the poly-phase code waveform signal generator 111A, the enhanced waveform signal generator 111B, the transmitter 120A, the receiver 150, the poly-phase code waveform matched filter 160A, the enhanced waveform matched filter 160B, the hybrid waveform generator 170, and the optional display 180. Unlike the hybrid pulse compression RF systems 105A-105B, the hybrid pulse compression RF system 105C also includes a transmitter 120B. For example, the hybrid pulse compression RF system 105C may implement a multiple input single output (MISO) design such that the generated LFM waveform is transmitted via the transmitter 120A and the generated enhanced waveform is transmitted via a separate transmitter 120B. The reflected LFM and enhanced waveforms may then be received by a single receiver 150. In other embodiments, not shown, the hybrid pulse compression RF system 105C can implement a multiple input multiple output (MIMO) design such that the generated LFM waveform is transmitted via the transmitter 120A, the generated enhanced waveform is transmitted via a separate transmitter 120B, the reflected LFM waveform is received by a first receiver 150, and the reflected enhanced waveform is received by a separate second receiver 150.

Figure 1D:
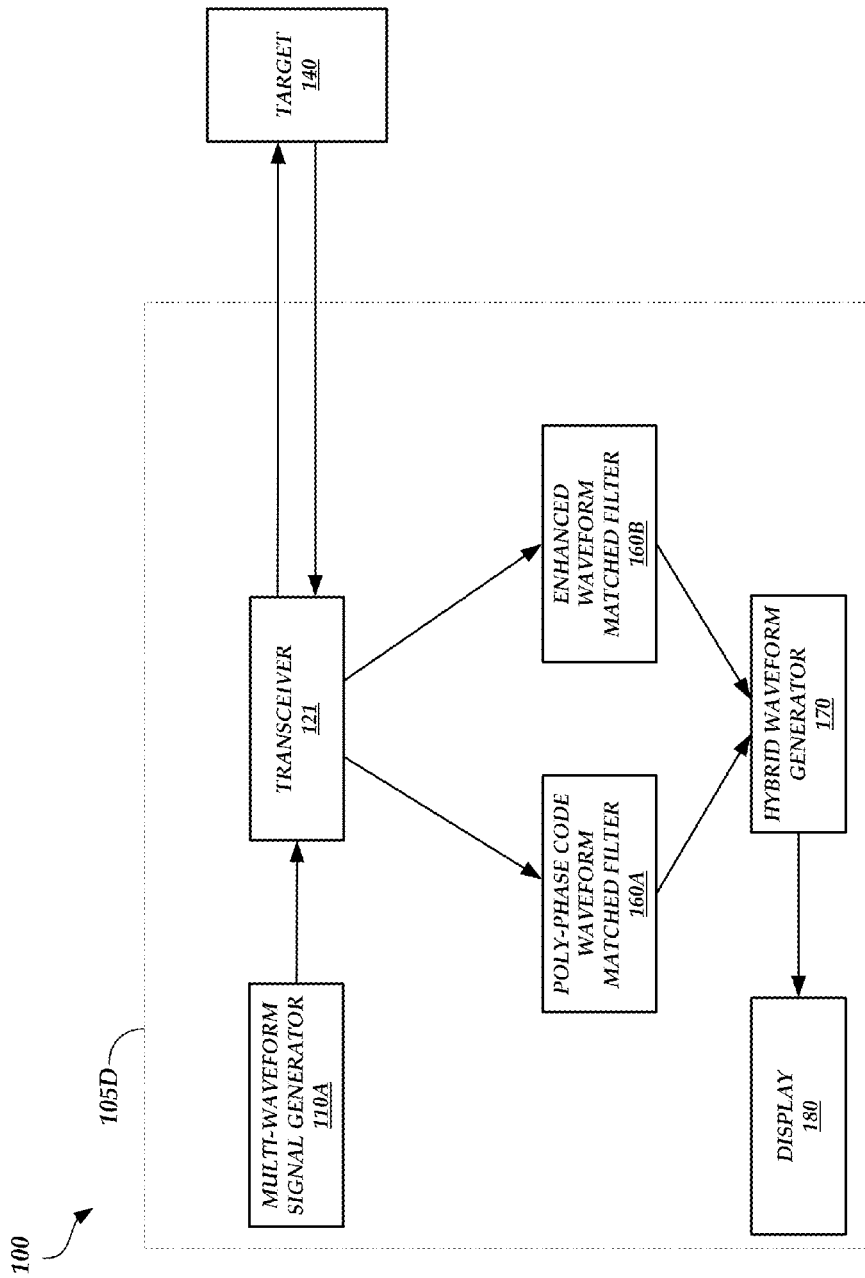

As illustrated in FIG. 1D, the hybrid pulse compression RF system 105D includes the multi-waveform signal generator 110A, the poly-phase code waveform matched filter 160A, the enhanced waveform matched filter 160B, the hybrid waveform generator 170, and the optional display 180. However, instead of a separate transmitter 120A and receiver 150, the hybrid pulse compression RF system 105D includes a transceiver 121 that performs the functionality of both the transmitter 120A and the receiver 150.

Figure 1E:
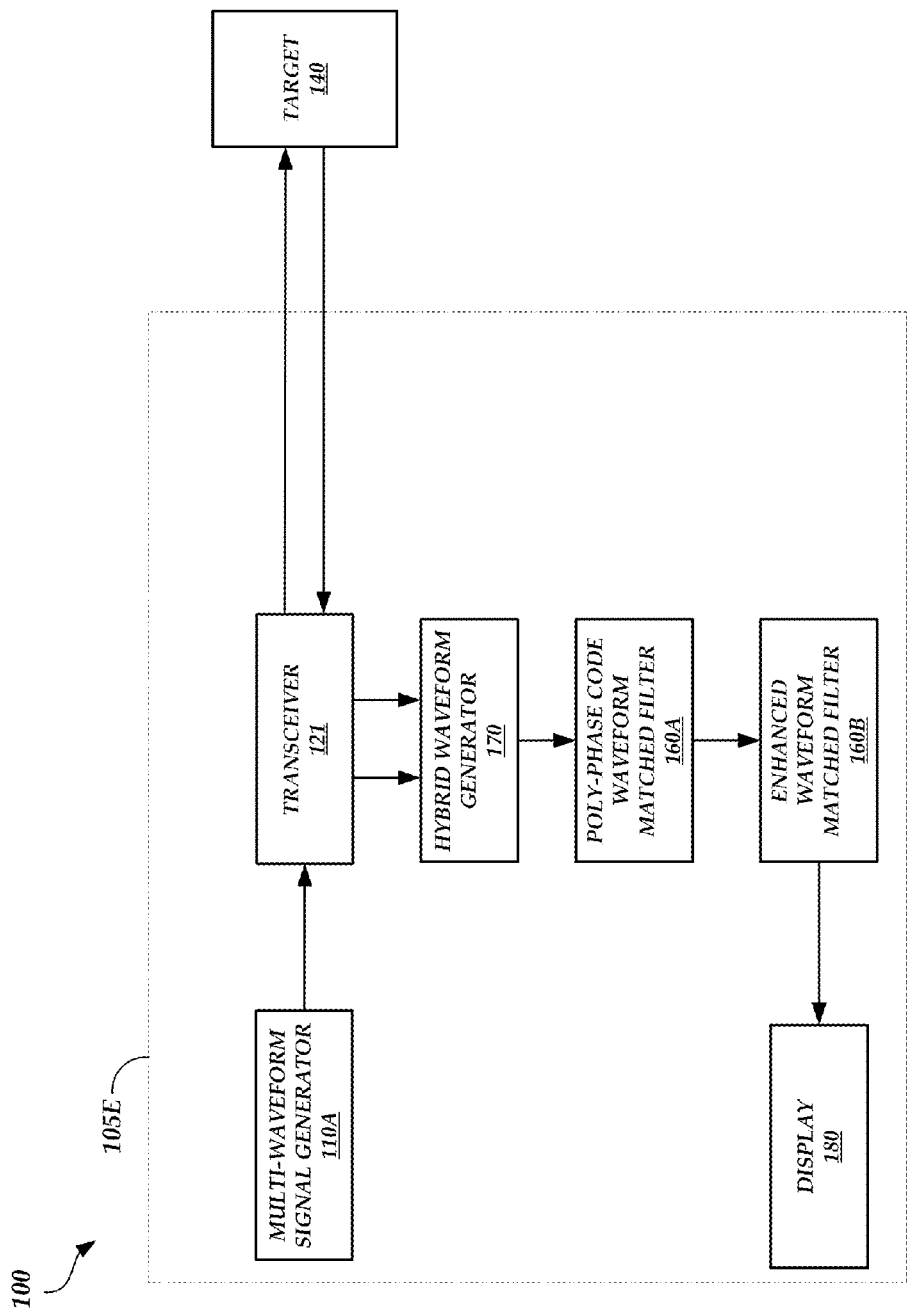

As illustrated in FIG. 1E, the hybrid pulse compression RF system 105E includes the multi-waveform signal generator 110A, the transceiver 121, the hybrid waveform generator 170, the poly-phase code waveform matched filter 160A, the enhanced waveform matched filter 160B, and the optional display 180. However, instead of the transceiver 121 sending the reflected waveforms to the poly-phase code waveform matched filter 160A and the enhanced waveform matched filter 160B, the transceiver 121 may instead send the reflected waveforms to the hybrid waveform generator 170. The hybrid waveform generator 170 may combine the reflected waveforms (e.g., take a product of the reflected waveforms) and then output the combined waveform to the poly-phase code waveform matched filter 160A. The poly-phase code waveform matched filter 160A may cross-correlate the combined waveform with the originally generated LFM waveform and send the result to the enhanced waveform matched filter 160B. The enhanced waveform matched filter 160B may then cross-correlate the output of the poly-phase code waveform matched filter 160A with the originally generated LFM waveform to produce the hybrid waveform. The hybrid waveform may then be output by the enhanced waveform matched filter 160B to the display 180. Alternatively, not shown, instead of sending the combined waveform to the poly-phase code waveform matched filter 160A, the hybrid waveform generator 170 can send the combined waveform to the enhanced waveform matched filter 160B. The enhanced waveform matched filter 160B can then cross-correlate the combined waveform with the originally generated enhanced waveform and send the result to the poly-phase code waveform matched filter 160A. The poly-phase code waveform matched filter 160A can then cross-correlate the output of the enhanced waveform matched filter 160B with the originally generated LFM waveform to form the hybrid waveform.

Figure 1F:
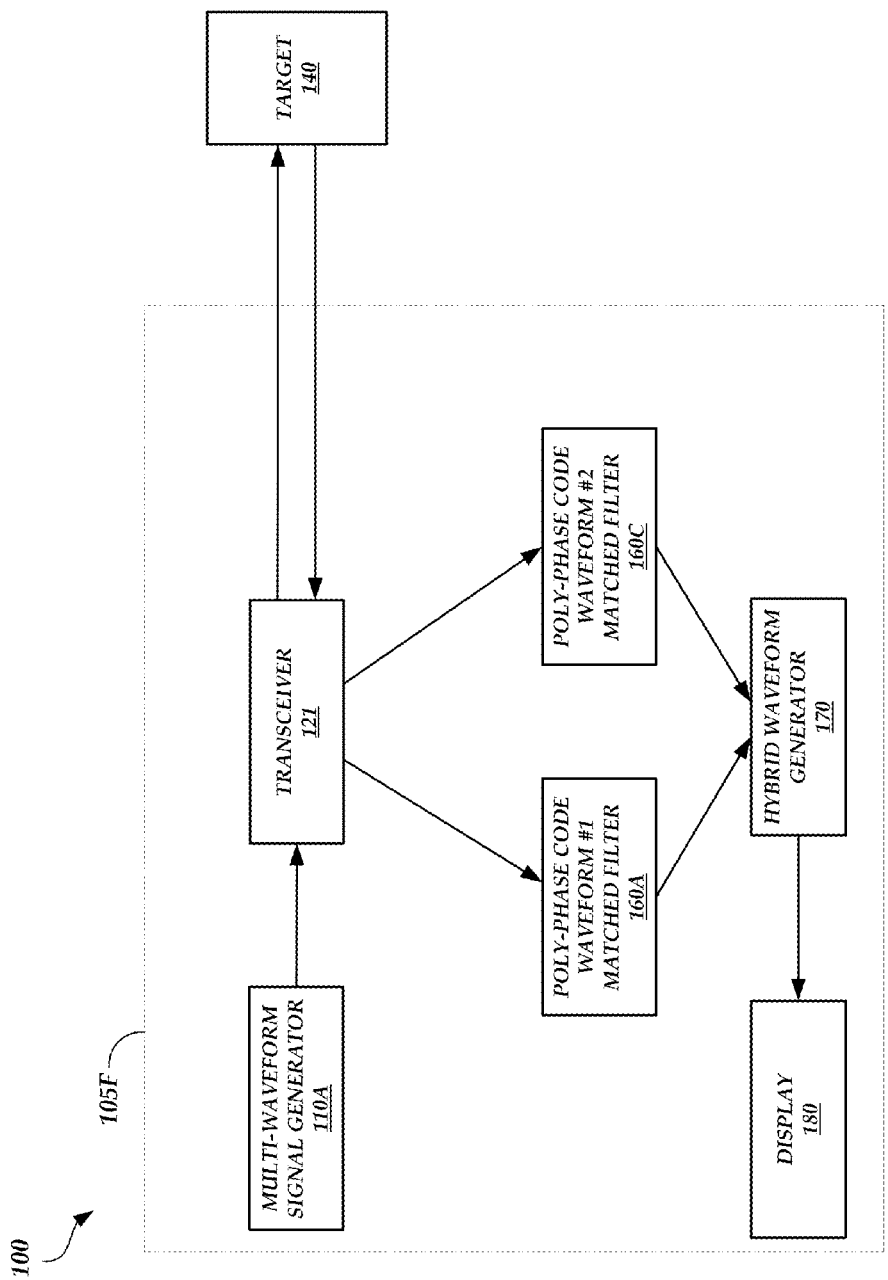

As illustrated in FIG. 1F, the hybrid pulse compression RF system 105F includes the multi-waveform signal generator 110A, the transceiver 121, the poly-phase code waveform matched filter 160A, the hybrid waveform generator 170, and the optional display 180. However, instead of including the enhanced waveform matched filter 160B, the hybrid pulse compression RF system 105F includes a second poly-phase code waveform matched filter 160C. For example, the multi-waveform signal generator 110A may generate the LFM waveform and a second poly-phase code waveform (e.g., a Gold code waveform, a Barker code waveform, etc.) instead of the enhanced waveform. The poly-phase code waveform matched filter 160C may therefore cross-correlate a reflected second poly-phase code waveform with the originally generated second poly-phase code waveform. In general, the multi-waveform signal generator 110A may generate any two poly-phase code waveforms (e.g., either the same or different poly-phase code waveforms) and the first and second poly-phase code waveform matched filters 160A and 160C may each perform a cross-correlation using a different reflected poly-phase code waveform in a manner as described herein (e.g., cross-correlate the reflected poly-phase code waveform with the originally generated version of the poly-phase code waveform). The hybrid waveform generator 170 can then combine the results of the two performed cross-correlations. Even though the hybrid pulse compression RF system 105F does not utilize the enhanced waveform, the hybrid pulse compression RF system 105F may still exhibit benefits over conventional pulse compression systems and techniques.

While FIGS. 1A-1F disclose specific embodiments of the hybrid pulse compression RF systems 105A-105F, this is not meant to be limiting. For example, the hybrid pulse compression RF system 105A may include any components or implement any features disclosed in the other hybrid pulse compression RF systems 105B-105F and the same may apply to the other hybrid pulse compression RF systems 105B-105F. As an illustrative example, instead of including the transmitter 120A and the receiver 150, the hybrid pulse compression RF system 105A may include the transceiver 121. As another illustrative example, instead of including the poly-phase code waveform signal generator 111A and the enhanced waveform signal generator 111B, the hybrid pulse compression RF system 105C may just include the multi-waveform signal generator 110A.

Furthermore, while the hybrid pulse compression RF systems 105A-105F include two matched filters 160A, 160B, and/or 160C, this is not meant to be limiting. The hybrid pulse compression RF systems 105A-105F may include at least one matched filter for each waveform generated by the signal generators 110A, 111A, and/or 111B.

The hybrid pulse compression RF systems 105A-105F may each include physical hardware, such as memory (e.g., a hard disk, a solid state drive, flash memory, random access memory (RAM), etc.), one or more processors, transmit circuitry, receive circuitry, oscillators, buffers, one or more DACs, one or more ADCs, one or more antennas and/or transducers, hydrophones, microphones, a display (e.g., LED display, LCD display, plasma display, etc.), and/or the like to implement the functionality described herein. For example, the memory may store instructions that, when executed by the one or more processors, causes the hybrid pulse compression RF system 105A-105F to implement the functionality of the signal generators 110A, 111A, and 111B, the poly-phase code waveform matched filter 160A, the enhanced waveform matched filter 160B, the poly-phase code waveform #2 matched filter 160C, the hybrid waveform generator 170, and/or the like described herein. Additional details of the components of the hybrid pulse compression RF systems 105A-105F is described below with respect to FIG. 19.

Techniques for Generating the Enhanced Waveform

In earlier iterations, a structured random permutation waveform was disclosed in which a random permutation of a sinusoidal pulse was taken to form the structured random permutation waveform. Additional details of the structured random permutation waveform can be found in U.S. Pat. No. 8,747,321, entitled "STRUCTURED RANDOM PERMUTATION PULSE COMPRESSION SYSTEMS AND METHODS" and filed on Oct. 22, 2012 (referred to herein as the "'321 patent"), which is hereby incorporated by reference herein in its entirety. The '321 patent further disclosed that the same random permutation process could be applied to the LFM signal. The structured random permutation waveform exhibited a better matched filter response than a generic LFM waveform. However, the structured random permutation waveform had to be bandlimited because the waveform spread the spectrum to the maximum possible spectral range, including beyond standard RADAR bandwidths. The band limiting, though, may have eliminated some advantages of the structured random permutation waveform over the generic LFM waveform.

Accordingly, disclosed herein is the enhanced waveform, which is a partial randomization of the LFM waveform that exhibits improvements over the generic LFM waveform. The enhanced waveform is also referred to herein as a variable spread spectrum because the waveform limits spectral spreading. The process by which the multi-waveform signal generator 110A and/or the enhanced waveform signal generator 111B generate the enhanced waveform is described below.

Figure 2:
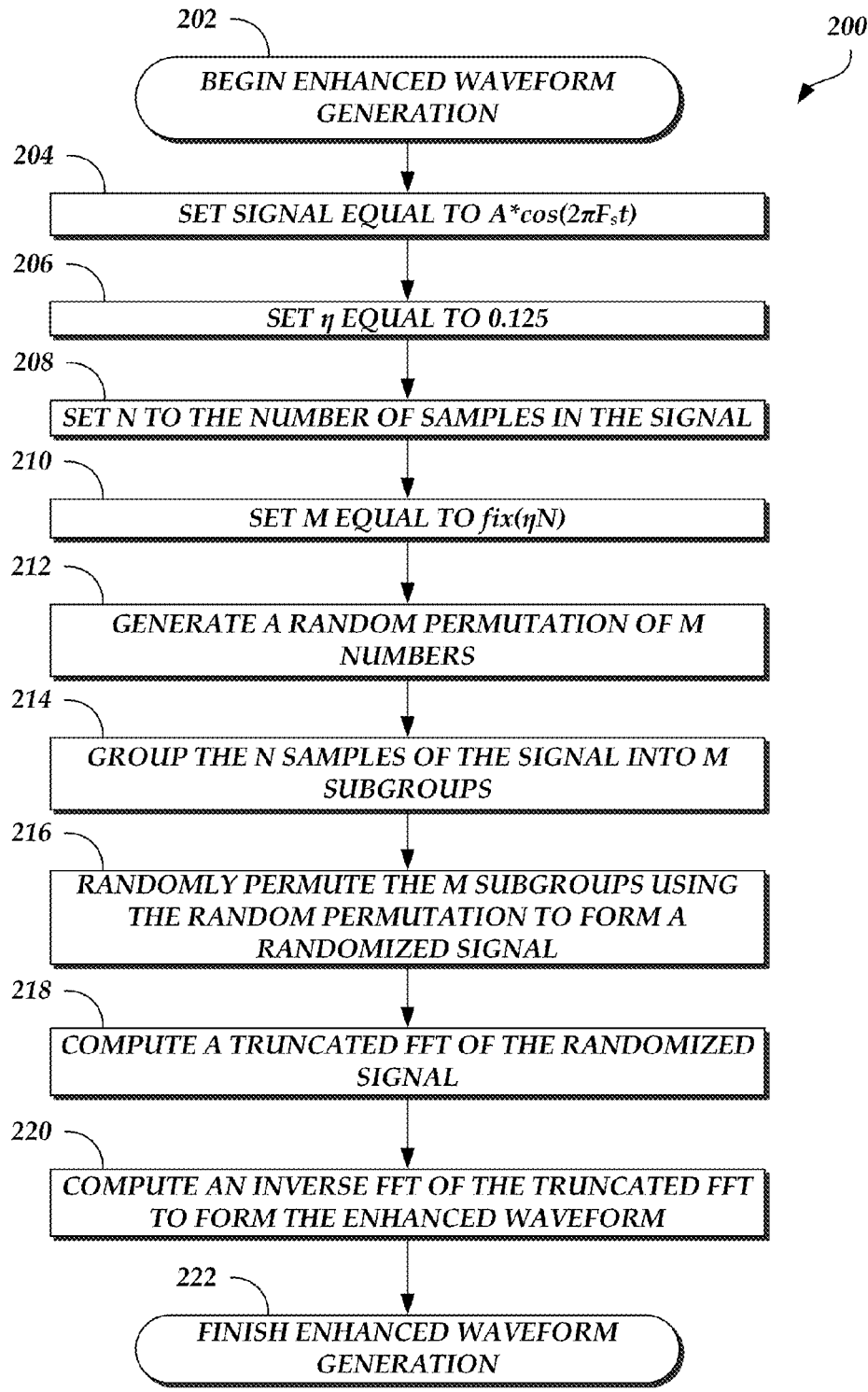
FIG. 2 is a flow diagram depicting an enhanced waveform generation routine illustratively implemented by the multi-waveform signal generator or the enhanced waveform signal generator of FIGS. 1A-1F.

FIG. 2 is a flow diagram depicting an enhanced waveform generation routine 200 illustratively implemented by a multi-waveform signal generator or an enhanced waveform signal generator. As an example, the multi-waveform signal generator 110A or the enhanced waveform signal generator 111B of FIGS. 1A-1F can be configured to execute the enhanced waveform generation routine 200. The enhanced waveform generation routine 200 begins at block 202.

At block 204, a signal s(t) is set equal to A*cos(2πF$_s$t). As an example, F$_s$ may be defined by the sampling rate T$_s$ as $$F_s = \frac{1}{2T_s}.$$

In some embodiments, the signal s(t) is the LFM waveform. In other embodiments, the signal s(t) is another poly-phase code waveform, such as a Gold code waveform or a Barker code waveform, another RADAR waveform, a generic noise waveform, a SONAR waveform, a LIDAR waveform, an MRI waveform, and ultrasound waveform, a CT waveform, and/or the like. The signal s(t) may be the poly-phase code waveform that is generated by the signal generator 110A and/or 111A.

At block 206, the variable η, which represents the partial randomization index, is set equal to 0.125. While a specific value for the variable η is provided herein, this is merely for illustrative purposes and is not meant to be limiting. The partial randomization index can be any value between 0 and 1.

At block 208, the variable N is set equal to the number of samples in the signal s(t). Thus, the product NT$_s$ may define the length of the LFM or chirp waveform.

At block 210, the variable M is set equal to the function fix(ηN). For example, the function fix may remove the fractional part of an inputted number and return the resulting integer value.

At block 212, a random permutation of M numbers is generated. The random permutation of the M numbers may be defined as RPT$_M$.

At block 214, the N samples of the signal s(t) are grouped into M subgroups. As an example, each M subgroup may include 8 samples. The grouped N samples may form a bandlimited noise waveform.

At block 216, the M subgroups are randomly permuted using the random permutation (e.g., RPT$_M$) to form a randomized signal. The randomized signal may be referred to as s$_n$.

At block 218, a truncated fast Fourier transform (FFT) of the randomized signal is computed. For example, the allowed bandwidth of the signal s(t) may be −ω to ω. A FFT of the randomized signal can be computed and the Fourier coefficients outside the range of −ω to ω can be set to zero to result in a truncated FFT of the randomized signal.

At block 220, an inverse FFT of the truncated FFT is computed to form the enhanced waveform. The inverse FFT of the truncated FFT may be referred to as signal s$_c$. Signal s$_c$ may be the bandlimited partially randomized LFM waveform or the enhanced waveform. After the inverse FFT of the truncated FFT is computed, the enhanced waveform generation routine 200 may be complete, as shown at block 222.

Mathematical Theory of the Enhanced Waveform

As described above, a random permutation of M numbers can be generated and the N samples, which are grouped into different M subgroups, can be randomly permuted using the random permutation. The randomization invoked through the random permutation transform of length N (e.g., there are N samples collectively in the M subgroups) can be modeled as N coherent narrowband Gaussian LFM pulses with random frequencies and phase shifts. F$_c$ can represent the center frequency, T can be the pulse width, B can be the LFM bandwidth, $$\beta = \frac{F_s}{B}$$

can be the LFM modulation index, and F$_s$ can be the sampling rate. The ambiguity function can then be approximated as follows:

$$AF(\tau, v) = \left(1 - \left(\frac{\tau}{T}\right)\right)\left(\frac{\sin\alpha}{\alpha}\right)\left(\frac{\sin(M\pi T r)}{\sqrt{M}\sin(\pi v T_r)}\right) \quad (1)$$

where $$\alpha = \pi F_{ct}\left(v \pm \beta\left(\frac{\tau}{T}\right)\right),$$

η is the partial randomization factor, M=fix(ηN), and A is the amplitude of the ambiguity function. If η equals 1, then the ambiguity function corresponds to 100% randomization.

Likewise, if η equals 1/N, then the ambiguity function corresponds to no randomization.

When M equals 1, the ambiguity function of equation (1) becomes the traditional expression for the ambiguity function of the LFM. When β equals 0, the ambiguity function of equation (1) becomes the ambiguity function of the enhanced waveform described herein. When both M equals 1 and β equals 0, the ambiguity function of equation (1) becomes the ambiguity function of a sinusoidal pulse.

The range profile for the LFM may be as follows:

$$AFLFM(\tau, 0) = \left(1 - \left(\frac{\tau}{T}\right)\right)\left(\frac{\sin\left(\frac{\pi\beta\tau}{T}\right)}{\left(\frac{\pi\beta\tau}{T}\right)}\right) \quad (2)$$

The Doppler profile for the LFM may be as follows:

$$AFLFM(0, v) = \frac{\sin(\pi T v)}{\pi T v} \quad (3)$$

Similarly, the range profile for the enhanced waveform may be as follows:

$$AFEnhanced(\tau, 0) = \delta(\tau) + \frac{\sin\left(\frac{\pi\tau}{T}\right)}{\sqrt{M}\left(\frac{\pi\tau}{T}\right)} \quad (4)$$

and the Doppler profile for the enhanced waveform may be as follows:

$$AFEnhanced(0, v) = \left(\frac{1}{\sqrt{M}}\right)\left(\frac{\sin(\pi T v)}{\pi T v}\right) \quad (5)$$

Techniques for Detecting a Target Using the Enhanced Waveform

Figure 3:
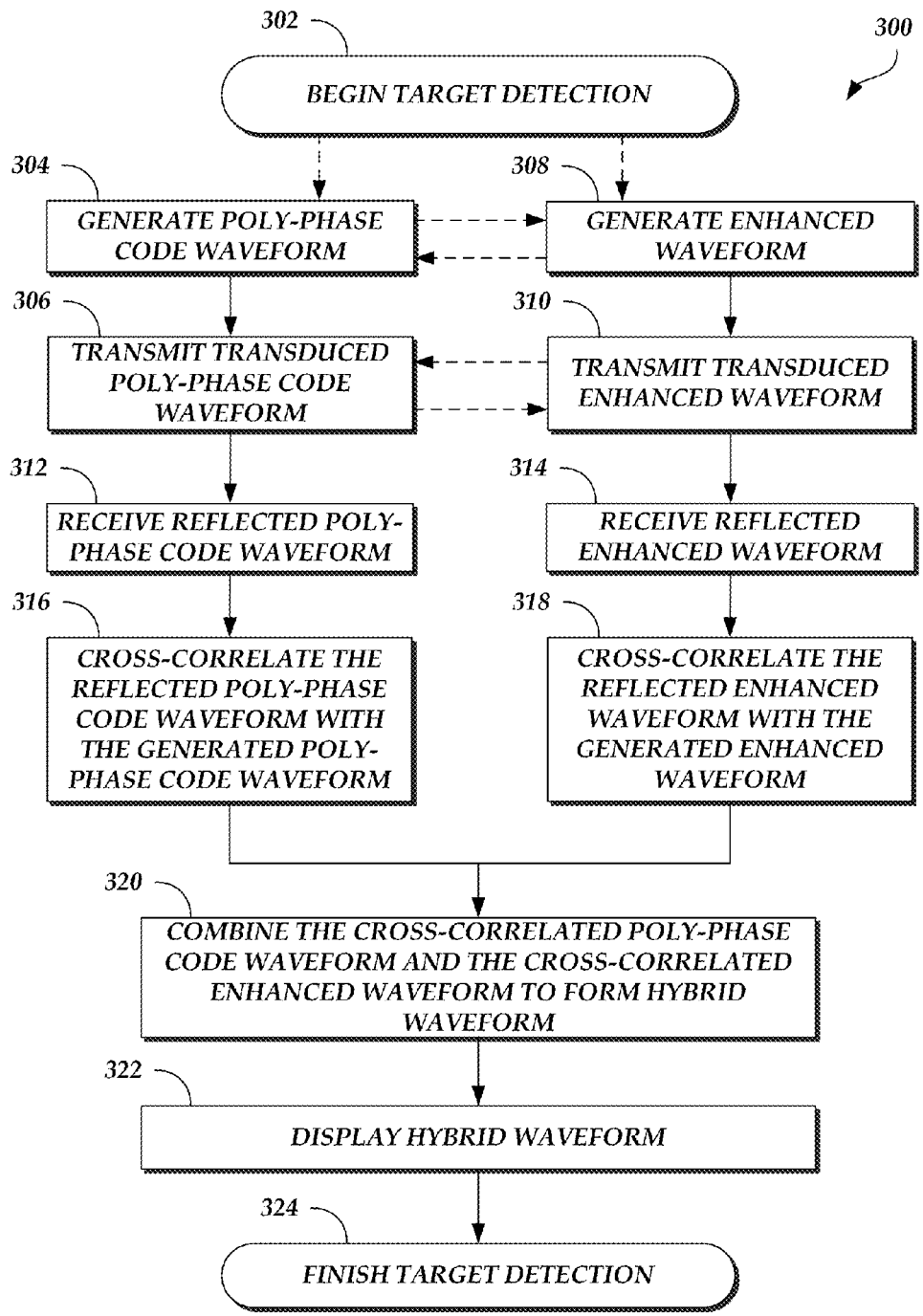
FIG. 3 is a flow diagram depicting a target detection routine illustratively implemented by a hybrid pulse compression RF system.

FIG. 3 is a flow diagram depicting a target detection routine 300 illustratively implemented by a hybrid pulse compression RF system. As an example, the hybrid pulse compression RF systems 105A-105E of FIGS. 1A-1E can be configured to execute the target detection routine 300. The target detection routine 300 begins at block 302.

At block 304, a poly-phase code waveform is generated. For example, the poly-phase code waveform that is generated may be an LFM waveform, a Gold code waveform, a Barker code waveform, a noise waveform, and/or the like.

At block 306, a transduced version of the poly-phase code waveform is transmitted. For example, the poly-phase code waveform may be converted into a form (e.g., an electromagnetic field, an acoustic signal, a radio signal, an optical signal, an ultrasound signal, a microwave signal, an X-RAY signal, a laser, etc.) that can be transmitted through a medium (e.g., air, water, etc.). The transduced version of the poly-phase code waveform may be transmitted in a direction in which a target may or may not be present.

At block 308, the enhanced waveform is generated. The enhanced waveform may be generated using the techniques discussed above with respect to FIG. 2.

At block 310, a transduced version of the enhanced waveform is transmitted. For example, like with the poly-phase code waveform, the enhanced waveform may be converted into a form that can be transmitted through a medium. The transduced version of the enhanced waveform may be transmitted in a direction in which a target may or may not be present.

In an embodiment, the target detection routine 300 performs block 304 first, followed by blocks 308, 306, and 310 in order. In other embodiments, the target detection routine 300 performs block 308 first, followed by blocks 304, 310, and 306 in order. In still other embodiments, the target detection routine 300 may perform blocks 304 and 308 simultaneously or nearly simultaneously, followed by blocks 306 and 310 in order or blocks 310 and 306 in order. Thus, the hybrid pulse compression RF system 105A-105E may generate the LFM waveform and the enhanced waveform in a particular sequence, simultaneously, or nearly simultaneously. The hybrid pulse compression RF system 105A-105E may then transmit transduced versions of the generated waveforms in a particular order.

At block 312, a reflected poly-phase code waveform is received. For example, the transmitted LFM waveform may reflect off a target 140 and be captured by a receiver 150.

At block 314, a reflected enhanced waveform is received. For example, the transmitted enhanced waveform may reflect off a target 140 and be captured by a receiver 150.

The target detection routine 300 performs block 312 before block 314 if the LFM waveform is transmitted before the enhanced waveform. Otherwise, if the LFM waveform is transmitted after the enhanced waveform, then the target detection routine 300 performs block 312 after block 314.

At block 316, the reflected poly-phase code waveform is cross-correlated with the generated poly-phase code waveform. At block 318, the reflected enhanced waveform is cross-correlated with the generated enhanced waveform. The target detection routine 300 may perform blocks 316 and 318 simultaneously (e.g., in parallel) or in any sequence. The hybrid pulse compression RF system 105A-105E may determine that a received reflected waveform is the LFM waveform or the enhanced waveform based on whether a previous waveform is received by the receiver and the order in which the waveforms were transmitted. For example, if the LFM waveform is transmitted first, the receiver 150 detects a reflected waveform, and the receiver 150 has not previously detected a reflected waveform (since the last pair of reflected LFM and enhanced waveforms was detected), then the hybrid pulse compression RF system 105A-105E determines that the received reflected waveform is a reflected LFM waveform.

At block 320, the cross-correlated poly-phase code waveform and the cross-correlated enhanced waveform are combined to form a hybrid waveform. For example, the hybrid pulse compression RF system 105A-105E can take a product of the cross-correlated poly-phase code waveform and the cross-correlated enhanced waveform to form the hybrid waveform. In further embodiments, the hybrid pulse compression RF system 105A-105E further generates statistical data corresponding to the hybrid waveform.

Figure 17:
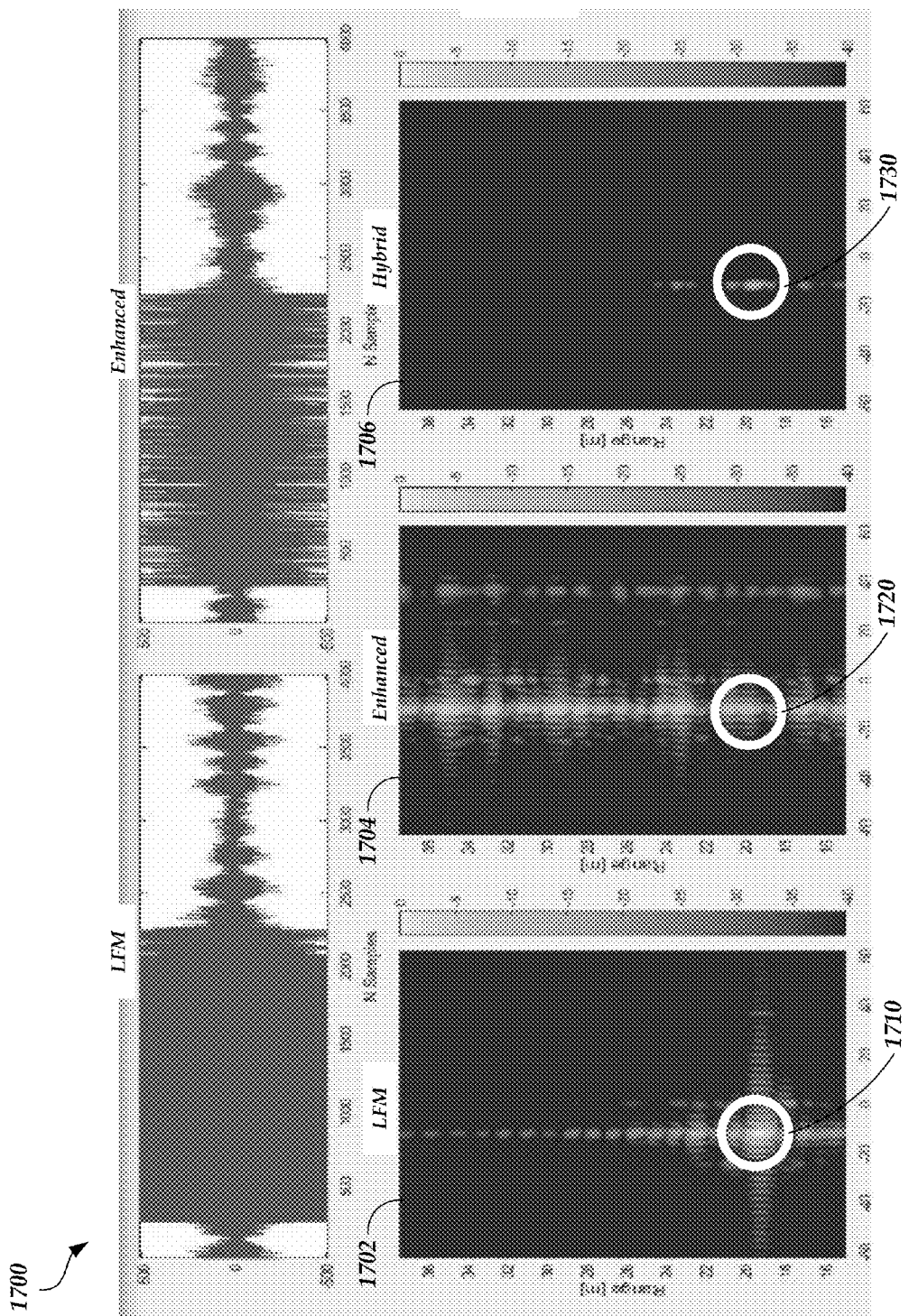
FIG. 17 illustrates a graph depicting a frame from three range-Doppler movies or animations that are created by a hybrid pulse compression RF system of FIGS. 1A-1F as a result of receiving reflected waveform(s).
Figure 18:
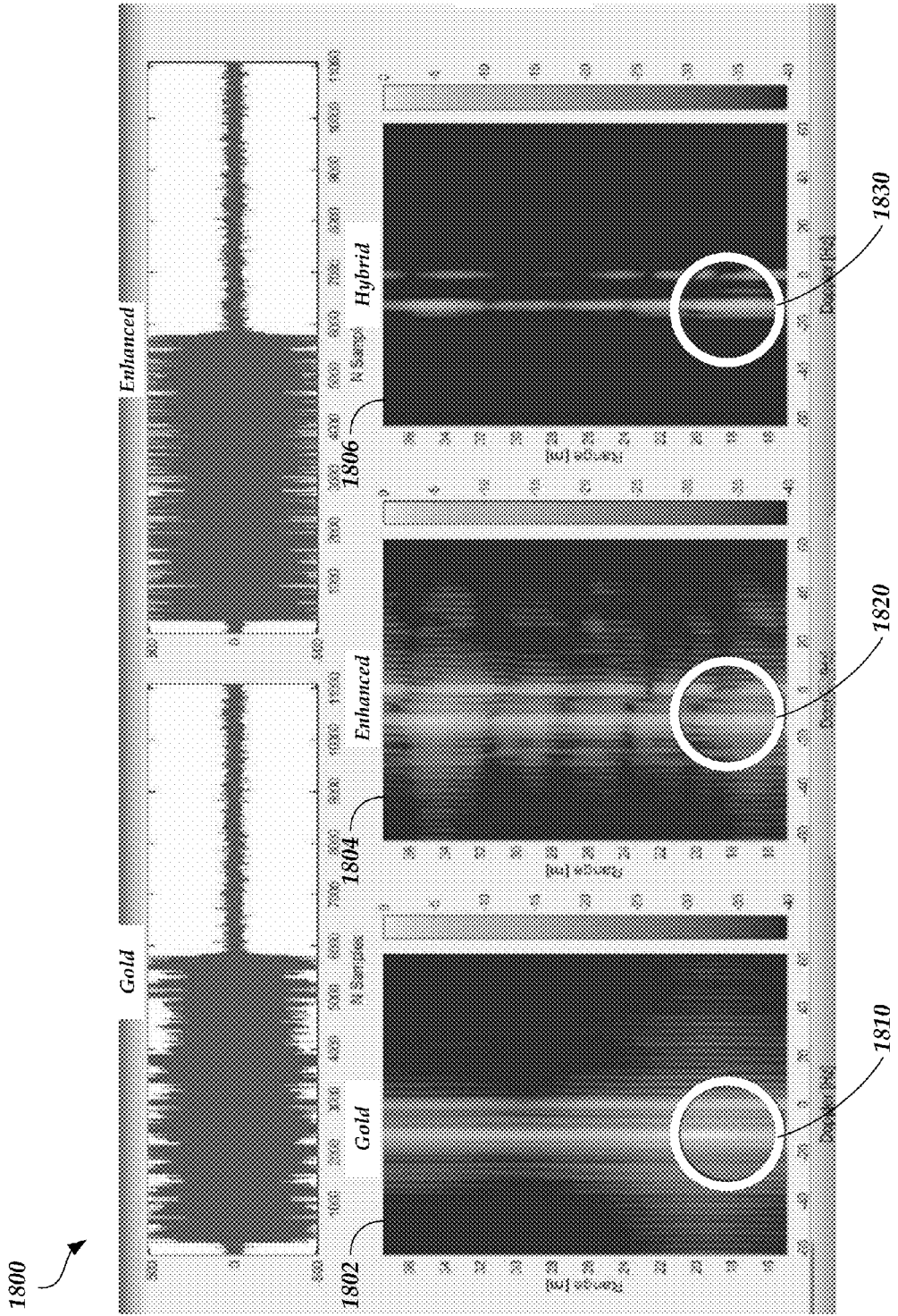
FIG. 18 illustrates a graph depicting a frame from three range-Doppler movies or animations that are created by a hybrid pulse compression RF system of FIGS. 1A-1F as a result of receiving reflected waveform(s).

At block 322, the hybrid waveform is displayed. For example, the hybrid waveform and/or the generated statistical data can be transmitted to an internal or external display such that the hybrid waveform and/or the generated statistical data can be presented in a user interface for viewing by a user. The hybrid waveform, when visually represented in a user interface, may indicate whether a target was detected and/or a possible location, shape, and/or size of the detected target. FIGS. 17 and 18 provide examples of displayed hybrid waveforms, as described below. As the hybrid pulse compression RF system 105A-105E continues to generate and transmit the LFM and enhanced waveforms and process the reflections to produce the hybrid waveform over time, the user interface may be periodically updated automatically to reflect changes in the hybrid waveform. After the hybrid waveform is displayed, the target detection routine 300 is complete, as shown at block 324.

Mathematical Theory of the Hybrid Waveform

In an embodiment, because the hybrid waveform is defined as the product of the LFM and enhanced waveforms, the ambiguity function of the hybrid waveform can be mathematically defined as the product of the mathematical expression of the ambiguity function of the LFM waveform and the mathematical expression of the ambiguity function of the enhanced waveform. For example, the ambiguity function of the hybrid waveform can be defined as follows:

$$AFHybrid(\tau, v) = \left(\frac{1}{\sqrt{M}}\right)\left(1-\left(\frac{\tau}{T}\right)\right)\left(\frac{\sin^2\alpha}{\alpha^2}\right)\left(\frac{\sin(M\pi v Tr)}{M\sin(\pi v Tr)}\right) \quad (6)$$

where $$\alpha = \pi\tau\left(v \pm \beta\left(\frac{\tau}{T}\right)\right),$$

$\eta$ is the partial randomization factor and $M=\eta N$.

The range profile for the hybrid waveform may be as follows:

$$AFHybrid(\tau, 0) = \left(\frac{1}{\sqrt{M}}\right)\left(1-\frac{\tau}{T}\right)\left(\frac{\sin\left(\frac{\pi\beta\tau}{T}\right)}{\left(\frac{\pi\beta\tau}{T}\right)}\right)\left(\delta(\tau) + \frac{\sin\left(\frac{\pi\tau}{T}\right)}{M\left(\frac{\pi\tau}{T}\right)}\right) \quad (7)$$

and the Doppler profile for the hybrid waveform may be as follows:

$$AFHybrid(0, v) = \left(\frac{1}{\sqrt{M}}\right)\left(\frac{\sin(\pi T v)}{\pi T v}\right)\left(\frac{\sin(\pi T v)}{\pi T v}\right) \quad (8)$$

Comparison of Enhanced and Hybrid Waveforms with Conventional Waveforms

Figure 4:
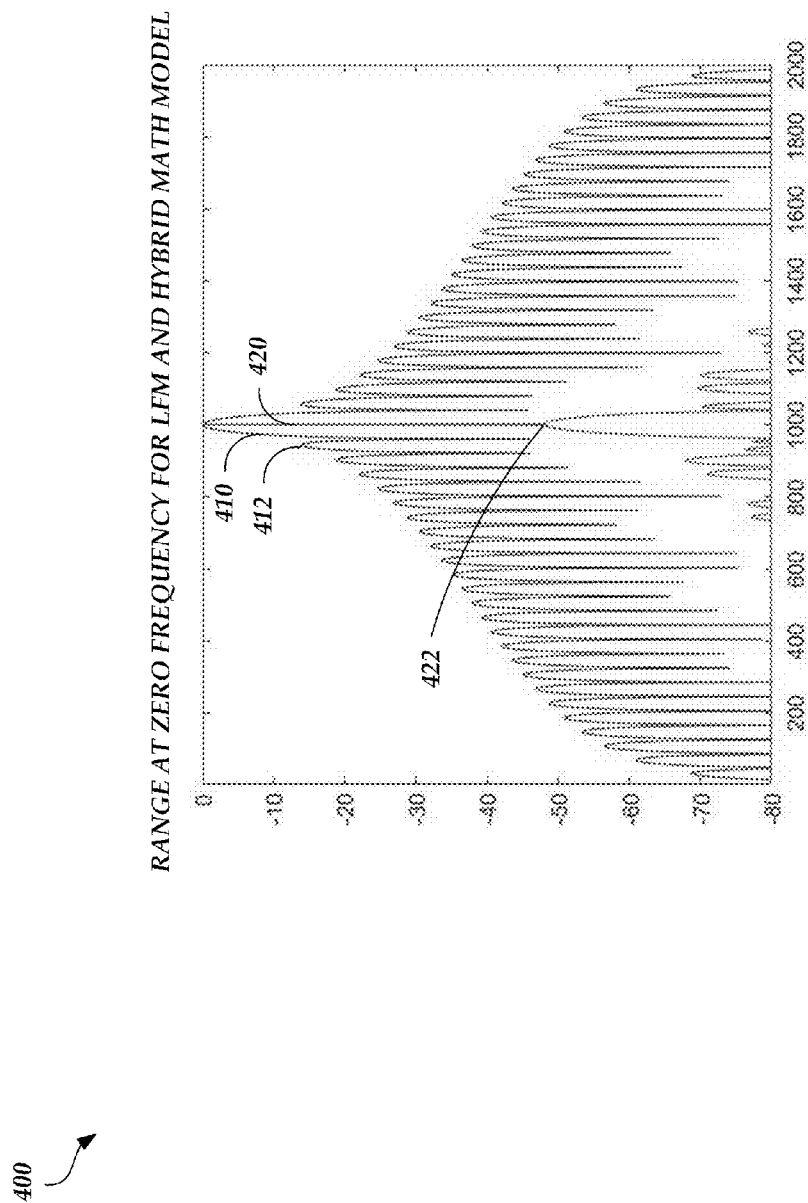
FIG. 4 illustrates a graph depicting an LFM range plot and a hybrid waveform range plot at zero Doppler.

FIG. 4 illustrates a graph 400 depicting an LFM range plot 410 and a hybrid waveform range plot 420 at zero Doppler. As illustrated in FIG. 4, a side lobe 422 of the hybrid waveform range plot 420 is at least −35 dB lower than a side lobe 412 of the LFM range plot 410.

Figure 5:
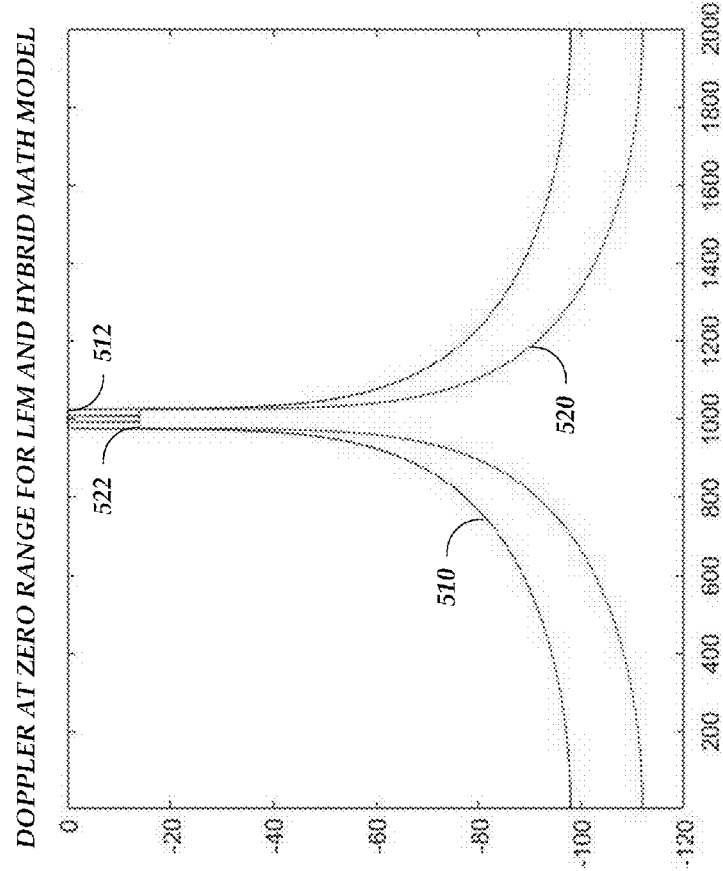
FIG. 5 illustrates a graph depicting an LFM Doppler plot and a hybrid waveform Doppler plot at zero range.

FIG. 5 illustrates a graph 500 depicting an LFM Doppler plot 510 and a hybrid waveform Doppler plot 520 at zero range. As illustrated in FIG. 5, a side lobe 522 of the hybrid waveform Doppler plot 520 is consistently approximately −15 dB lower than a side lobe 512 of the LFM Doppler plot 510.

Figure 6A:
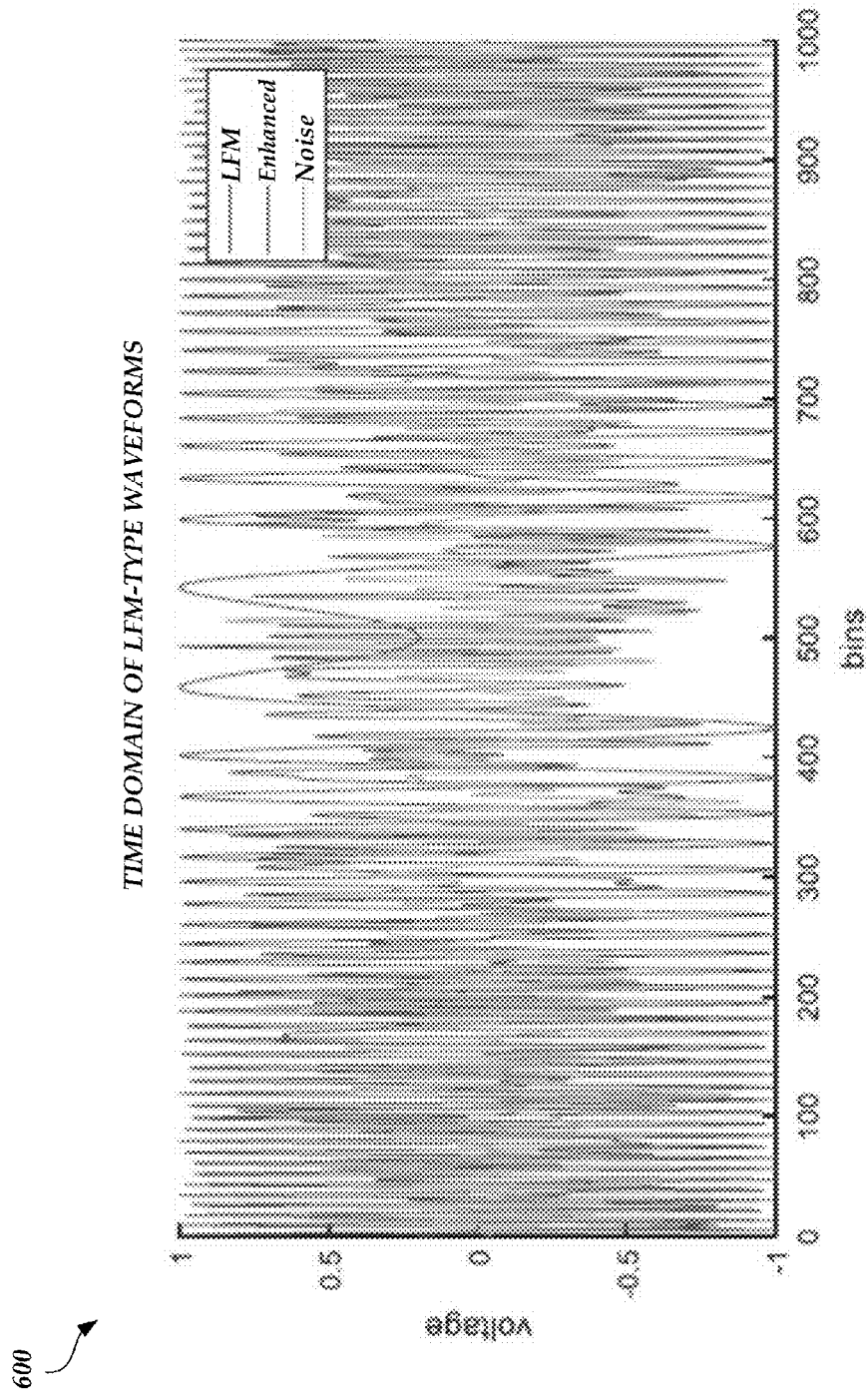
FIG. 6A illustrates a graph depicting the time domain signal of an LFM waveform, the enhanced waveform, and a typical pseudorandom noise waveform.

FIG. 6A illustrates a graph 600 depicting the time domain signal of an LFM waveform, the enhanced waveform, and a typical pseudorandom noise waveform. As illustrated in FIG. 6A, the amplitude (as measured in voltage) of the enhanced waveform and the typical pseudorandom noise waveform vary less than the amplitude of the LFM waveform when considering all bins. For example, the amplitude of the enhanced waveform and/or the typical pseudorandom noise waveform generally ranges from approximately 0.75V to −0.75V. However, the amplitude of the LFM waveform generally ranges from approximately 1V to −1V.

Figure 6B:
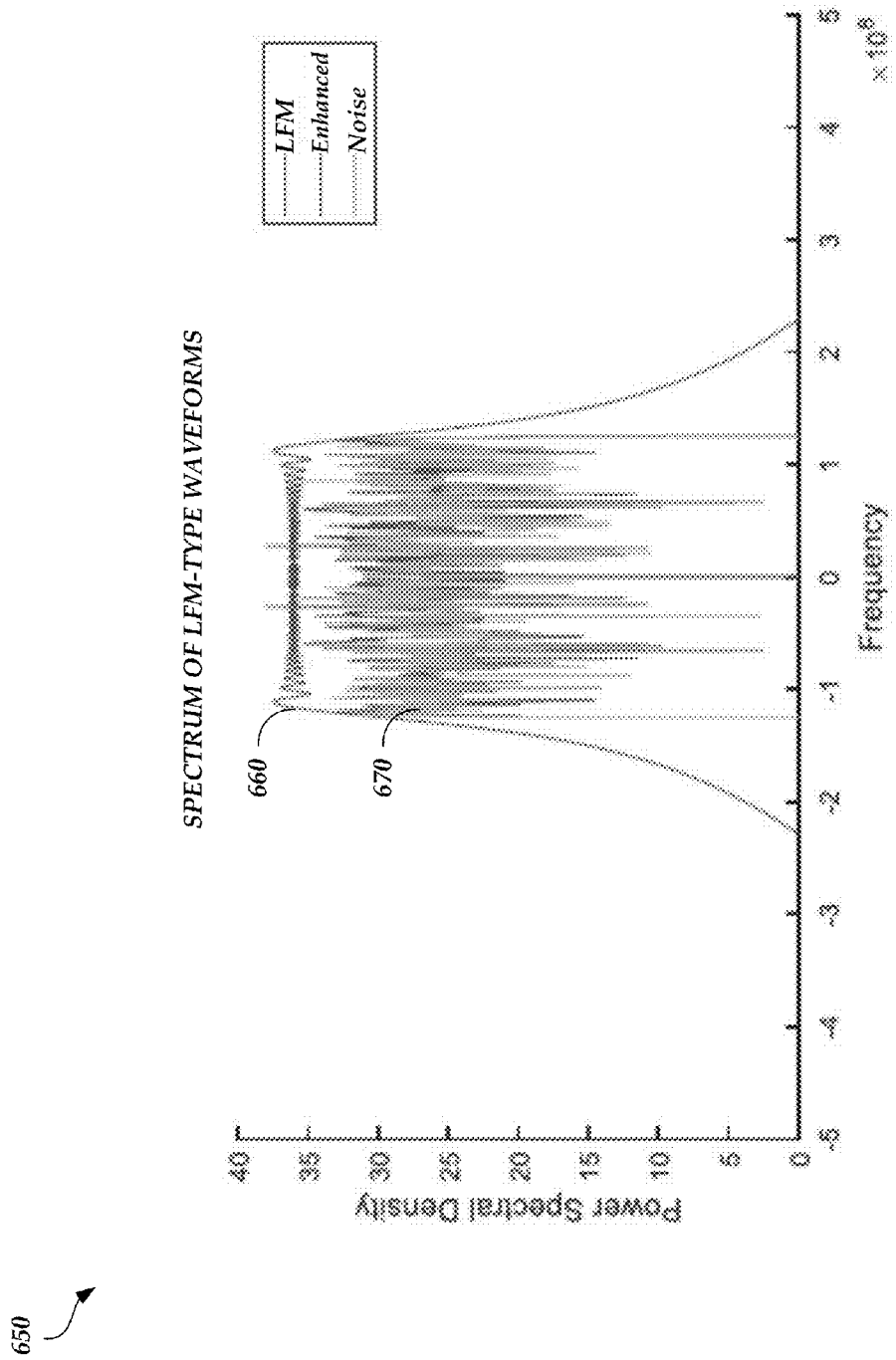
FIG. 6B illustrates a graph depicting the spectrum signal of an LFM waveform, an enhanced waveform, and a typical pseudorandom noise waveform.

FIG. 6B illustrates a graph 650 depicting the spectrum signal of an LFM waveform 660, an enhanced waveform 670, and a typical pseudorandom noise waveform. As illustrated in FIG. 6B, the power spectral density of the enhanced waveform 670 and the typical pseudorandom noise waveform generally range from approximately 20 to 35 for various frequencies. The power spectral density of the LFM waveform 660 exhibits oscillating behavior, generally ranging from approximately 35 to 37 for various frequencies.

Figure 7:
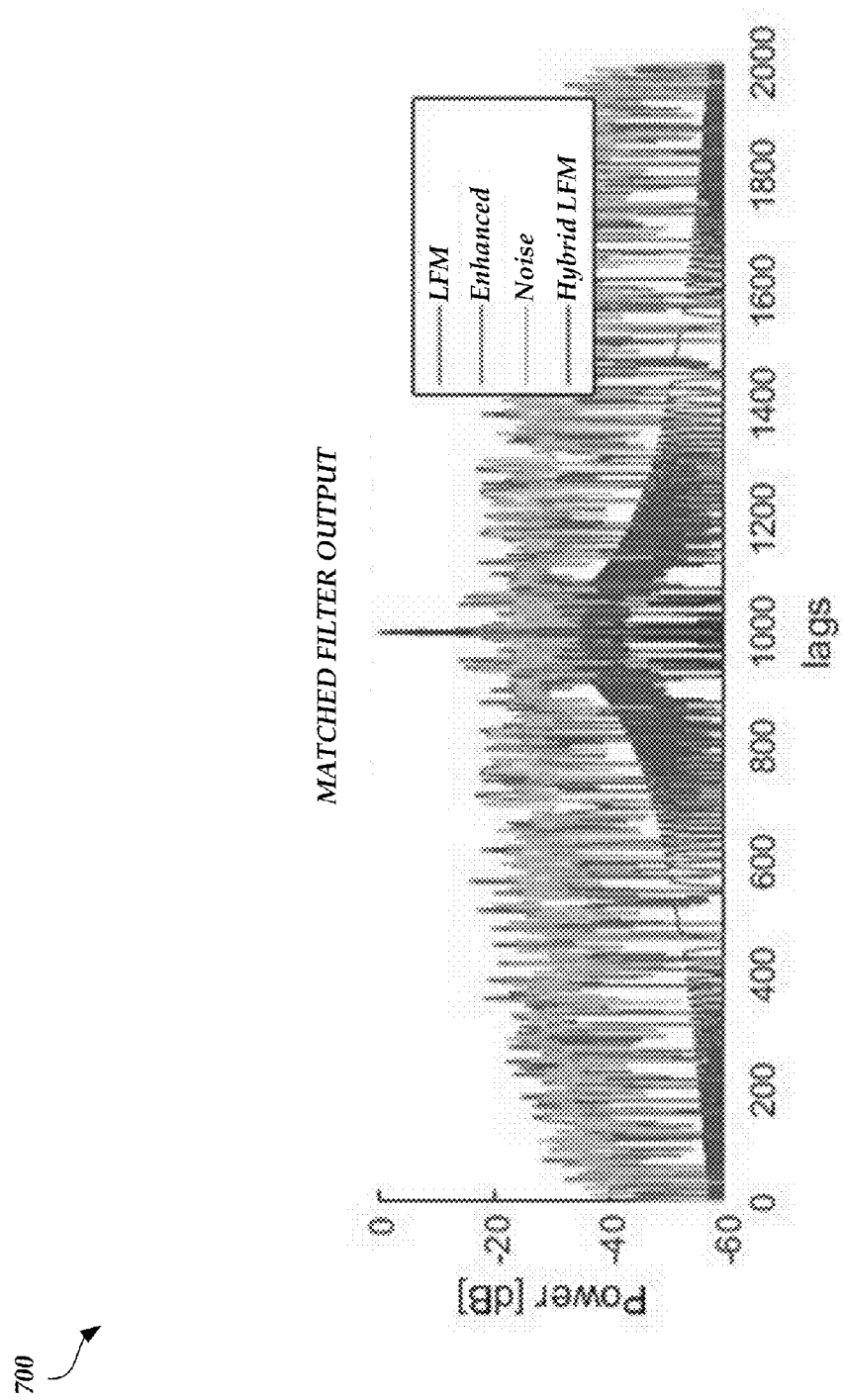
FIG. 7 illustrates a graph depicting the response of the poly-phase code waveform matched filter, the response of the enhanced waveform matched filter, the response of a matched filter for a typical noise waveform, and the response of a matched filter for the hybrid LFM.

FIG. 7 illustrates a graph 700 depicting the response of the poly-phase code waveform matched filter 160A (e.g., a matched filter for an LFM waveform), the response of the enhanced waveform matched filter 160B, the response of a matched filter for a typical noise waveform, and the response of a matched filter for the hybrid LFM (as disclosed in the '321 patent). As illustrated in FIG. 7, the power of the response of the enhanced waveform matched filter 160B and the power of the response of the matched filter for a typical noise waveform have similar values across various lags. The power of the response of the LFM waveform matched filter 160A and the power of the response of the matched filter of hybrid LFM have similar values across various lags. Other than between approximately 900 and 1100 lags, the power of the response of the LFM waveform matched filter 160A and the power of the response of the matched filter of hybrid LFM have lower values than the corresponding power values for the enhanced waveform matched filter 160B and the matched filter of the typical pseudorandom noise waveform. Thus, the enhanced waveform exhibits superior performance over the LFM waveform and the hybrid LFM waveform. In some cases, the enhanced waveform also exhibits superior performance over the typical pseudorandom noise waveform as well.

Figure 8:
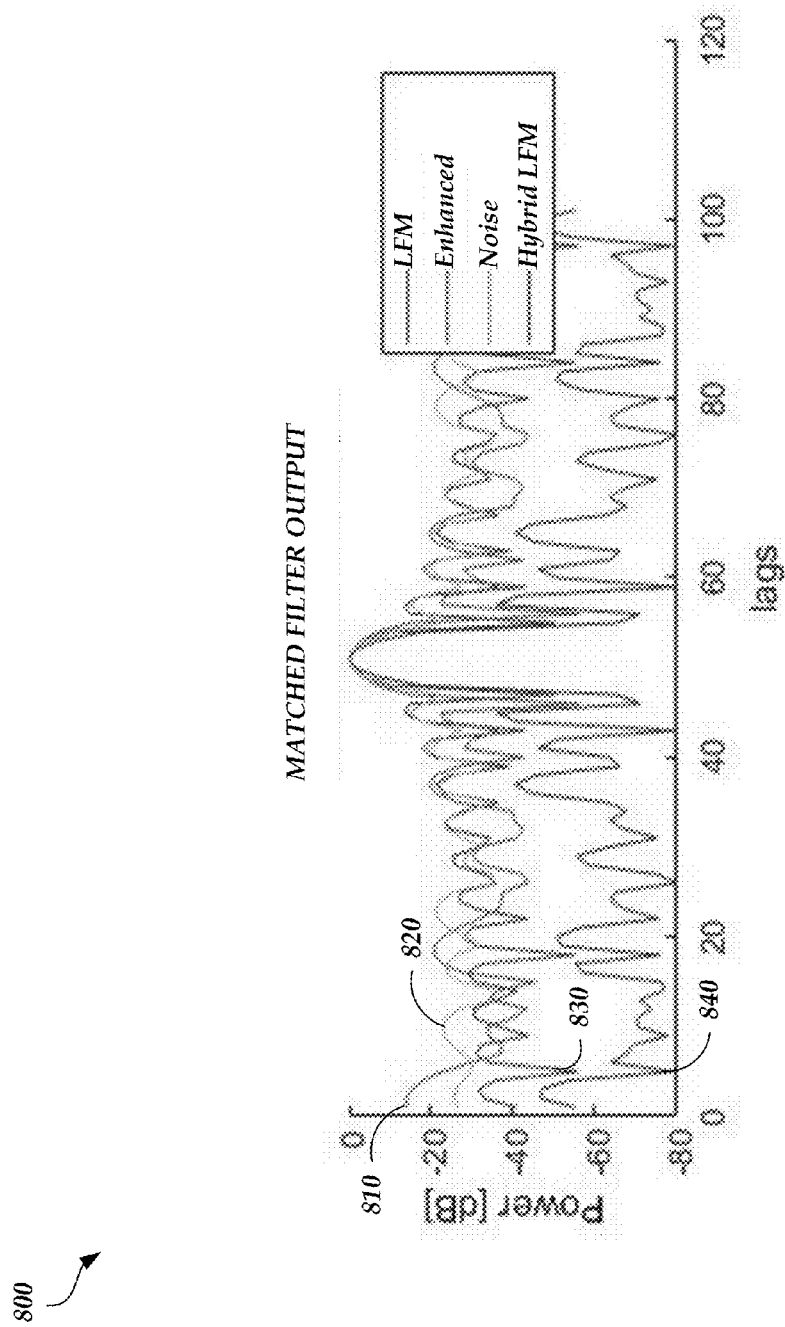
FIG. 8 illustrates a graph depicting a close-up view of a portion of the responses depicted in the graph of FIG. 7.

FIG. 8 illustrates a graph 800 depicting a close-up view of a portion of the responses depicted in the graph 700. As illustrated in FIG. 8, the enhanced waveform matched filter 160B response 810 exhibits superior performance in the near-field as well as at side lobes when compared with the matched filter response 820 of a typical pseudorandom noise waveform, the LFM waveform matched filter 160A response 830, and the matched filter response 840 of the hybrid LFM. For example, the response 810 is approximately 20 dB lower at the side lobes as compared with the response 830.

Figure 9A:
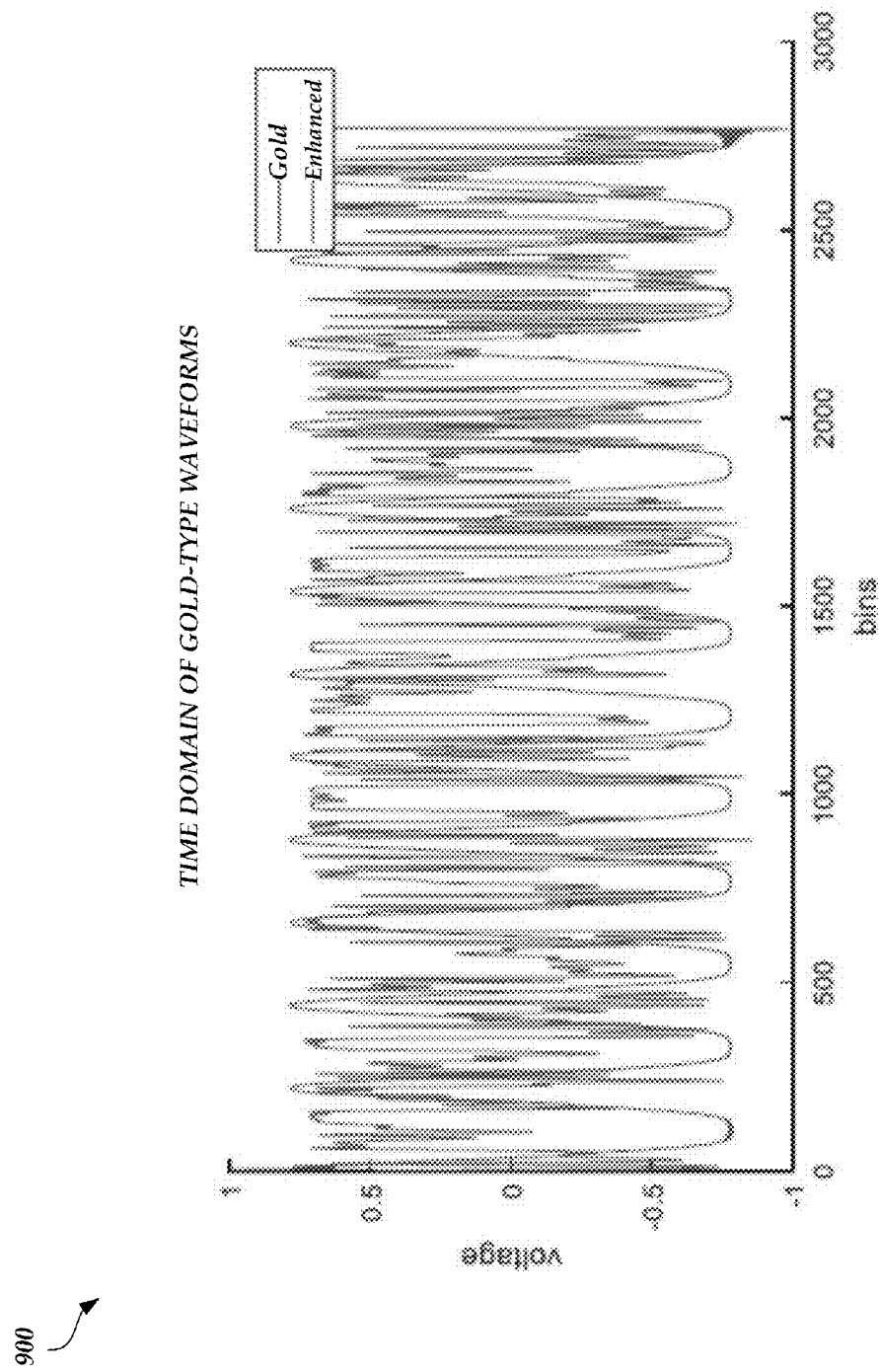
FIG. 9A illustrates a graph depicting the time domain signal of a Gold code waveform and the enhanced waveform.

Similarly, the enhanced waveform also exhibits superior performance as compared with a Gold code waveform. FIG. 9A illustrates a graph 900 depicting the time domain signal of a Gold code waveform and the enhanced waveform. As illustrated in FIG. 9A, the amplitude (as measured in voltage) of the enhanced waveform varies less than the amplitude of the Gold code waveform when considering all bins. For example, the amplitude of the enhanced waveform generally ranges from approximately 0.75V to −0.75V. The amplitude of the Gold code waveform generally ranges from approximately 0.8V to −0.8V.

Figure 9B:
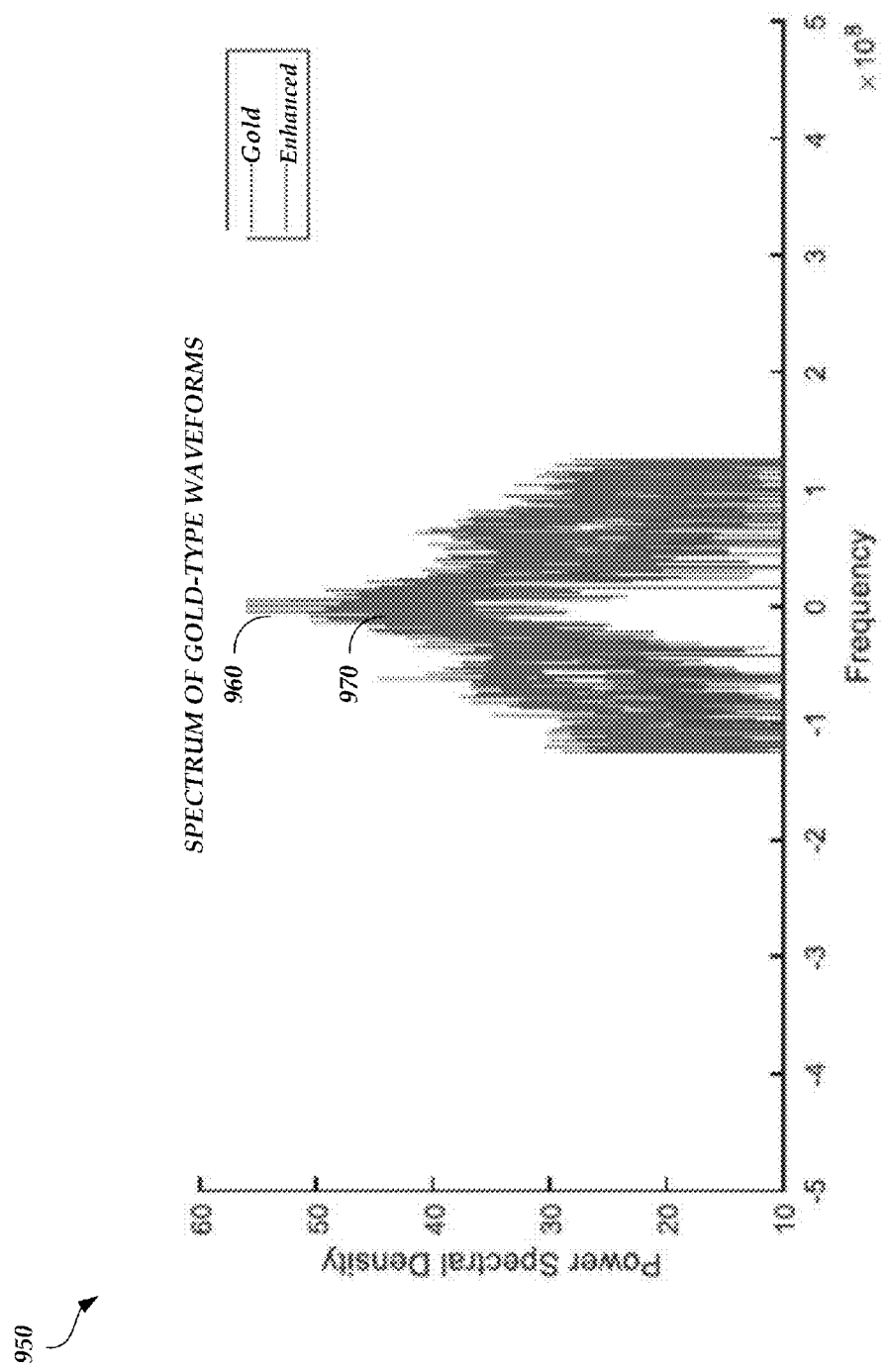
FIG. 9B illustrates a graph depicting the spectrum signal of a Gold code waveform and an enhanced waveform.

FIG. 9B illustrates a graph 950 depicting the spectrum signal of a Gold code waveform 960 and an enhanced waveform 970. As illustrated in FIG. 9B, the power spectral density of the enhanced waveform 970 is generally less than the power spectral density of the Gold code waveform 960 for various frequencies.

Figure 10:
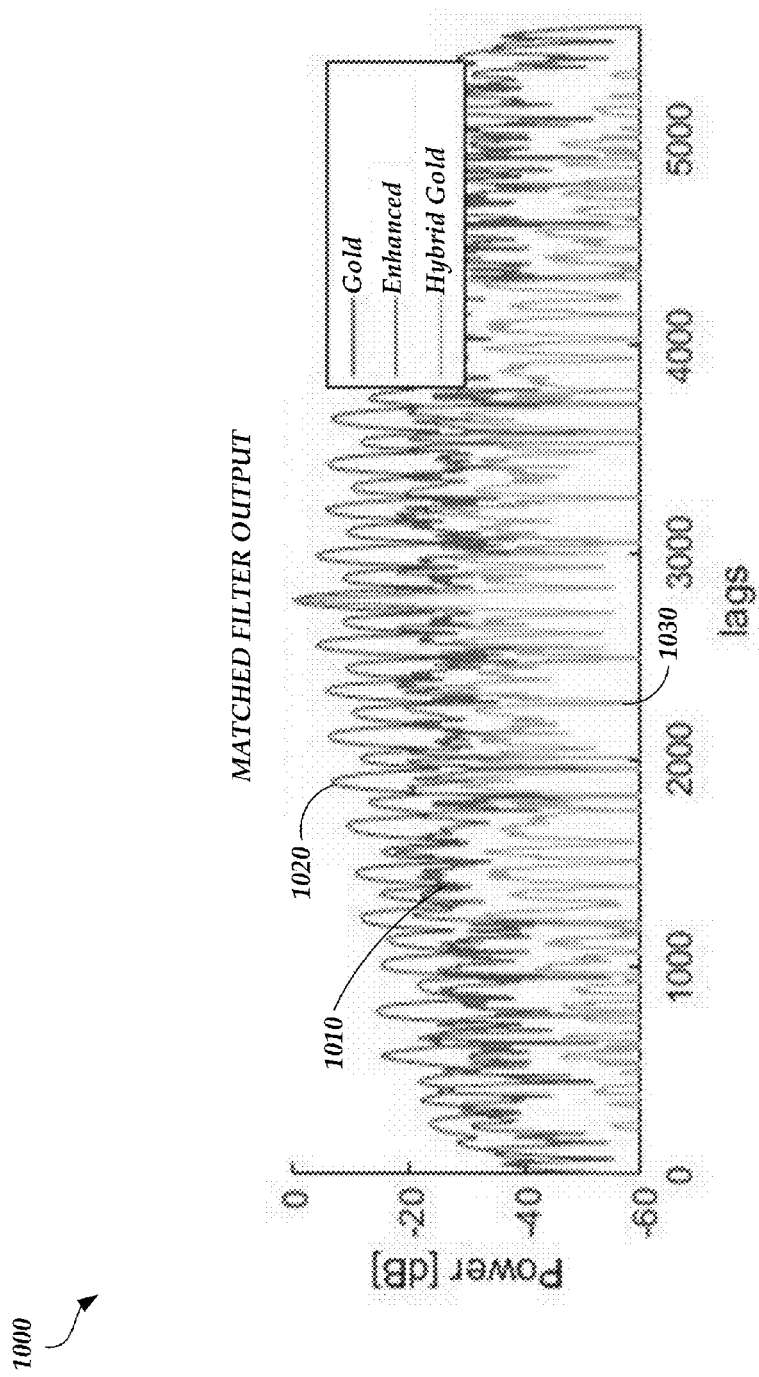
FIG. 10 illustrates a graph depicting the response of the poly-phase code waveform matched filter, the response of the enhanced waveform matched filter, and the response of a matched filter for a hybrid Gold code waveform.

FIG. 10 illustrates a graph 1000 depicting the response of the poly-phase code waveform matched filter 160A (e.g., a matched filter for a Gold code waveform), the response of the enhanced waveform matched filter 160B, and the response of a matched filter for a hybrid Gold code waveform (as disclosed in the '321 patent). As illustrated in FIG. 10, the power of the response 1010 of the enhanced waveform matched filter 160B falls generally between the power of the response 1020 of the Gold code waveform matched filter 160A and the power of the response 1030 of the matched filter for the hybrid Gold code waveform.

Figure 11:
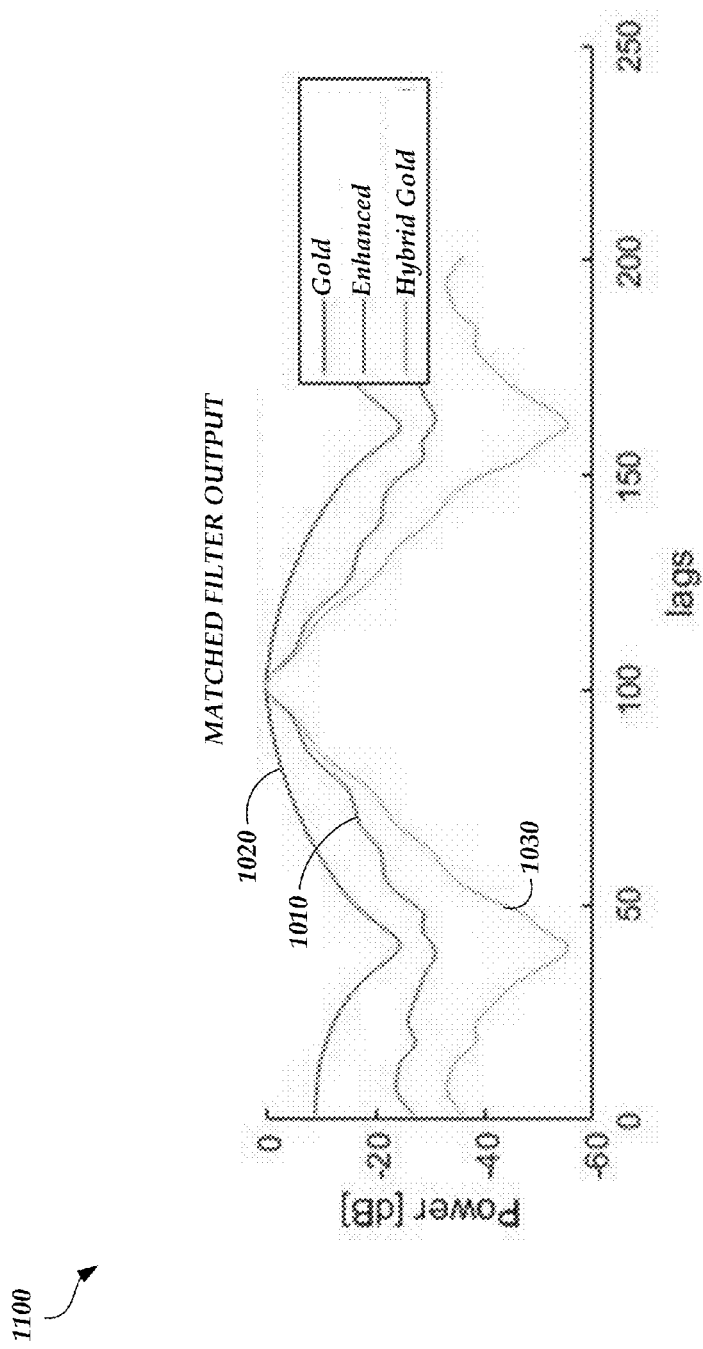
FIG. 11 illustrates a graph depicting a close-up view of a portion of the responses depicted in the graph of FIG. 10.

FIG. 11 illustrates a graph 1100 depicting a close-up view of a portion of the responses depicted in the graph 1000. As illustrated in FIG. 11, the enhanced waveform matched filter 160B response 1010 exhibits superior performance in the near-field as well as at side lobes when compared with the Gold code waveform matched filter 160A response 1020, and the matched filter response 1030 of the hybrid Gold code waveform.

Figure 12:
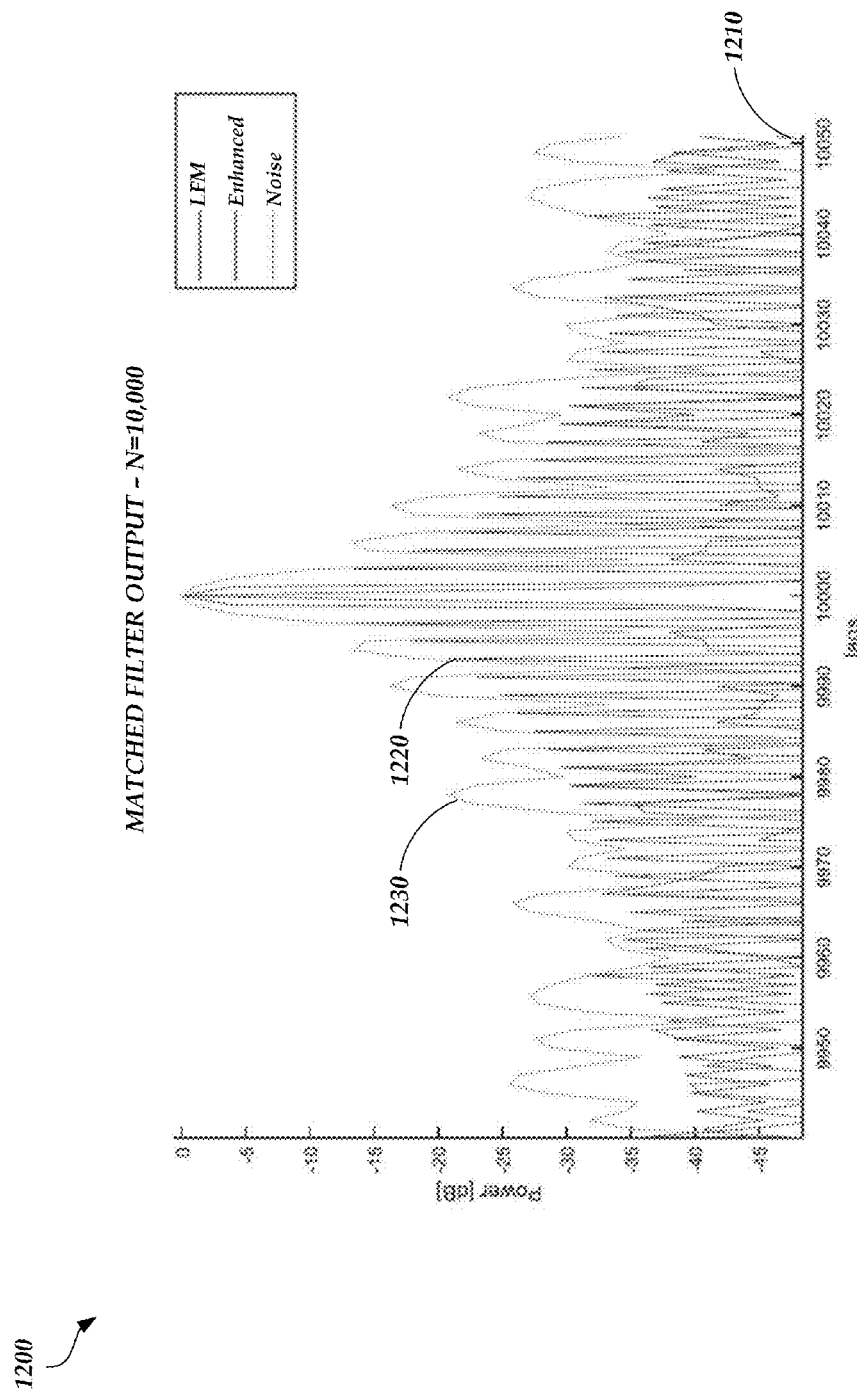
FIG. 12 illustrates a graph depicting the response of the poly-phase code waveform matched filter, the response of the enhanced waveform matched filter, and the response of the matched filter for a typical pseudorandom noise waveform when the number of samples is 10,000.
Figure 13:
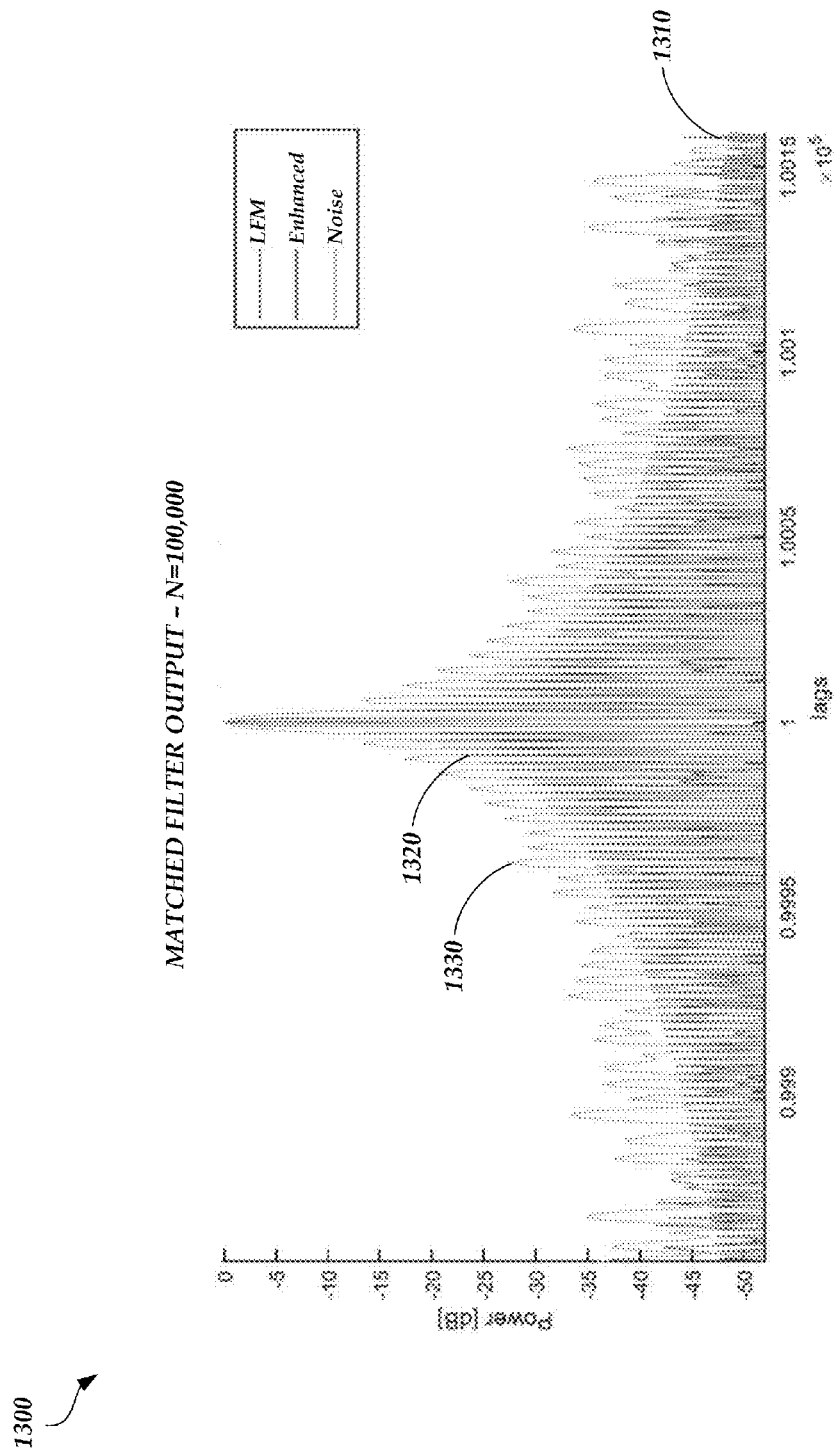
FIG. 13 illustrates a graph depicting the response of the poly-phase code waveform matched filter, the response of the enhanced waveform matched filter, and the response of the matched filter for a typical pseudorandom noise waveform when the number of samples is 100,000.

Varying the length of the LFM waveform may improve the matched filter response of the enhanced waveform near side lobes. Such varying of the length of the LFM waveform may otherwise have no effect on the LFM waveform and little to no effect on a typical noise waveform. For example, FIG. 12 illustrates a graph 1200 depicting the response 1220 of the poly-phase code waveform matched filter 160A (e.g., a matched filter for an LFM waveform), the response 1210 of the enhanced waveform matched filter 160B, and the response 1230 of the matched filter for a typical pseudorandom noise waveform when the number of samples is 10,000. As another example, FIG. 13 illustrates a graph 1300 depicting the response 1320 of the poly-phase code waveform matched filter 160A (e.g., a matched filter for an LFM waveform), the response 1310 of the enhanced waveform matched filter 160B, and the response 1330 of the matched filter for a typical pseudorandom noise waveform when the number of samples is 100,000.

Example Prototype Schematic

Figure 14A:
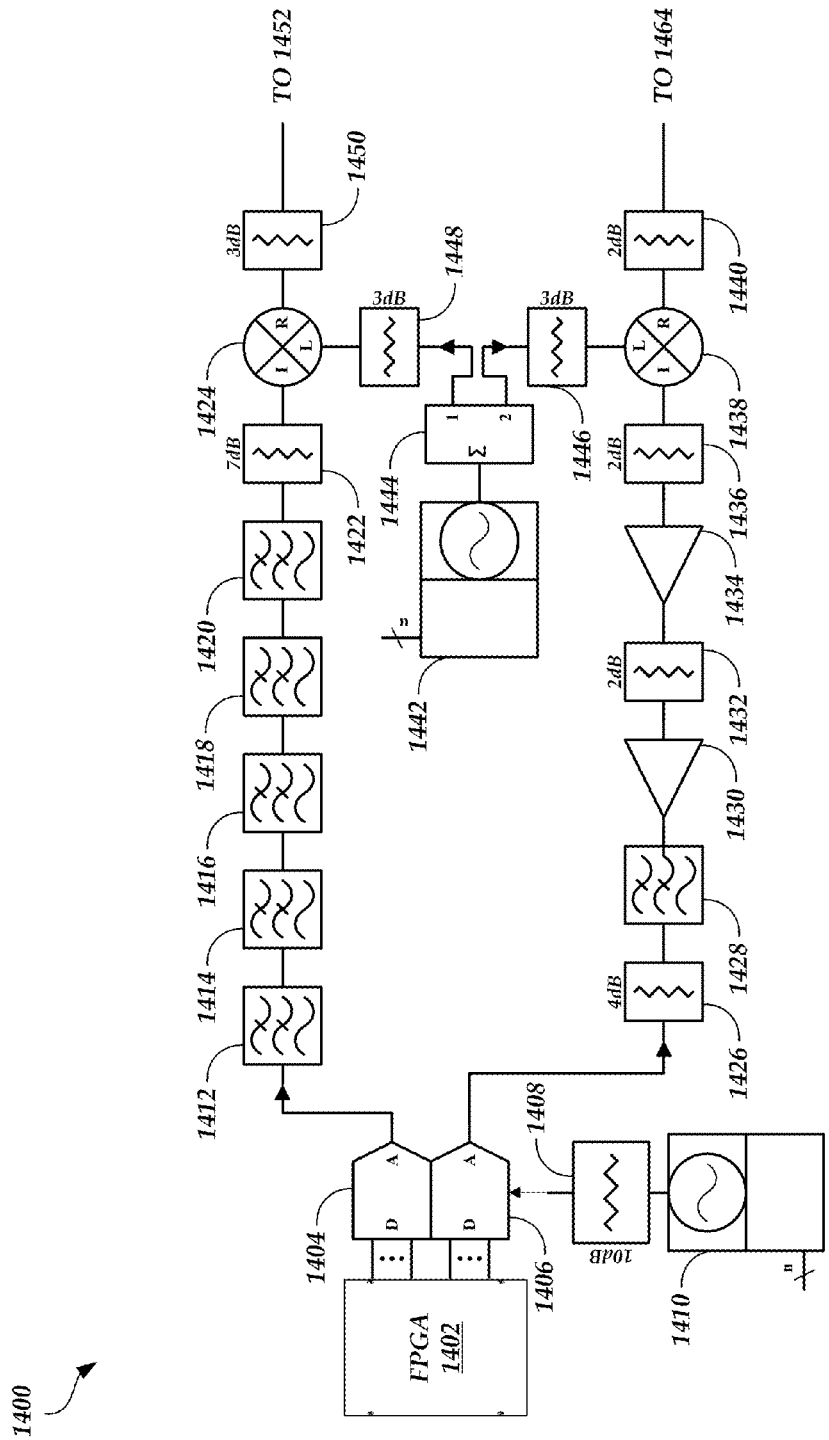
FIGS. 14A-14B illustrate a schematic of an exemplary RADAR system that generates and utilizes the enhanced waveform and the hybrid waveform described herein.
Figure 14B:
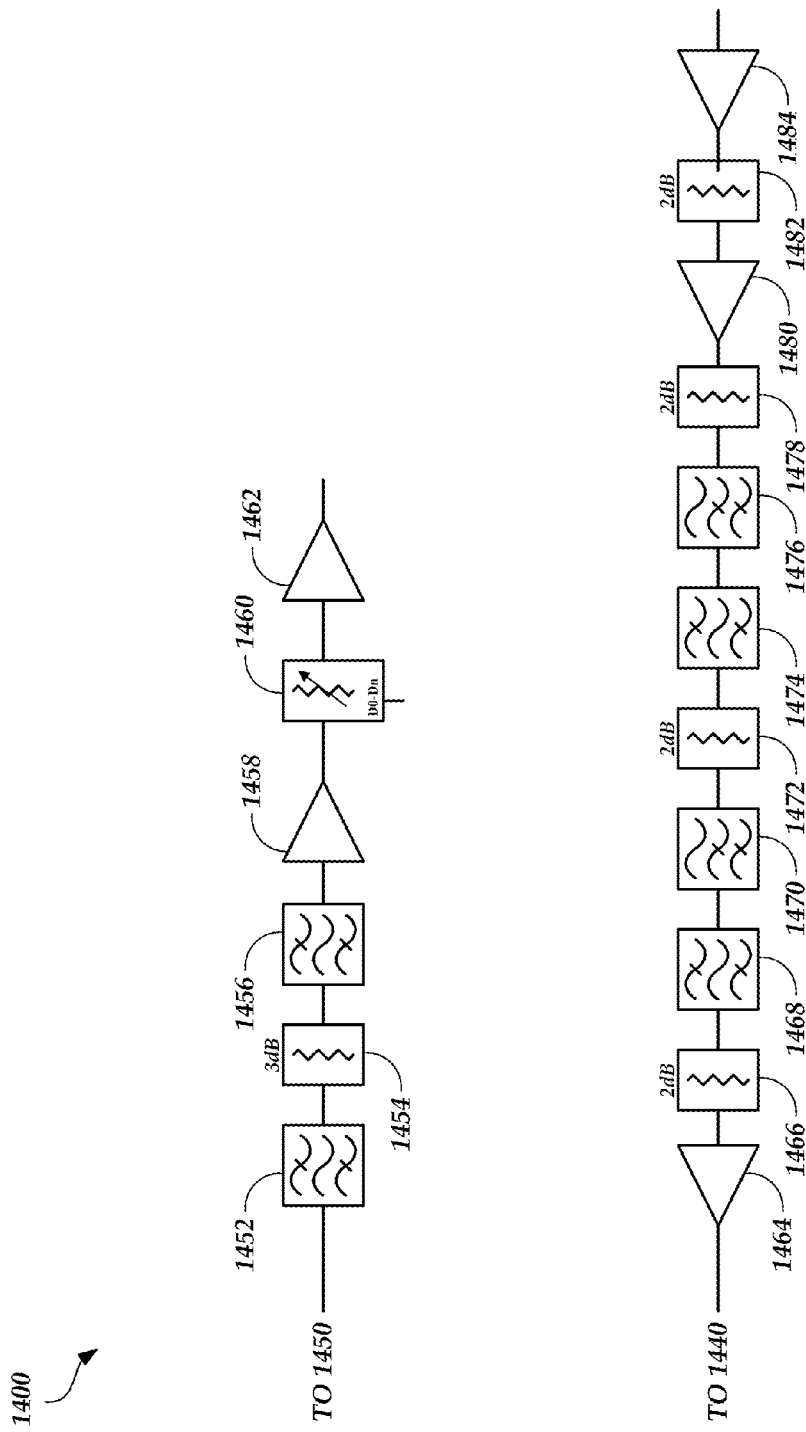

FIGS. 14A-14B illustrate a schematic 1400 of an exemplary RADAR system that generates and utilizes the enhanced waveform and the hybrid waveform described herein. In an embodiment, the RADAR system uses coherent Pulse-Doppler processing and pulse compression, such as typically used in military RADAR equipment. In addition, the RADAR system includes the following features: (1) the RADAR system is capable of uploading two waveforms for storage in internal memory (e.g., an LFM waveform and an enhanced waveform); (2) the two stored waveforms can be radiated out consecutively or in sequence, with a programmable delay (e.g., about 1 µs); (3) the two stored waveforms can have an arbitrary length and arbitrary bandwidth (e.g., up to 500 MHz); (4) the pulse repetition frequency and the number of pulses to be integrated can be arbitrarily selected; (5) the radiated output is centered between 2000 MHz and 2500 MHz, with an adjustable power level up to 1 W; (6) the user has the option of selecting the maximum range, the minimum range, and/or the dynamic range; (7) data from the RADAR system can be collected continuously and in real-time and/or transmitted over a wired or wireless network to another system or server for analysis and/or display; and (8) generated hybrid waveforms can be continuously saved for use in generating range-Doppler maps and/or range-Doppler movies (e.g., animated versions of the range-Doppler maps, where each successive frame displays newly generated hybrid waveform data). The features of the RADAR system described above are merely listed for illustrative purposes. One of more of the values described above may be varied and similar results may be achieved.

As an example, the RADAR system may be constructed to detect specific targets, such as humans walking or slowly-moving cars (e.g., less than 40 mph). Thus, the RADAR system may have the following specifications: (1) a signal bandwidth of 500 MHz; (2) a frequency of operation in the S-band (e.g., which may result in fewer coherency issues); (3) a maximum output power of 1 W with a 100 m maximum range; (4) a network interface such that generated data can be streamed to another system; and (5) a dynamic range of about 70 dB (e.g., where the dynamic range depends on the length of the waveform).

As illustrated in FIG. 14A, the schematic 1400 of the RADAR system includes a field programmable gate array 1402, a DAC 1404, an ADC 1406, resistance networks 1408, 1422, 1426, 1432, 1436, 1440, 1446, 1448, and 1450, an oscillator 1410, low pass filters 1412, 1414, 1416, 1418, 1420, and 1428, mixers 1424 and 1438, amplifiers 1430 and 1434, an oscillator 1442, and a signal splitter 1444. As illustrated in FIG. 14B, the schematic 1400 further includes microwaves 1452, 1456, 1468, and 1474, resistance networks 1454, 1466, 1472, 1478, and 1482, high pass amplifiers 1458 and 1462, a programmable attenuator 1460, low noise amplifiers 1464, 1480, and 1484, and high pass filters 1470 and 1476. The high pass amplifier 1462 may act as a transmit antenna that transmits generated waveforms (e.g., the enhanced waveform, the LFM waveform, other poly-phase code waveforms, etc.) and the low noise amplifier 1484 may act as a receive antenna that receives waveforms reflected off a target 140 (e.g., reflected enhanced waveforms, reflected LFM waveforms, other reflected poly-phase code waveforms, etc.). As an illustrative example, the components depicted in the schematic 1400 may be powered via a 15V, a 12V, and/or a 5V DC voltage, the oscillator 1410 may operate at 2 GHz, and the oscillator 1442 may operate at 1.8 GHz.

The FPGA 1402 may be configured with specific instructions such that the ADC 1406 and the DAC 1404 are interfaced in a synchronous manner and such that data can be radiated and/or captured at specific timestamps. Captured data (e.g., reflected waveforms) may be encapsulated in a user datagram protocol (UDP) packet by the FPGA 1402 for transmission via a network to an external system.

Example Operational Results

To test the performance of the enhanced waveform as compared with an LFM waveform, the following numbers were used for each waveform: (1) waveform length of 2000 samples (e.g., 1000 complex samples and 4000 samples at the receiver); (2) a bandwidth of 250 MHz (e.g., -125 MHz to 125 MHz); and (3) a sampling frequency of 2 GHz. To test the performance of the enhanced waveform as compared with a Gold code waveform, the original Gold code waveform was normalized such that the Gold code waveform has 2772 range bins, a digital filter of 250 MHz was applied to reduce harmonics that occurred at that frequency in the Gold code waveform, and the enhanced waveform was modified in the same manner.

Figure 15A:
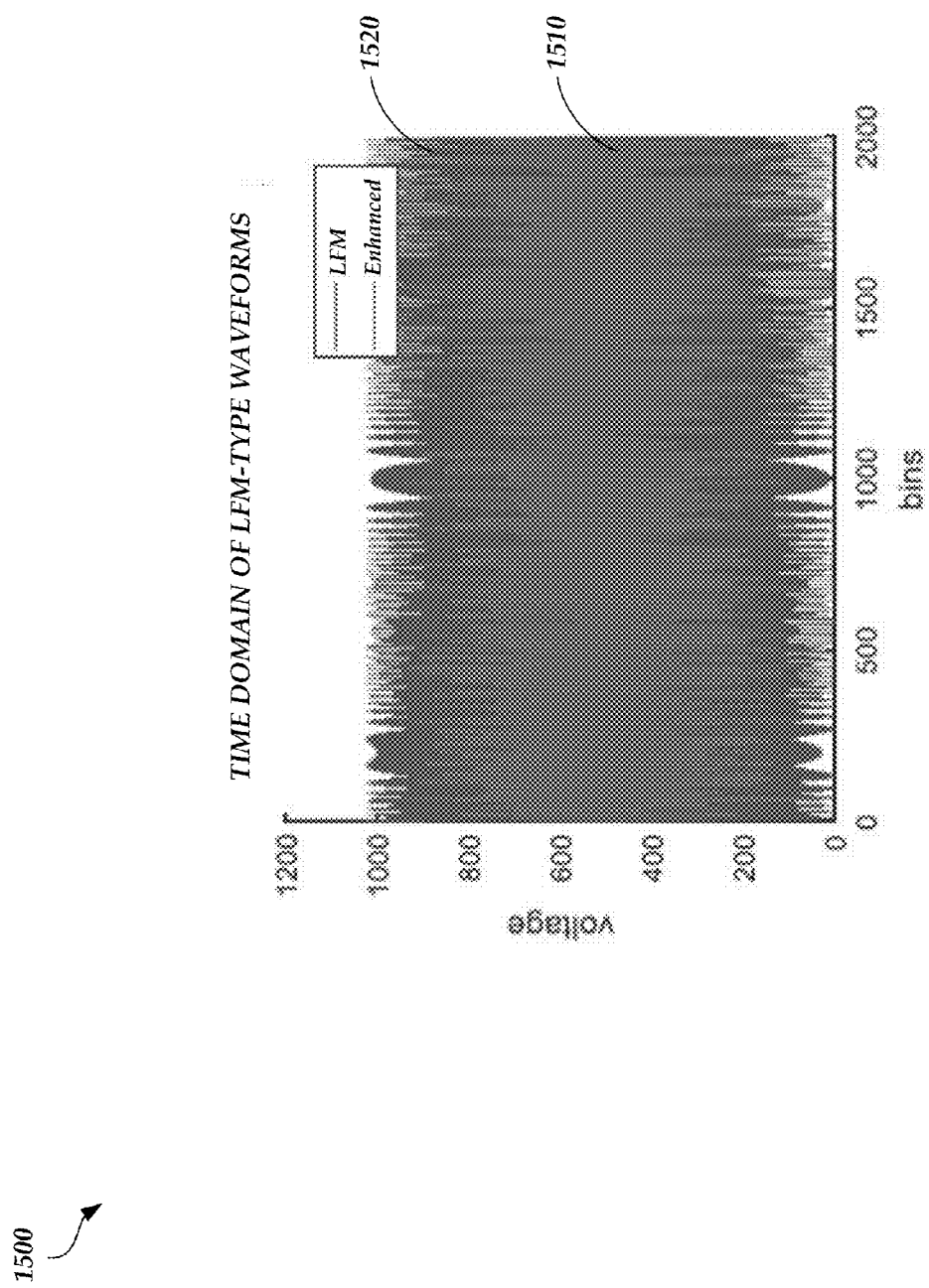
FIG. 15A illustrates a graph depicting a time domain signal of an LFM waveform and a time domain signal of an enhanced waveform according to the parameters of a test.
Figure 15B:
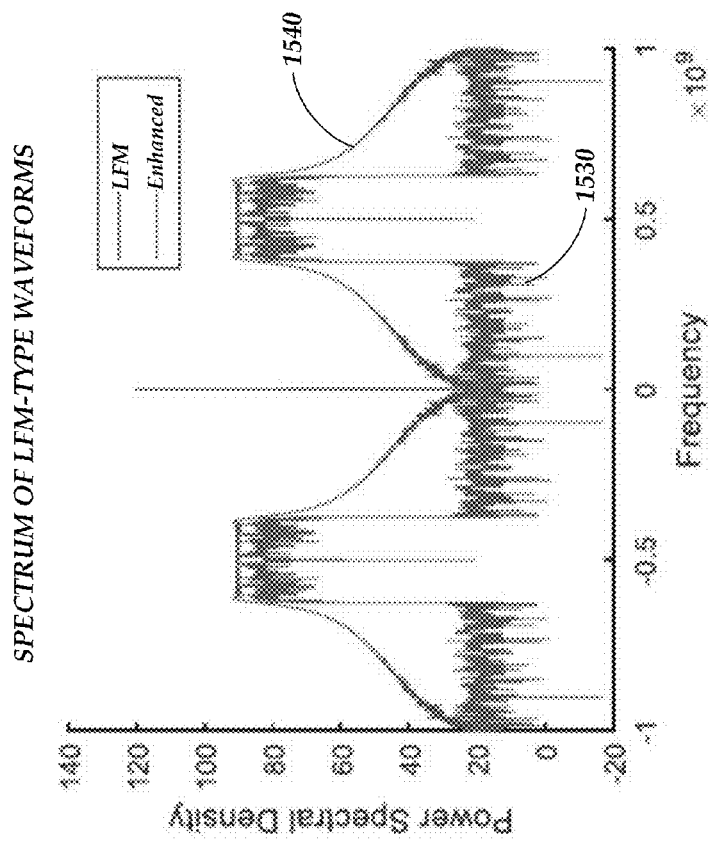
FIG. 15B illustrates a graph depicting a spectrum signal of an LFM waveform and a spectrum signal of the enhanced waveform according to the parameters of a test.
Figure 15C:
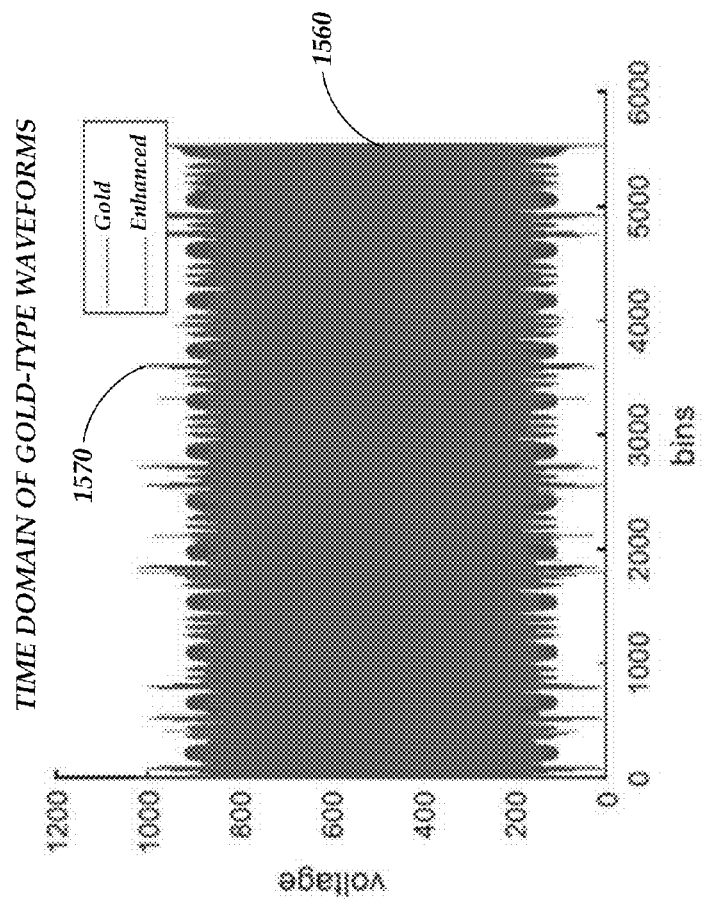
FIG. 15C illustrates a graph depicting a time domain signal of a Gold code waveform and a time domain signal of an enhanced waveform according to the parameters of a test.
Figure 15D:
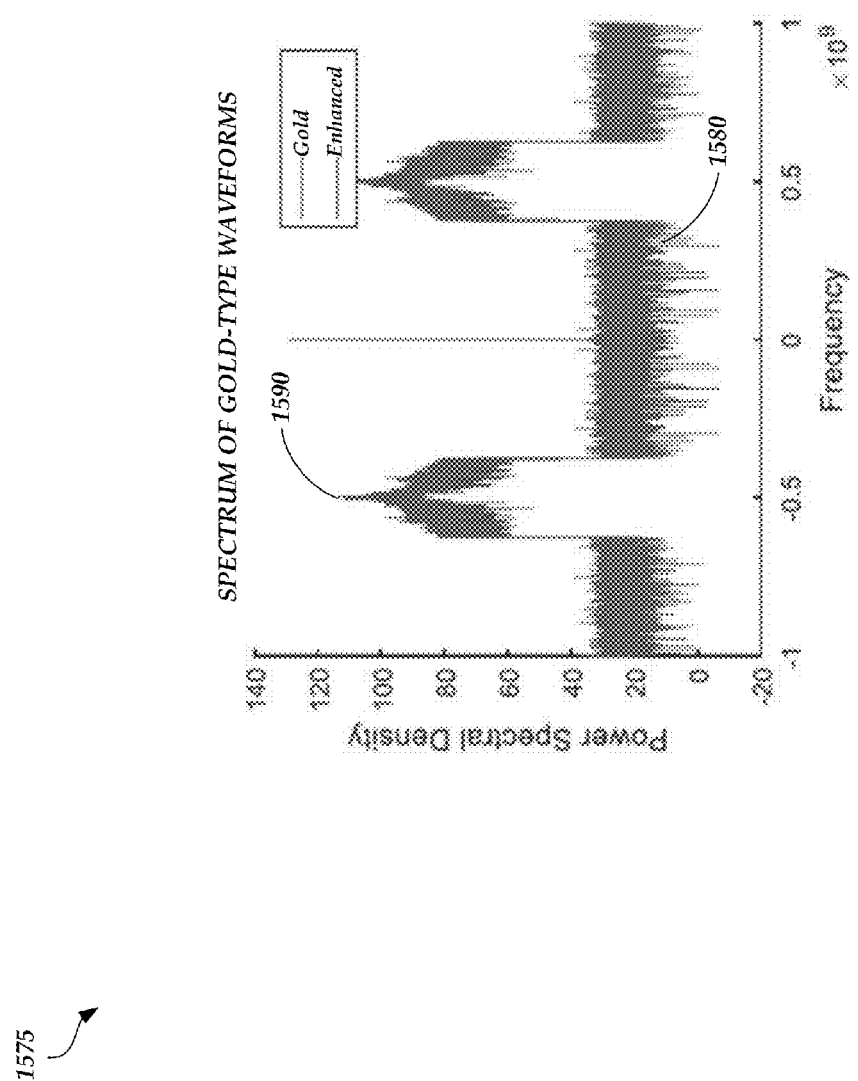
FIG. 15D illustrates a graph depicting a spectrum signal of a Gold code waveform and a spectrum signal of the enhanced waveform according to the parameters of a test.

FIG. 15A illustrates a graph 1500 depicting a time domain signal 1520 of an LFM waveform and a time domain signal 1510 of an enhanced waveform according to the parameters of the above-described test. FIG. 15B illustrates a graph 1525 depicting a spectrum signal 1540 of an LFM waveform and a spectrum signal 1530 of the enhanced waveform according to the parameters of the above-described test. FIG. 15C illustrates a graph 1550 depicting a time domain signal 1570 of a Gold code waveform and a time domain signal 1560 of an enhanced waveform according to the parameters of the above-described test. FIG. 15D illustrates a graph 1575 depicting a spectrum signal 1590 of a Gold code waveform and a spectrum signal 1580 of the enhanced waveform according to the parameters of the above-described test.

Figure 16A:
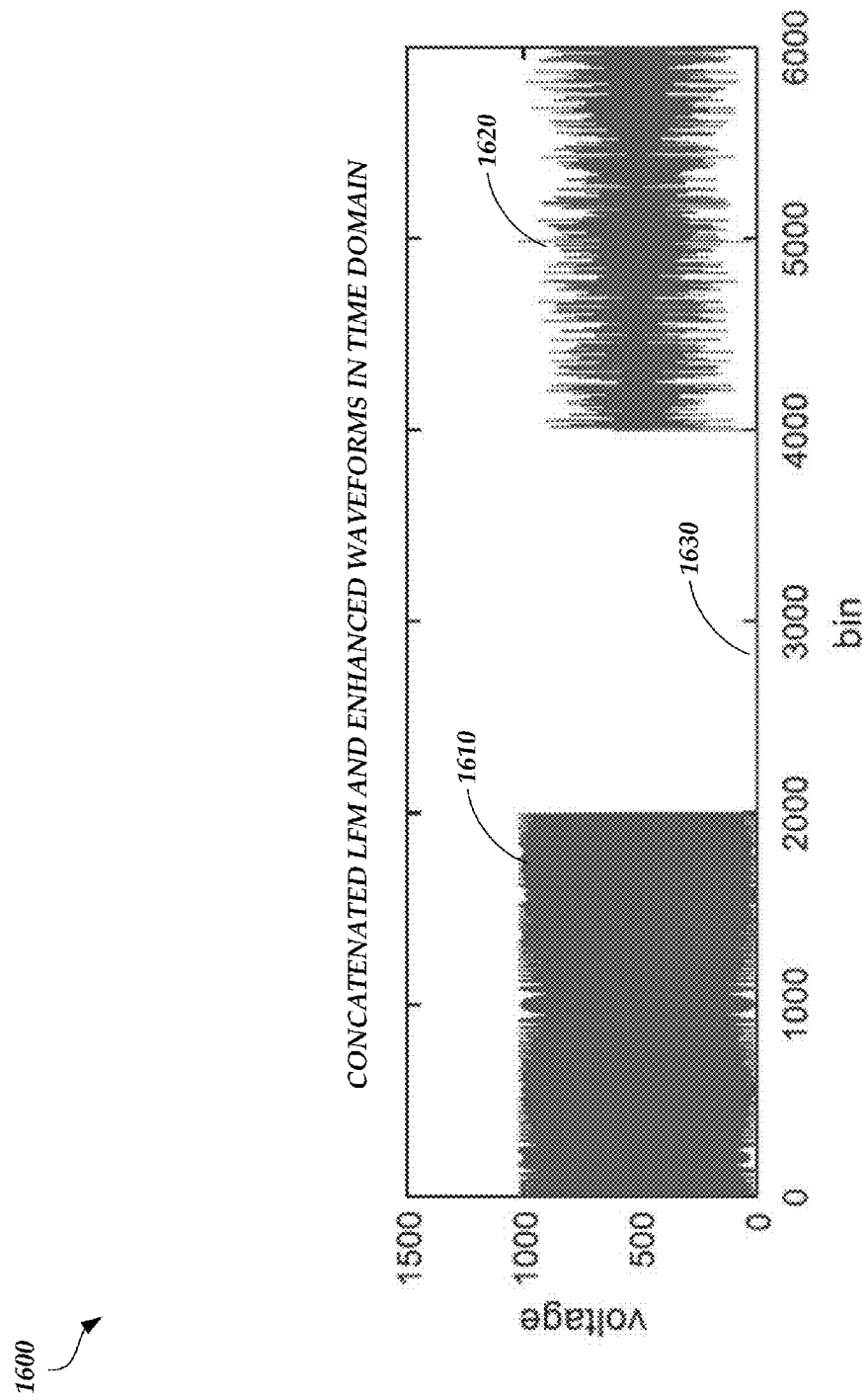
FIG. 16A illustrates a graph depicting a time domain signal of an LFM waveform concatenated with an enhanced waveform as the concatenated waveforms pass through a DAC for eventual transmission by a transmitter.

FIG. 16A illustrates a graph 1600 depicting a time domain signal of an LFM waveform 1610 concatenated with an enhanced waveform 1620 as the concatenated waveforms pass through a DAC for eventual transmission by a transmitter. As illustrated in FIG. 16A, a programmable delay is implemented such that a gap 1630 (e.g., a portion in which no signal is present and/or the amplitude of a signal is within a threshold value of 0V) is present between the LFM waveform 1610 and the enhanced waveform 1620. As described herein, the LFM waveform 1610 and the enhanced waveform 1620 can be generated separately and stored locally in memory. The signal generators 110A, 111A, and/or 11B and/or the transmitters 120A and/or 120B can retrieve the generated waveforms 1610 and 1620 from memory and perform the concatenation to form the concatenated waveform depicted in the graph 1600. The concatenated waveform can then be transmitted for target detection purposes.

In some embodiments, the gap 1630 is the same length (in time) as the LFM waveform 1610 and the enhanced waveform 1620. In other embodiments, the gap 1630 is a different length than the LFM waveform 1610 and/or the enhanced waveform 1620.

Figure 16B:
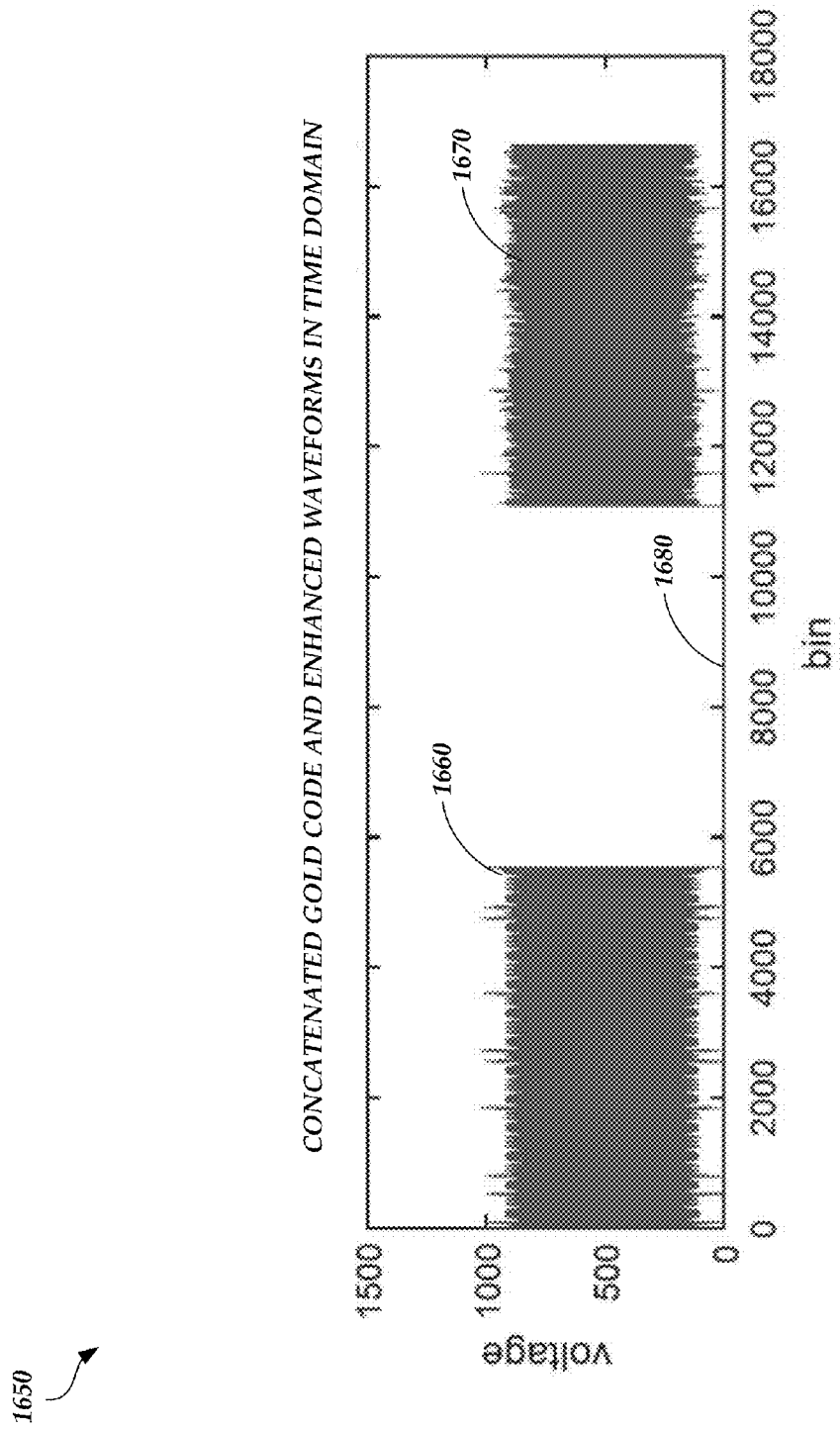
FIG. 16B illustrates a graph depicting a time domain signal of a Gold code waveform concatenated with an enhanced waveform as the concatenated waveforms pass through a DAC for eventual transmission by a transmitter.

FIG. 16B illustrates a graph 1650 depicting a time domain signal of a Gold code waveform 1660 concatenated with an enhanced waveform 1670 as the concatenated waveforms pass through a DAC for eventual transmission by a transmitter. As illustrated in FIG. 16B, a programmable delay is implemented such that a gap 1680 is present between the Gold code waveform 1660 and the enhanced waveform 1670. As described herein, the Gold code waveform 1660 and the enhanced waveform 1670 can be generated separately and stored locally in memory. The signal generators 110A, 111A, and/or 11B and/or the transmitters 120A and/or 120B can retrieve the generated waveforms 1660 and 1670 from memory and perform the concatenation to form the concatenated waveform depicted in the graph 1650. The concatenated waveform can then be transmitted for target detection purposes.

In some embodiments, the gap 1680 is the same length (in time) as the Gold code waveform 1660 and the enhanced waveform 1670. In other embodiments, the gap 1680 is a different length than the Gold code waveform 1660 and/or the enhanced waveform 1670.

In situations in which a target 140 is near a hybrid pulse compression RF system 105A-105F (e.g., within 200 meters), the LFM waveform 1610 or Gold code waveform 1660 may reach the target 140 prior to the transmission of the enhanced waveform 1620 or 1670.

FIG. 17 illustrates a graph 1700 depicting a frame from three range-Doppler movies or animations 1702, 1704, and 1706 that are created by a hybrid pulse compression RF system of FIGS. 1A-1F (e.g., the hybrid waveform generator 170) as a result of receiving reflected waveform(s). As described herein, a range-Doppler movie is an animated graphical representation of a detected target, where each frame of the movie depicts a then-current detected location of the target. The range-Doppler movie, when animated, may then depict the real-time or nearly real-time (e.g., within a few seconds of real-time) movement of a detected target. The hybrid pulse compression RF systems 105A-105F may use the hybrid waveform data to generate the range-Doppler movie.

The range-Doppler movie 1702 frame depicts, within circle 1710, a representation of a target detected using the LFM waveform only. Similarly, the range-Doppler movie 1704 frame depicts, within circle 1720, a representation of a target detected using the enhanced waveform only. Finally, the range-Doppler movie 1706 frame depicts, within circle 1730, a representation of a target detected using the hybrid waveform (e.g., based on the LFM and enhanced waveforms) described herein. As illustrated in FIG. 17, the range-Doppler movie 1706 frame depicts a cleaner result than the range-Doppler movie 1702 and 1704 frames. For example, the range-Doppler movie 1706 frame depicts less background clutter (e.g., lighter shaded areas outside the circles 1710, 1720, and 1730) and Doppler side lobes are reduced.

FIG. 18 illustrates a graph 1800 depicting a frame from three range-Doppler movies or animations 1802, 1804, and 1806 that are created by a hybrid pulse compression RF system of FIGS. 1A-1F (e.g., the hybrid waveform generator 170) as a result of receiving reflected waveform(s). The range-Doppler movie 1802 frame depicts, within circle 1810, a representation of a target detected using the Gold code waveform only. Similarly, the range-Doppler movie 1804 frame depicts, within circle 1820, a representation of a target detected using the enhanced waveform only. Finally, the range-Doppler movie 1806 frame depicts, within circle 1830, a representation of a target detected using the hybrid waveform (e.g., based on the Gold code and enhanced waveforms) described herein. As illustrated in FIG. 18, the range-Doppler movie 1806 frame depicts a cleaner result than the range-Doppler movie 1802 and 1804 frames. For example, the range-Doppler movie 1806 frame depicts less background clutter (e.g., lighter shaded areas outside the circles 1810, 1820, and 1830) and Doppler side lobes are reduced.

Computing System

Figure 19:
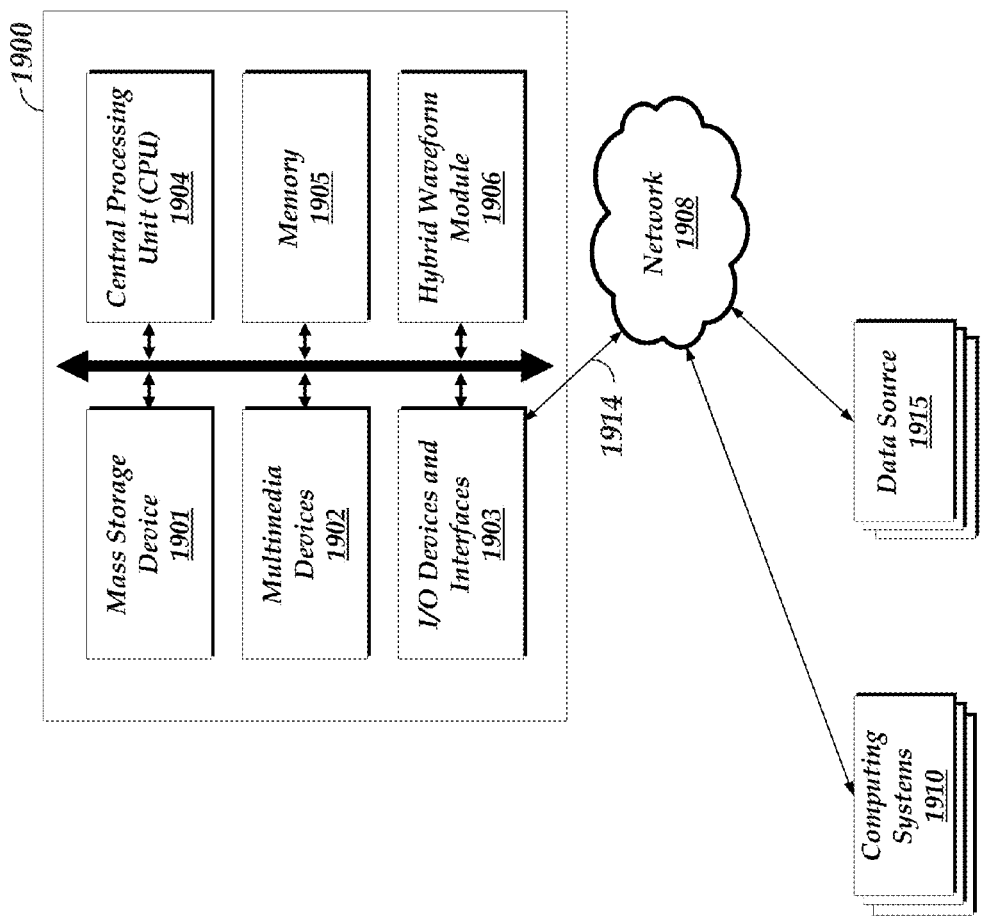
FIG. 19 is a block diagram depicting one embodiment of a computer hardware system configured to implement one or more embodiments of the hybrid pulse compression RF systems described herein.

In some embodiments, the various hybrid pulse compression RF systems 105A-105F described above can include a computing system 1900 system as illustrated in FIG. 19, which is a block diagram of one embodiment of a computing system. In some embodiments, the computing system 1900 can be in communication with one or more computing systems 1910 and/or one or more data sources 1915 via one or more networks 1908. The computing system 1900 may be used to implement one or more of the systems and methods described herein. For example, in some embodiments, the computing system 1900 may be configured to generate the enhanced waveform and/or the hybrid waveform described herein. While FIG. 19 illustrates one embodiment of a computing system 1900, it is recognized that the functionality provided for in the components and modules of computing system 1900 may be combined into fewer components and modules or further separated into additional components and modules.

In some embodiments, the system 1900 comprises a hybrid waveform module 1906 that carries out the functions described herein with reference to generating a hybrid waveform, including any one of the methods described above. For example, the hybrid waveform module 1906 may cross-correlate reflected waveforms with originally generated waveforms and/or combine the results of cross-correlation. The hybrid waveform module 1906 may be executed on the computing system 1900 by a central processing unit 1904 discussed further below. In some embodiments, one or more of the computing systems 1900, 1910 can comprise a data processing module that carries out various correlation and image generation functions described herein, such as the generation of a range-Doppler movie.

In general, the word "module," as used herein, refers to logic embodied in hardware or firmware, or to a collection of software instructions, possibly having entry and exit points, written in a programming language, such as, for example, COBOL, CICS, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

In some embodiments, the computing system 1900 also comprises a mainframe computer suitable for controlling and/or communicating with large databases, performing high volume transaction processing, and generating reports from large databases. The computing system 1900 also comprises a central processing unit ("CPU") 1904, which may comprise one or more conventional microprocessors. The computing system 1900 further comprises a memory 1905, such as random access memory ("RAM") for temporary storage of information and/or a read only memory ("ROM") for permanent storage of information, and can include a mass storage device 1901, such as a hard drive, diskette, or optical media storage device. Typically, the modules of the computing system 1900 are connected to the computer using a standards-based bus system. In different embodiments, the standards-based bus system could be Peripheral Component Interconnect (PCI), Microchannel, SCSI, Industrial Standard Architecture (ISA) and Extended ISA (EISA) architectures, for example.

In some embodiments, the computing system 1900 can include one or more commonly available input/output (I/O) devices and interfaces 1903, such as a keyboard, mouse, touchpad, and printer. In one embodiment, the I/O devices and interfaces 1903 comprise one or more display devices (e.g., the display 180), such as a monitor, that allows the visual presentation of data to a user. More particularly, a display device provides for the presentation of GUIs, application software data, and multimedia presentations, for example. In the embodiment of FIG. 19, the I/O devices and interfaces 1903 also provide a communications interface to various external devices. The computing system 1900 may also comprise one or more multimedia devices 1902, such as speakers, video cards, graphics accelerators, microphones, hydrophones, photodetectors, for example.

The computing system 1900 may run on a variety of computing devices, such as, for example, a server, a Windows server, a Structure Query Language server, a Unix server, a personal computer, a mainframe computer, a laptop computer, a cell phone, a personal digital assistant, a kiosk, an audio player, and so forth. The computing system 1900 is generally controlled and coordinated by operating system software, such as z/OS, Windows 95, Windows 98, Windows NT, Windows 2000, Windows XP, Windows Vista, Windows 7, Windows 8, Windows 10, Linux, BSD, SunOS, Solaris, or other compatible operating systems. In Macintosh systems, the operating system may be any available operating system, such as MAC OS X. In other embodiments, the computing system 1900 may be controlled by a proprietary operating system. Conventional operating systems control and schedule computer processes for execution, perform memory management, provide file system, networking, and I/O services, and provide a user interface, such as a graphical user interface ("GUI"), among other things.

In the embodiment of FIG. 19, the computing system 1900 is coupled to a network 1908, such as a LAN, WAN, or the Internet, for example, via a wired, wireless, or combination of wired and wireless, communication link 1915. The network 1908 communicates with various computing devices and/or other electronic devices via wired or wireless communication links. In the embodiment of FIG. 19, the network 1908 is communicating with one or more computing systems 1910 and/or one or more data sources 1915.

Access to the hybrid waveform module 1906 of the computer system 1900 by computing systems 1910 and/or by data sources 1915 may be through a web-enabled user access point such as the computing systems' 1910 or data source's 1915 personal computer, cellular phone, laptop, tablet, or other device capable of connecting to the network 1908. Such a device may have a browser module that is implemented as a module that uses text, graphics, audio, video, and other media to present data and to allow interaction with data via the network 1908.

The browser module may be implemented as a combination of an all points addressable display such as a cathode-ray tube (CRT), a liquid crystal display (LCD), a plasma display, or other types and/or combinations of displays. In addition, the browser module may be implemented to communicate with input devices 1903 and may also comprise software with the appropriate interfaces which allow a user to access data through the use of stylized screen elements such as, for example, menus, windows, dialog boxes, toolbars, and controls (for example, radio buttons, check boxes, sliding scales, and so forth). Furthermore, the browser module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 1900 may comprise a physical or logical connection established between a remote microprocessor and a mainframe host computer for the express purpose of uploading, downloading, or viewing interactive data and databases on-line in real time. The remote microprocessor may be operated by an entity operating the computer system 1900, including the client server systems or the main server system, and/or may be operated by one or more of the data sources 1915 and/or one or more of the computing systems 1910. In some embodiments, terminal emulation software may be used on the microprocessor for participating in the micro-mainframe link.

In some embodiments, computing systems 1910 that are internal to an entity operating the computer system 1900 may access the hybrid waveform module 1906 internally as an application or process run by the CPU 1904.

In an embodiment, a user access point or user interface 1903 comprises a personal computer, a laptop computer, a cellular phone, a GPS system, a Blackberry® device, a portable computing device, a server, a computer workstation, a local area network of individual computers, an interactive kiosk, a personal digital assistant, an interactive wireless communications device, a handheld computer, an embedded computing device, or the like.

In addition to the systems that are illustrated in FIG. 19, the network 1908 may communicate with other data sources or other computing devices. The computing system 1900 may also comprise one or more internal and/or external data sources. In some embodiments, one or more of the data repositories and the data sources may be implemented using a relational database, such as DB2, Sybase, Oracle, CodeBase and Microsoft® SQL Server as well as other types of databases such as, for example, a signal database, an object-oriented database, and/or a record-based database.

Example Use Cases

As discussed above, in addition to applications with RADAR (regular and millimeter), various embodiments described herein can be used in hybrid pulse compression systems that generate signals or waveforms to detect objects, including LIDAR, SONAR, ultrasound, MRI, CT scans, non-destructive inspections (e.g., scanning acoustic microscopy, ultrasonic, magnetic-particle, etc.), etc., to name a few examples.

Figure 20:
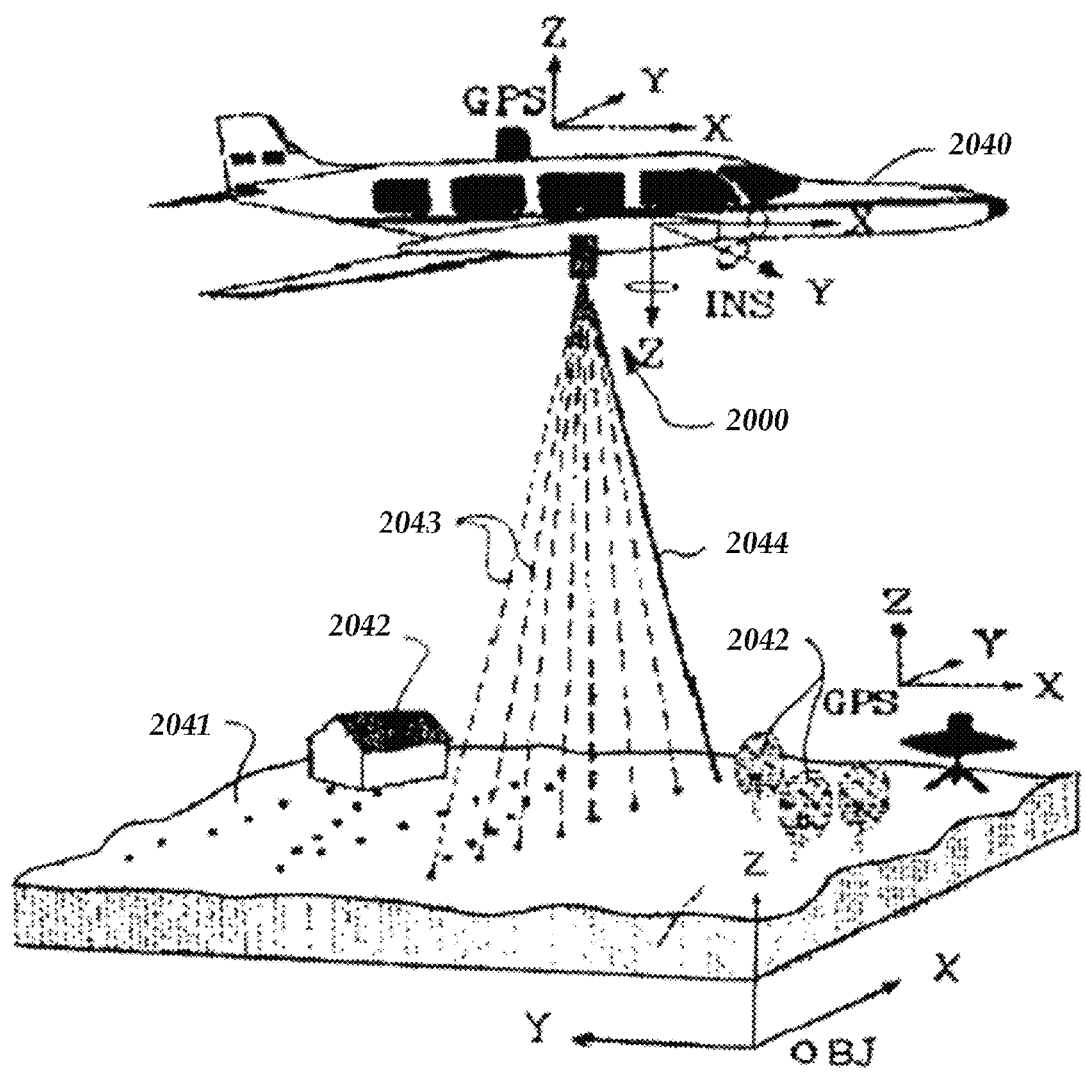
FIG. 20 is a schematic diagram that illustrates the implementation of one embodiment of a hybrid pulse compression system in imaging targets on the ground from an aircraft.

For example, FIG. 20 is a schematic diagram that illustrates implementation of an embodiment of a hybrid pulse compression system 2000 using poly-phase code waveforms (e.g., LFM waveforms) and enhanced waveforms as described herein in order to image targets on the ground 2041 from an aircraft 2040 via LIDAR. LIDAR is an optical remote sensing technology that measures properties of scattered light to find range and/or other information of a distant target. The prevalent method to determine distance to an object 2042 or surface 2041 is to use laser pulses 2043 (e.g., a poly-phase code waveform laser pulse and an enhanced waveform laser pulse). Like RADAR technology, which uses radio waves, the range to an object 2042 is determined by measuring the time delay between transmission of a laser pulse 2043 and detection of the reflected signal 2044.

A recent addition to a police officer's speed detection arsenal is LIDAR. To measure a vehicle's speed, LIDAR determines how long it takes a light pulse to travel from the LIDAR gun to the vehicle and back. From this information, LIDAR can quickly find the distance between the gun and the vehicle. By making several measurements and comparing the distance the vehicle traveled between measurements, LIDAR very accurately determines the vehicle's speed. LIDAR uses a laser beam of invisible infrared light. The beam reflects off any flat surface on the vehicle. Since the beam is very narrow, it is impossible for any laser detector to determine the distance between the LIDAR source and the vehicle.

Just as there are two types of RADAR, there are also two types of lasers: Pulsed Lasers and Continuous Wave (CW) Lasers, which are used in LIDAR applications. The present disclosure includes use of the hybrid pulse compression system 2000 with poly-phase code waveforms and enhanced waveforms for use in ranging and Doppler measurement applications.

Figure 21:
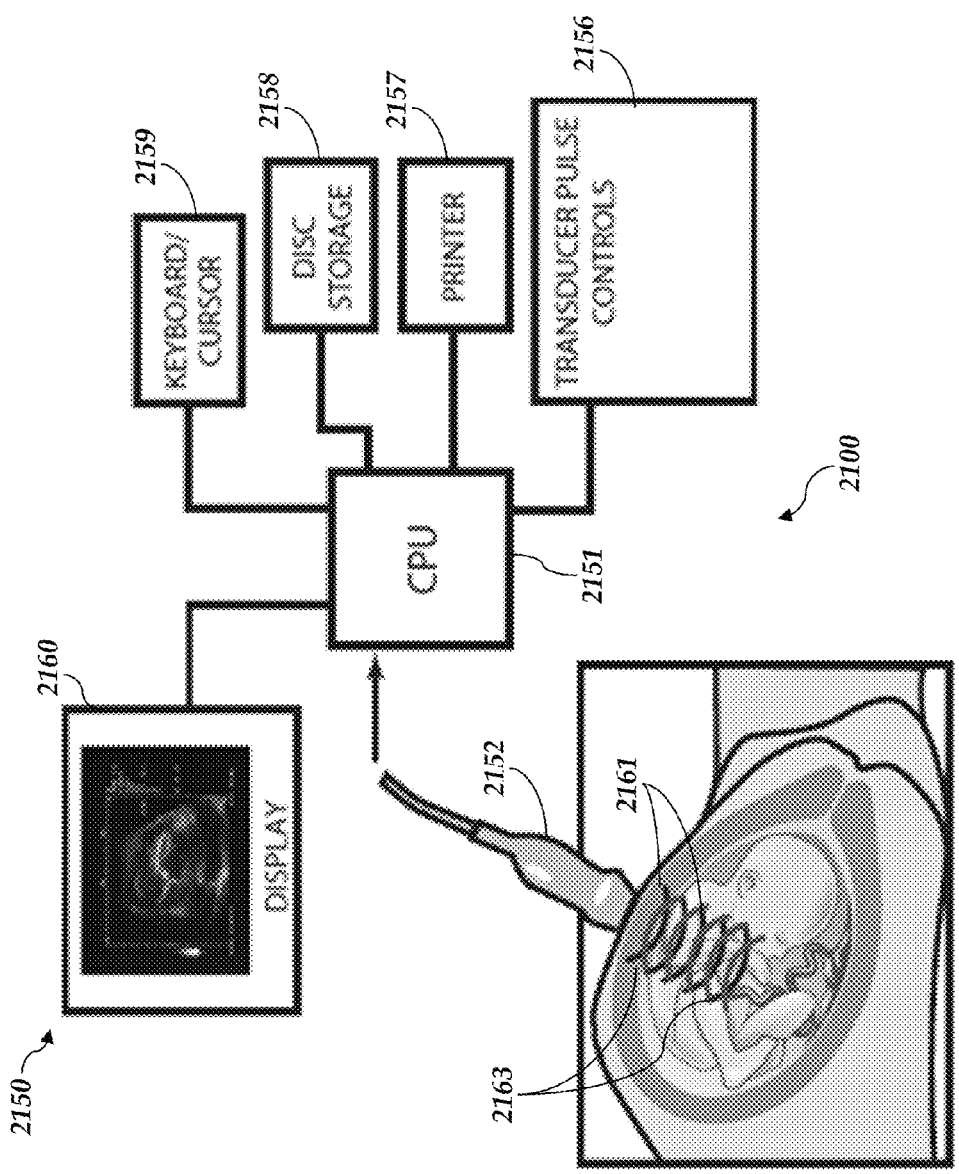
FIG. 21 is a schematic diagram that illustrates the implementation of one embodiment of a hybrid pulse compression system in an ultrasonic imaging application.

Referring next to FIG. 21, a high-resolution medical ultrasound system 2150 which utilizes an illustrative embodiment of the hybrid pulse compression system 2100 that uses poly-phase code waveforms (e.g., LFM waveforms) and enhanced waveforms as described herein is illustrated. The hybrid pulse compression system 2100 may include an ultrasound transducer 2152. The poly-phase code waveform and the enhanced waveform can be sent to the transducer 2152. In some embodiments, a CPU 2151 that can be used to generate a poly-phase code waveform and/or an enhanced waveform may interface with the ultrasound transducer 2152. In some embodiments, the CPU 2151 or an additional CPU may be used to cross-correlate reflected waveforms with the originally generated waveforms and/or combine the results of cross-correlation and generate an image. Additional devices may interface with the CPU 2151. The additional devices may include transducer pulse controls 2156 (which can be used to modify aspects of the poly-phase code and/or enhanced waveforms, such as their duration), a printer 2157, a disc storage device 2158, a keyboard/cursor 2159, and/or a display 2160, for example and without limitation.

The hybrid pulse compression system 2100 transmits high frequency sound pulses 2161 (e.g., poly-phase code waveform sound pulses and enhanced waveform sound pulses) through the ultrasound transducer 2152 into a patient's body 2162. The sound pulses 2161 travel through the patient's body 2162, passing through different types of tissue. Although the average speed of sound through human tissues is 1540 m/s, it does vary with exact tissue type. While the speed of sound through fat is 1459 m/s, it passes through bone at 4080 m/s. When sound encounters two adjacent tissue types with different acoustic properties, a proportion of the sound energy is reflected as reflected sound pulses 2163. These boundaries between different tissue types are called "acoustic interfaces."

The amount of reflected sound pulses 2163 reflected back from an acoustic interface depends on a property of the materials on either side of the interface called "acoustic impedance." The acoustic impedance of a material is simply the density of the material multiplied by the speed at which sound travels through the material.

Figure 22:
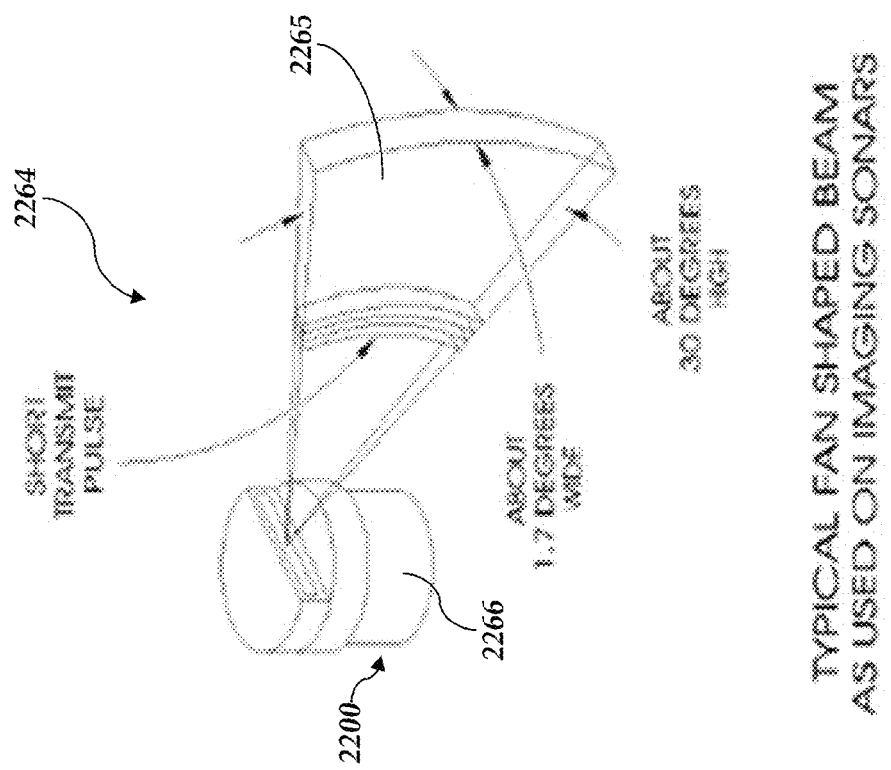
FIG. 22 is a schematic diagram that illustrates the implementation of one embodiment of a hybrid pulse compression system in a high resolution SONAR application.

Referring next to FIG. 22, a high resolution SONAR system 2264 which utilizes an illustrative embodiment of a hybrid pulse compression system 2200 is illustrated. As described above, the hybrid pulse compression system 2200 can use poly-phase code waveforms and enhanced waveforms to detect an object. The hybrid pulse compression system 2200 of the high resolution SONAR system 2264 can be used to power and drive the SONAR beam generators 2266 of the hybrid pulse compression system 2200 to emit one or more SONAR pulses 2265 (e.g., a poly-phase code waveform SONAR pulse and an enhanced waveform SONAR pulse) which may have a fan shape, as illustrated. The high resolution SONAR system 2264 uses sound propagation (usually underwater, as in submarine navigation) to navigate, communicate with or detect other vessels. There are two types of technology that share the name "SONAR": passive SONAR is essentially listening for the sound made by vessels; active SONAR is emitting pulses of sounds and listening for echoes. SONAR may be used as a means of acoustic location and of measurement of the echo characteristics of targets in the water. Acoustic location in air was used before the introduction of RADAR.

Figure 23:
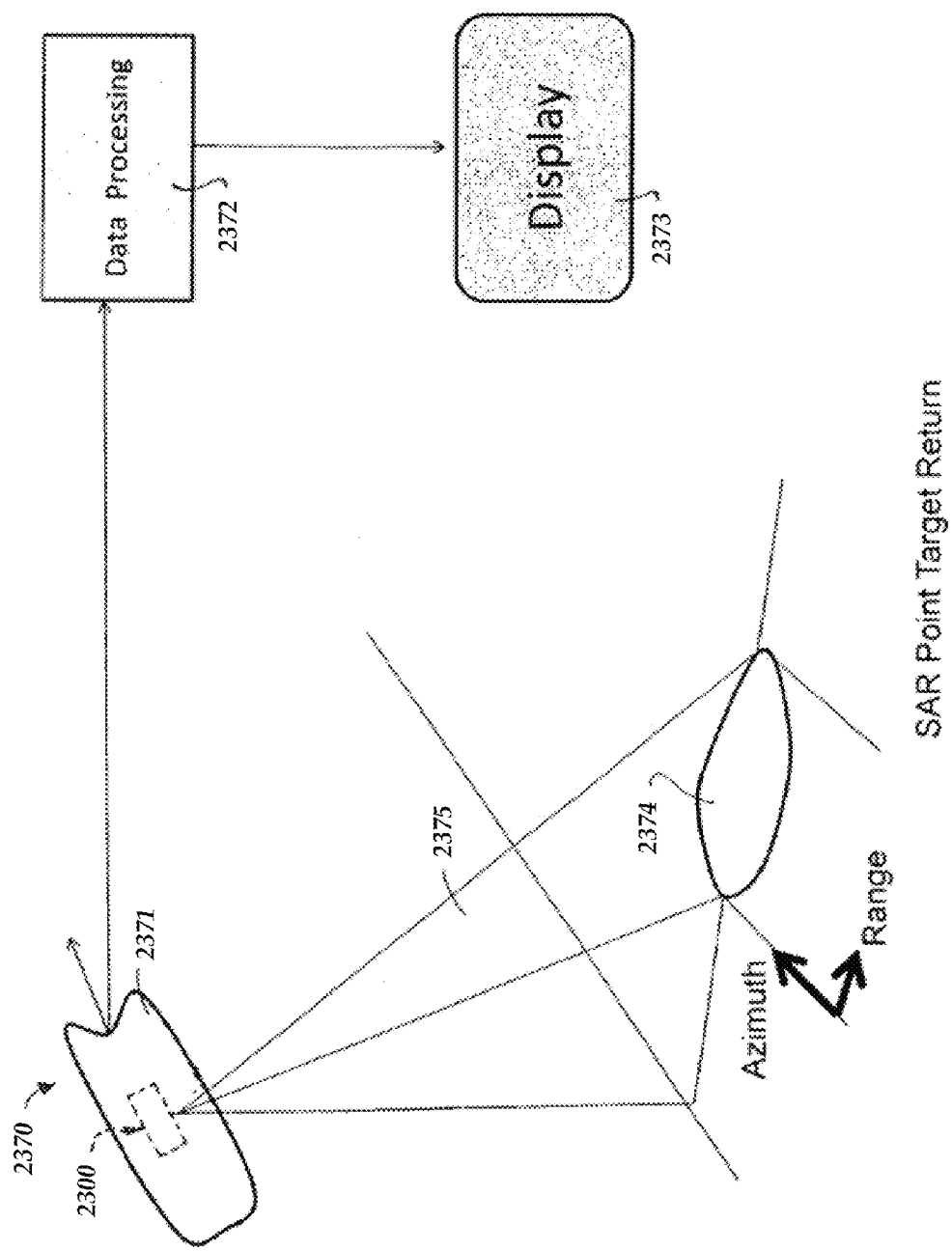
FIG. 23 is a schematic diagram that illustrates the implementation of one embodiment of a hybrid pulse compression system in a high resolution synthetic aperture application.

Referring next to FIG. 23, a high resolution synthetic aperture RADAR system 2370 that utilizes an illustrative embodiment of a hybrid pulse compression system 2300 is illustrated. As described above, the hybrid pulse compression system 2300 can use poly-phase code waveforms and enhanced waveforms to detect an object. The hybrid pulse compression system 2300 may be provided in a spacecraft 2371 and emits one or more high resolution synthetic RADAR pulses 2375 (e.g., a poly-phase code waveform RADAR pulse and an enhanced waveform RADAR pulse) against a target 2374. A reflected signal (not illustrated) is reflected from the target 2374 back to the hybrid pulse compression system 2300. A data processor 2372 interfaces with or can be included as part of the hybrid pulse compression system 2300 and cross-correlates reflected signals with originally generated high resolution synthetic RADAR pulses 2375 and/or combines the results of the cross-correlation. A high resolution image of the target 2374, based on the combined cross-correlation results, is shown on a display 2373 that interfaces with the data processor 2372.

Beginning with the launch of SESAT in 1978, Synthetic Aperture RADAR (SAR) has provided a wealth of information on such diverse phenomena as surface waves, internal waves, currents, upwelling, shoals, sea ice, wind and rainfall. SAR is the premier sensor for such phenomena because it is sensitive to small surface roughness changes of the order of RADAR wavelength (1 millimeter down to several centimeters). It is also independent of solar illumination and is generally unaffected by cloud cover. Most modern RADARs (including SARs) transmit a pulse 2375 known as linear modulated waveform and use the standard RADAR principles of range resolution and Doppler shift. Hence the linear FM pulse generator can be replaced with the hybrid pulse compression system 2300 to produce a higher resolution of SAR images on the display 2373.

Figure 24A:
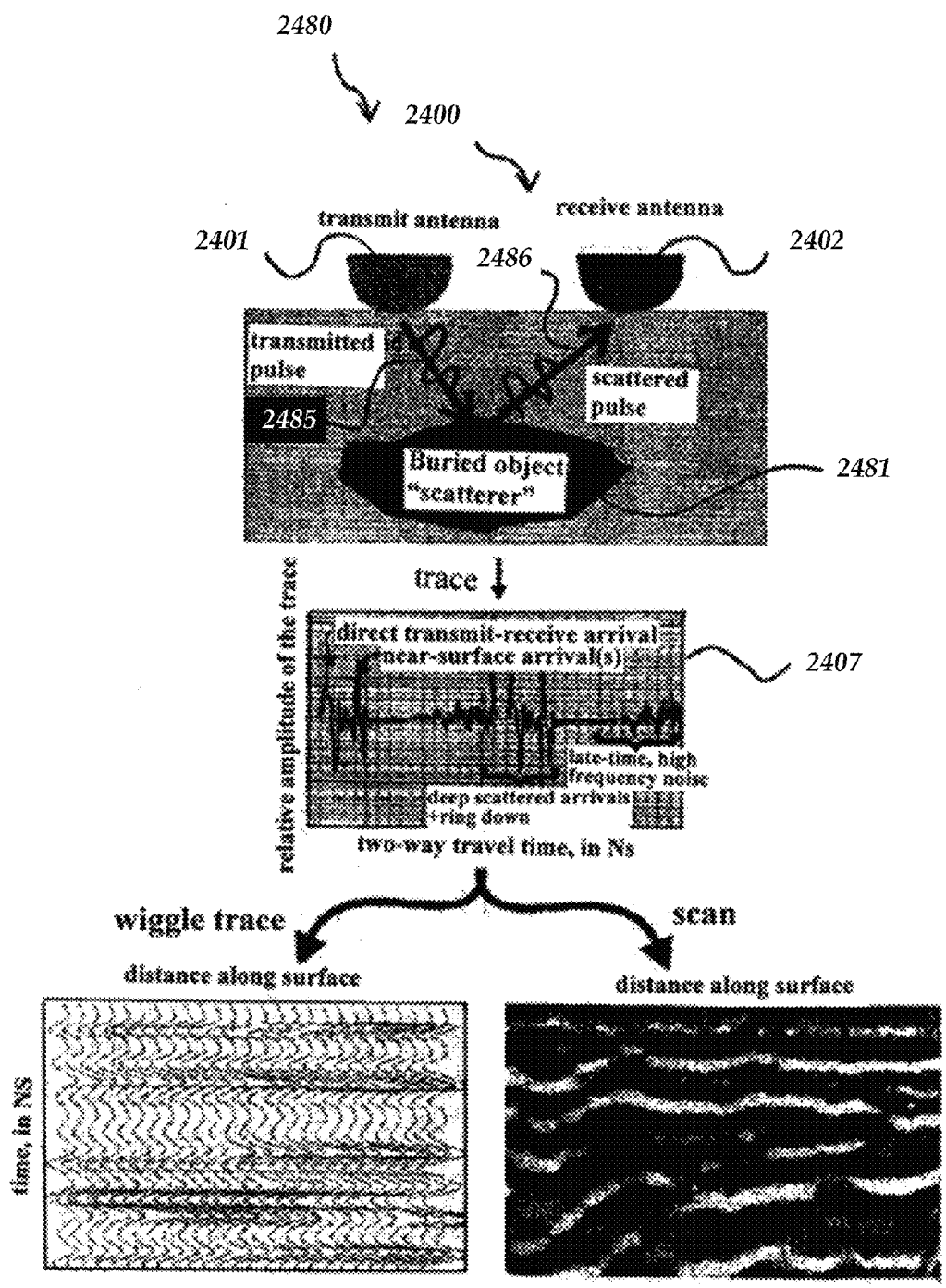
FIGS. 24A-24C are schematic diagrams that illustrate the implementation of one embodiment of a hybrid pulse compression system in a high resolution ground penetrating RADAR application.
Figure 24B:
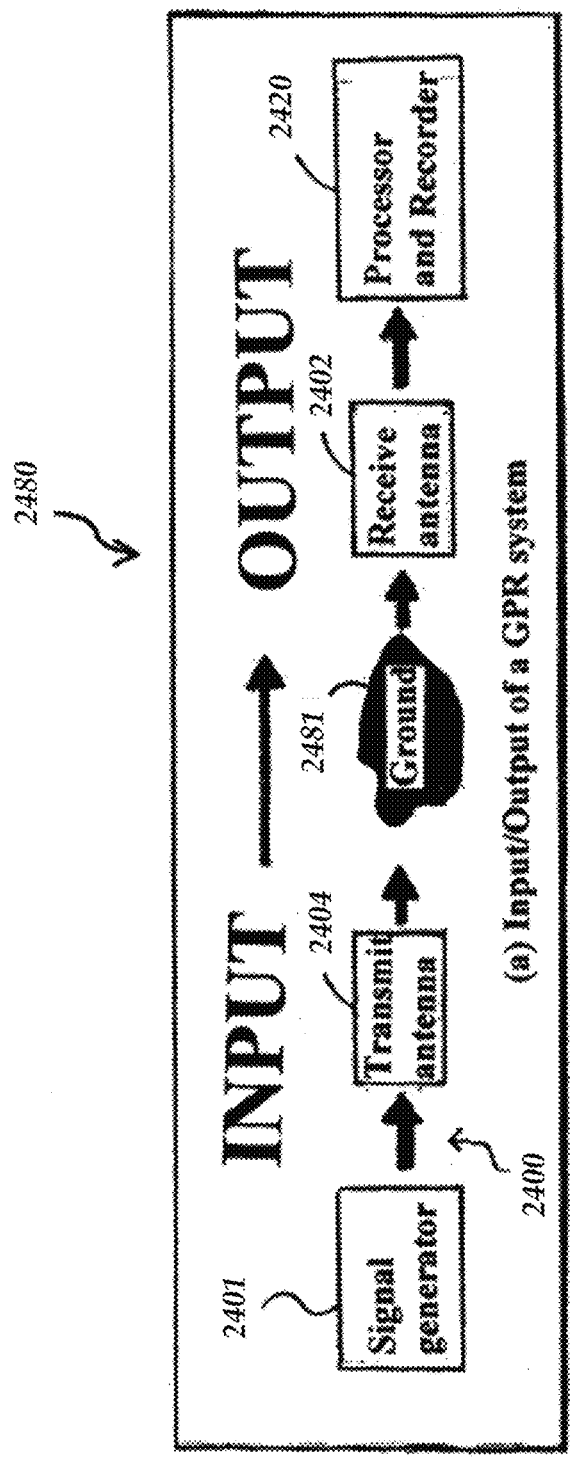
Figure 24C:
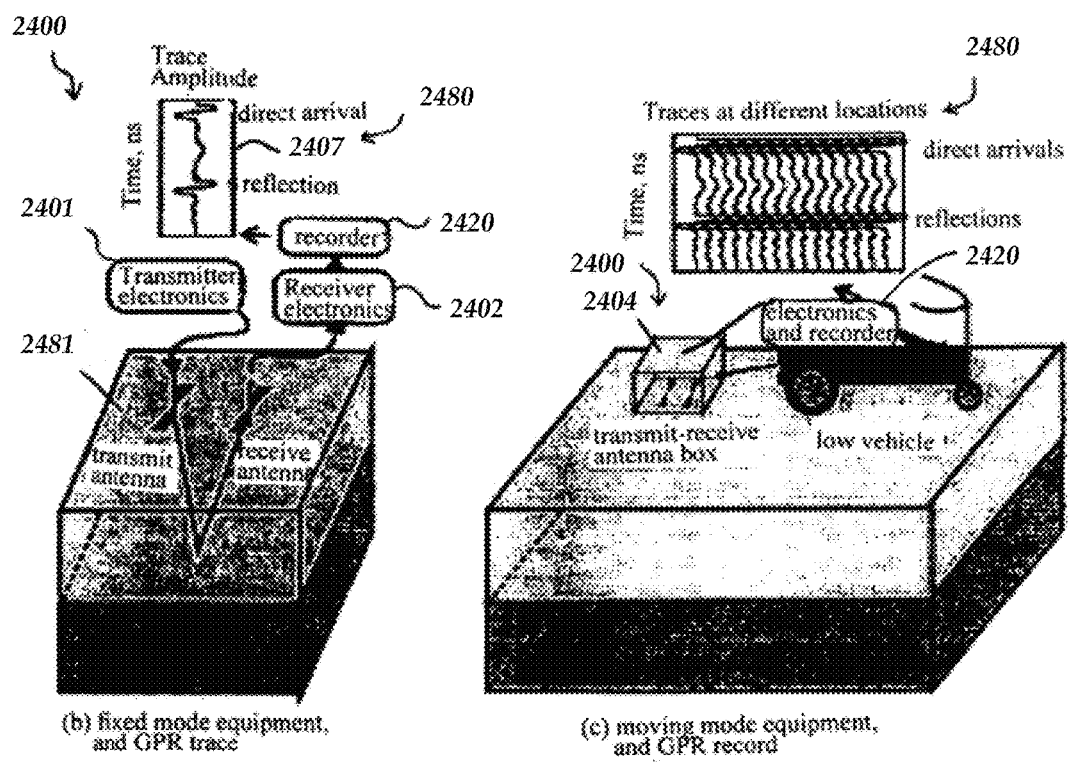

Referring next to FIGS. 24A-24C, a high resolution ground penetrating RADAR system 2480 which utilizes an illustrative embodiment of a hybrid pulse compression system 2400 is illustrated. As described above, the hybrid pulse compression system 2400 can use poly-phase code waveforms and enhanced waveforms to detect an object. Ground Penetrating RADAR (GPR) utilizes a very short burst of radio-frequency energy as a pulse 2485 (e.g., a poly-phase code waveform pulse, an enhanced waveform pulse, etc.) that is transmitted from the transmitter/signal generator 2401 via the transmit antenna 2404 of the hybrid pulse compression system 2400 and radiated into the ground 2481 to detect discontinuities in the ground 2481. The scattered pulses 2486 are reflected from the ground 2481 and detected by a receive antenna 2402 of the hybrid pulse compression system 2400. A signal processor and recorder 2420 cross-correlates the scattered pulses 2486 with the originally generated pulses 2485 and/or combines the results of the cross-correlation and records and/or displays a high-resolution image of the ground 2481 or objects or discontinuities in the ground 2481 on a display 2407, as illustrated in FIGS. 24A and 24B. Alternative applications of the hybrid pulse compression system 2400 in implementation of the high resolution ground penetrating RADAR system 2480 are illustrated in FIG. 24C.

The objects or discontinuities in the ground 2481 can be cavities, voids, transitions between soil and rock, filled areas and/or buried objects. The performance of conventional GPRs is limited by attenuation of the transmitted pulse in moist soils, especially soils having high clay content. GPRs are used to detect a boundary between rock and air (a cave or cavity) or between one type of soil and another (for example undisturbed soil-to back-filled soil). The strength of the echo signal is dependent on the absorption of the signal to and from the radar to the target, the size and shape of the target, and the degree of discontinuity at the reflecting boundary.

Figure 25:
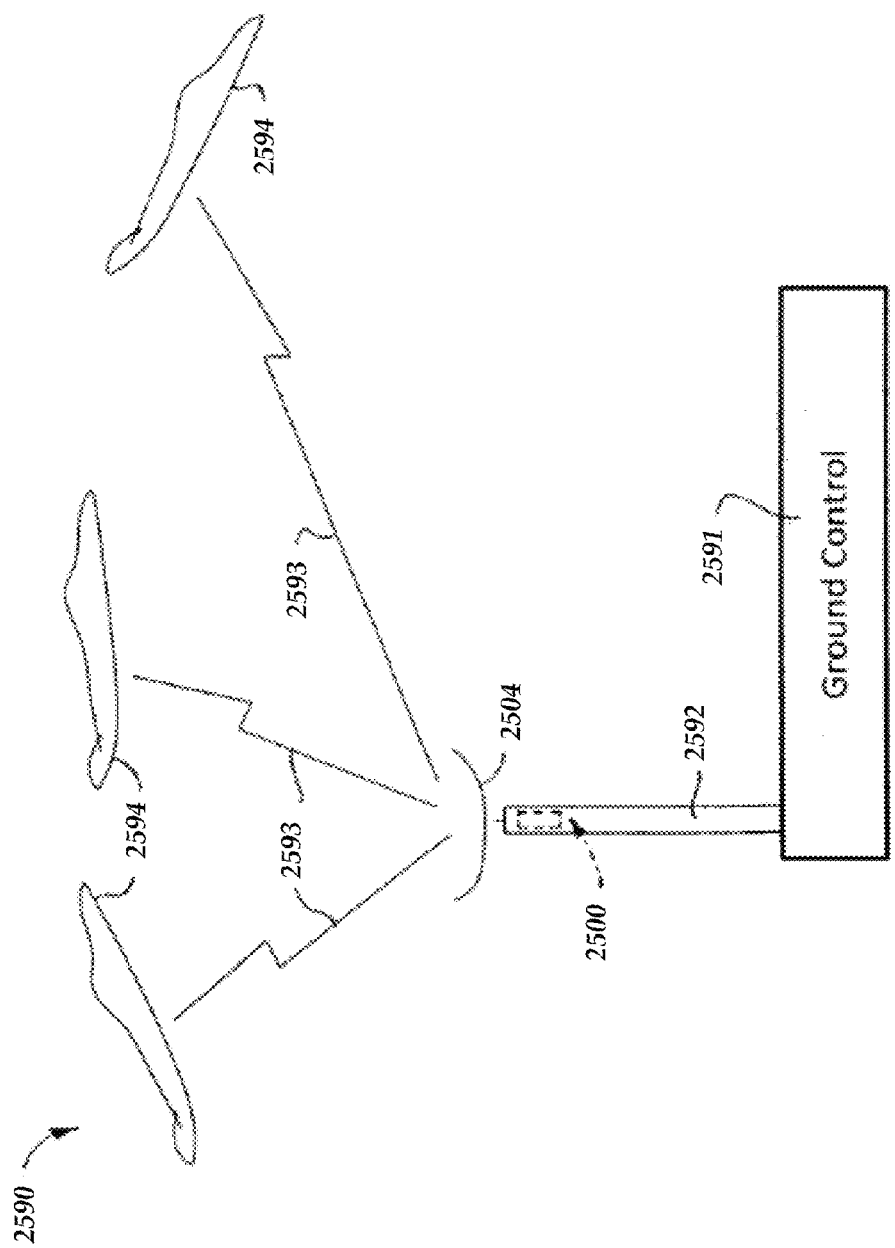
FIG. 25 is a schematic diagram that illustrates the implementation of one embodiment of a hybrid pulse compression system in a high resolution air traffic control system application.

Referring next to FIG. 25, a high resolution air traffic control system 2590 which utilizes an illustrative embodiment of a hybrid pulse compression system 2500 is illustrated. As described above, the hybrid pulse compression system 2500 can use poly-phase code waveforms and enhanced waveforms to detect an object. The air traffic control system 2590 may include a ground control 2591 having a ground control tower 2592. The hybrid pulse compression system 2500 may be provided in the ground control tower 2592. An antenna 2504 of the hybrid pulse compression system 2500 emits pulses 2593 (e.g., poly-phase code waveform pulses, enhanced waveform pulses, etc.) that are reflected from flying aircraft 2594. Pulses reflected from the aircraft 2594 (not illustrated) are received by the antenna 2504 and processed in a manner as described herein to generate a high-resolution image of the aircraft 2594.

Air traffic control systems are critically dependent on the use of RADAR technology for the safety of tens of thousands of aircrafts and millions of passengers every day. With the increase in air traffic, there is need for high resolution air traffic tracking systems. Currently, pulsed radars and FMCW radars are used for range measurement and Doppler measurements. With the use of the hybrid pulse compression system 2500, the performance of the air traffic systems 2590 can be significantly improved with more accurate estimation and detection of aircraft 2594. In particular, the relative positions of those aircraft 2594 which would otherwise come within dangerously close proximity to each other may be detected sufficiently early to prevent such close proximity and avert potential aviation accidents.

In addition to the example use cases described above, the hybrid pulse compression system described herein can be implemented in medical scanning devices (e.g., implemented within the computer system, coils, magnet, scanner, etc. of MRI machines, implemented within the gantry, X-RAY tube, detector, control console, etc. of CT scanners, etc.), watercraft like submarines or ships (e.g., as part of the components used for SONAR applications), aircraft (e.g., as part of the components used for RADAR applications), and/or the like.

Terminology

The terms "approximately," "about," and "substantially" as used herein represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements or steps. Thus, such conditional language is not generally intended to imply that features, elements or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A target detection system, the system comprising:
 a signal generator configured to generate a linear frequency modulation (LFM) waveform and a partially randomized LFM waveform;
 a transmitter configured to transmit the LFM waveform and the partially randomized LFM waveform in a sequential order;
 a receiver configured to receive a reflected LFM waveform and a reflected partially randomized LFM waveform, wherein the reflected LFM waveform comprises a version of the LFM waveform that reflected off a target, and wherein the reflected partially randomized LFM waveform comprises a version of the partially LFM waveform that reflected off the target;
 a processor in communication with the receiver and the signal generator and configured with specific computer-executable instructions to:
  process the reflected LFM waveform using the generated LFM waveform to form a processed LFM waveform;

process the reflected partially randomized LFM waveform using the generated partially randomized LFM waveform to form a processed partially randomized LFM waveform; and
combine the processed LFM waveform and the processed partially randomized LFM waveform to form a hybrid waveform; and
a display device configured to display a graphical representation of the hybrid waveform in a user interface.

2. The target detection system of claim 1, wherein the transmitter is configured to transmit the LFM waveform before the partially randomized LFM waveform.

3. The target detection system of claim 2, wherein the receiver is configured to receive the reflected LFM waveform before the reflected partially randomized LFM waveform.

4. The target detection system of claim 1, wherein the transmitter is configured to transmit the LFM waveform after the partially randomized LFM waveform.

5. The target detection system of claim 4, wherein the receiver is configured to receive the reflected LFM waveform after the reflected partially randomized LFM waveform.

6. The target detection system of claim 1, wherein the transmitter is further configured to concatenate the LFM waveform and the partially randomized LFM waveform.

7. The target detection system of claim 6, wherein the transmitter is further configured to insert a time delay corresponding to no signal between the LFM waveform and the partially randomized LFM waveform.

8. The target detection system of claim 1, wherein the processor is further configured with specific computer-executable instructions to:
cross-correlate the reflected LFM waveform with the generated LFM waveform to form the processed LFM waveform; and
cross-correlate the reflected partially randomized LFM waveform with the generated partially randomized LFM waveform to form the processed partially randomized LFM waveform.

9. The target detection system of claim 1, wherein the processor is further configured with specific computer-executable instructions to compute a product of the processed LFM waveform and the processed partially randomized LFM waveform.

10. The target detection system of claim 1, wherein the signal generator is further configured to:
group one or more samples of the LFM waveform into one or more subgroups;
randomly permute samples in each subgroup using a random permutation to form a randomized signal;
compute a truncated fast Fourier transform (FFT) of the randomized signal; and
compute an inverse FFT of the truncated FFT to form the partially randomized LFM waveform.

11. The target detection system of claim 1, wherein the graphical representation comprises an indication of a location of the target.

12. The target detection system of claim 1, wherein the LFM waveform is generated at a first bandwidth frequency, and wherein the partially randomized LFM waveform is generated at the first bandwidth frequency.

13. The target detection system of claim 1, wherein the target detection system is one of a radio detection and ranging (RADAR) system, a light detection and ranging (LIDAR) system, a sound navigation and ranging (SONAR) system, an ultrasound system, a magnetic resonance imaging (MRI) system, or a computing tomography (CT) system.

14. A method for detecting a target, the method comprising:
as implemented by a target detection system comprising physical hardware,
generating a poly-phase code waveform;
generating a partially randomized poly-phase code waveform;
transmitting the poly-phase code waveform and the partially randomized poly-phase code waveform in a sequential order;
receiving a reflected poly-phase code waveform and a reflected partially randomized poly-phase code waveform, wherein the reflected poly-phase code waveform comprises a version of the poly-phase code waveform that reflected off a target, and wherein the reflected partially randomized poly-phase code waveform comprises a version of the partially poly-phase code waveform that reflected off the target;
processing the reflected poly-phase code waveform using the generated poly-phase code waveform to form a processed poly-phase code waveform;
processing the reflected partially randomized poly-phase code waveform using the generated partially randomized poly-phase code waveform to form a processed partially randomized poly-phase code waveform; and
combining the processed poly-phase code waveform and the processed partially randomized poly-phase code waveform to form a hybrid waveform that, when graphically displayed, indicates whether the target is detected.

15. The method of claim 14, wherein transmitting the poly-phase code waveform and the partially randomized poly-phase code waveform further comprises transmitting the poly-phase code waveform before the partially randomized poly-phase code waveform.

16. The method of claim 15, wherein receiving a reflected poly-phase code waveform and a reflected partially randomized poly-phase code waveform further comprises receiving the reflected poly-phase code waveform before the reflected partially randomized poly-phase code waveform.

17. The method of claim 14, further comprising concatenating the poly-phase code waveform and the partially randomized poly-phase code waveform.

18. The method of claim 14, wherein processing the reflected poly-phase code waveform, processing the reflected partially randomized poly-phase code waveform, and combining the processed poly-phase code waveform and the processed partially randomized poly-phase code waveform further comprises:
cross-correlating the reflected poly-phase code waveform with the generated poly-phase code waveform to form the processed poly-phase code waveform;
cross-correlating the reflected partially randomized poly-phase code waveform with the generated partially randomized poly-phase code waveform to form the processed partially randomized poly-phase code waveform; and
computing a product of the processed poly-phase code waveform and the processed partially randomized poly-phase code waveform.

19. The method of claim 14, wherein the poly-phase code waveform is one of a linear frequency modulation (LFM) waveform, a Gold code waveform, or a Barker code waveform.

20. The method of claim 14, wherein the target detection system is one of a radio detection and ranging (RADAR) system, a light detection and ranging (LIDAR) system, a sound navigation and ranging (SONAR) system, an ultrasound system, a magnetic resonance imaging (MRI) system, or a computing tomography (CT) system.

\* \* \* \* \*